US008241629B2

(12) United States Patent
Jaspers et al.

(10) Patent No.: US 8,241,629 B2
(45) Date of Patent: *Aug. 14, 2012

(54) ANTI-HUMAN IL-21 MONOCLONAL ANTIBODIES

(75) Inventors: Stephen R. Jaspers, Edmonds, WA (US); Mark W. Rixon, Issaquah, WA (US); Stacey R. Dillon, Seattle, WA (US); Frederick J. Ramsdell, Bainbridge Island, WA (US); Cecile M. Krejsa, Seattle, WA (US); Eugene C. Yi, Mill Creek, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/971,495

(22) Filed: Dec. 17, 2010

(65) Prior Publication Data
US 2011/0130548 A1 Jun. 2, 2011

Related U.S. Application Data

(62) Division of application No. 12/330,334, filed on Dec. 8, 2008, now Pat. No. 7,883,700.

(60) Provisional application No. 61/012,329, filed on Dec. 7, 2007.

(51) Int. Cl.
*A61K 39/395* (2006.01)

(52) U.S. Cl. ............. 424/133.1; 530/388.23; 530/388.1; 530/809; 530/351

(58) Field of Classification Search .................. None
See application file for complete search history.

(56) References Cited

U.S. PATENT DOCUMENTS

| | | | |
|---|---|---|---|
| 6,057,128 A | 5/2000 | Donaldson et al. |
| 6,307,024 B1 | 10/2001 | Novak et al. |
| 6,605,272 B2 | 8/2003 | Novak et al. |
| 6,682,736 B1 | 1/2004 | Hanson et al. |
| 6,686,178 B2 | 2/2004 | Novak et al. |
| 6,929,932 B2 | 8/2005 | Presnell et al. |
| 7,473,765 B2 | 1/2009 | Novak et al. |
| 7,491,800 B2 | 2/2009 | Novak et al. |
| RE41,129 E | 2/2010 | Novak et al. |
| 7,923,539 B2 | 4/2011 | Sivakumar et al. |
| 2003/0108549 A1 | 6/2003 | Carter et al. |
| 2004/0016010 A1 | 1/2004 | Kasaian et al. |
| 2004/0136954 A1 | 7/2004 | Grusby et al. |
| 2004/0260065 A1 | 12/2004 | Novak et al. |
| 2005/0019343 A1 | 1/2005 | Schenk |
| 2005/0244390 A1 | 11/2005 | Garner et al. |
| 2006/0024268 A1 | 2/2006 | Kasaian et al. |
| 2006/0039902 A1 | 2/2006 | Young et al. |
| 2006/0159655 A1 | 7/2006 | Collins et al. |
| 2007/0014800 A1 | 1/2007 | Novak et al. |
| 2007/0041974 A1 | 2/2007 | Novak et al. |
| 2007/0048259 A1 | 3/2007 | Novak et al. |
| 2007/0048260 A1 | 3/2007 | Novak et al. |
| 2007/0048845 A1 | 3/2007 | Novak et al. |
| 2007/0049529 A1 | 3/2007 | Novak et al. |
| 2007/0054320 A1 | 3/2007 | Novak et al. |
| 2007/0059825 A1 | 3/2007 | Novak et al. |
| 2007/0066807 A1 | 3/2007 | Novak et al. |
| 2007/0066808 A1 | 3/2007 | Novak et al. |
| 2007/0092485 A1 | 4/2007 | Novak et al. |
| 2007/0098682 A1 | 5/2007 | Novak et al. |
| 2007/0098683 A1 | 5/2007 | Novak et al. |
| 2007/0099269 A1 | 5/2007 | Novak et al. |
| 2007/0122413 A1 | 5/2007 | Sivakumar et al. |
| 2007/0128189 A1 | 6/2007 | Sivakumar et al. |
| 2007/0166794 A1 | 7/2007 | Novak et al. |
| 2007/0172457 A1 | 7/2007 | Ebner et al. |

FOREIGN PATENT DOCUMENTS

| | | |
|---|---|---|
| JP | 2005-306757 | 11/2005 |
| WO | 00/53761 A2 | 9/2000 |
| WO | 03/087320 A2 | 10/2003 |
| WO | 03/103589 | 12/2003 |
| WO | 2004/032857 | 4/2004 |
| WO | 2004/056392 | 7/2004 |
| WO | 2005/037306 | 4/2005 |
| WO | 2006/057027 A1 | 6/2006 |
| WO | 2006/105538 A2 | 10/2006 |
| WO | 2007/111714 A2 | 10/2007 |

OTHER PUBLICATIONS

U.S. Appl. No. 11/346,580, filed Feb. 2, 2006, Novak et al.
U.S. Appl. No. 12/179,003, filed Jul. 24, 2008, Sivakumar.
Clegg et al., "Therapeutic opportunities for IL-21," *European Cytokine Network* 14(3):28, 2003.
Nelson et al., "Interleukin 21 has anti-tumor activity in animal models without the toxicity of IL-2," Proceedings of the American Association for Cancer Research Annual Meeting 44:562, 2003.
Funaro et al., "Monoclonal antibodies and therapy of human cancers," *Biotechnology Advances* 18(5):385-401, 2000.
Ozaki et al., "Regulation of B cell differentiation and plasma cell generation by IL-21, a novel inducer of Blimp-1 and Bc1-6," *J Immunol.* 173(9):5361-71, 2004.
Aklulu et al., "Depletion of normal B cells with rituximab as an adjunct to IL-2 therapy for renal cell carcinoma and melanoma," *Ann Oncol.* 15(7):1109-14, 2004.
Moroz et al., "IL-21 enhances and sustains CD8+ T cell responses to achieve duragble tumor immunity: comparative evaluation of IL-2, IL-15, and IL-21," *J Immunol.* 173(2):900-9, 2004.
O'Shea et al., "Jak3 and the pathogenesis of severe combined immunodeficiency," *Mol Immunol.* 727-37, 2004.
Sivakumar et al., Interleukin-21 is a T-helper cytokine that regulates humoral immunity and cell-mediated anti-tumor responses,: *Immunology* 112(2):177-82, 2004.

(Continued)

*Primary Examiner* — Dong Jiang

(74) *Attorney, Agent, or Firm* — Nelson Mullins Riley & Scarborough LLP; Jane E. Remillard, Esq.; Jeanne M. DiGiorgio, Esq.

(57) ABSTRACT

Human anti-human IL-21 monoclonal antibodies and the hybridomas that produce them are presented. Certain of these antibodies have the ability to bind native human IL-21, a mutant recombinat IL-21 protein and/or peptide regions of human IL-21. These human anti-IL-21 antibodies are useful in therapeutic treatment of autoimmune and inflammatory diseases, particularly diseases mediated by T follicular helper cells, B cells $T_H$ cells or $T_H 17$ cells.

11 Claims, 4 Drawing Sheets

OTHER PUBLICATIONS

Munshi, "Recent advances in the management of multiple myeloma," *Semin Hematol*. 2(4):21-6, 2004.

Rowshani et al., "Effects of CD25 monoclonal antibody on proliferative and effector functions of alloactivated human T cells in vitro," *Eur J Immunol*. 34(3):882-99, 2004.

Sievers et al., "IL-21 enhances trastuzumab-mediated killing of breast cancer cell lines in vitro," *Breast Cancer Res. and Treatment* S1(0):6075, 2004.

Kindsvogel et al., "IL-21 enhances rituximab-mediated killing of B-lymphoma cell lines in vitro and in vivo," *J. Clin. Oncol.* 22(14S):2581, 2004.

Hughes et al., "interleukin 21 efficacy in a mouse model of metastatic renal cell carcinoma," *J. Clin. Oncol.* 22(14S)2597, 2004.

Sivakumar et al., "Interleukin-21 Elicits Durable T and NK Cytotoxicity: Basic Biology to Clinical Trials.,"*J. Immunother.* 27(6):S56, 2004.

Hughes et al., "Mechanisms of IL-21 Enhancement of Rituximab Efficacy in a Lymphoma Xenograft Model," *Blood* 104(11):394A, 2004.

Rastetter et al., "Rituximab: expanding role in therapy for lymphomas and autoimmune diseases,"*Annu Rev Med*. 55:477-503, 2004.

Akamatsu et al., "Selected IL-21R Expression and Apoptosis Induction by IL-21 in Follicular Lymphoma," *Blood* 104(11):629A, 2004.

Ueda et al., "Expression of Functional IL-21 Receptor on adult T-cell Leukemia Cells," *Blood* 102(11), 2003.

Gitlitz et al., "Cytokine-based therapy for metastatic renal cell cancer," *Urol Clin North Am*. (3):589-600, 2003.

Ma et al., IL-21 activates both innate and adaptive immunity to generate potent antitumor responses that require perforin but are independent of IFN-gamms, *J. Immunol.* 171(2):608-15, 2003.

Mehta et al., "IL-21 induces the apoptosis of resting and activated primary B cells,"*J Immunol..* 170(8):4111-8, 2003.

Strengell et al., "IL-21 up-regulates the expression of genes associated with innate immunity and Th1 response," *J Immunol.* 169(7):3600-5, 2002.

Nelson et al., "Anti-tumor Effects of Interleukin 21," Immunobiology of Lymphomna abstr. 593, 2002.

Parrish-Novak et al., "Interleukin 21 and its receptor are involved in NK cell expansion and regulation of lymphocyte function," *Nature* 408(6808):57-63, 2000.

Ro et al., "IL-21 is a Growth and Survival Factor for Human Myeloma Cells," *Blood* 98(11):abst. 3216, 2001.

Stauber et al., "Crystal structure of the IL-2 signaling complex: Paradigm for a deterotrimeric cytokine receptor," *PNAS* 103(8):2788-1793, 2006.

Zhang et al., "Human IL-21 and IL-4 bind to partially overlapping epitopes of common γ-chain," *Biochem and Biophys Res Comm* 300:291-296, 2003.

Habib et al., "The common γ Chain (γc) Is a Required Signaling Component of the IL-21 Receptor and Supports IL-2I-Indiced Cell Proliferation via JAK3," *Biochemistry* 41:8725-8731, 2002.

Olosz et al., "Structural Basis for Binding Multiple Ligands by the Common Cytokine Receptor γ-Chain," *J. Biol. Chem.* 277(14):12047-12052, 2002.

Bondensgaard et al., "The existence of multiple conformers of interleukin-21 directs engineering of a superpotent alanlgue,"*J. Biol. Chem.* 282(32):23326-36, 2007.

Weidemann et al., "Beyond dimerization: a membrane-dependent activation model for interleukin-4 receptor-mediated signaling," *J. Mol Biol* 366(5):1365-73, 2007.

Brtandt et al., "Generation of Antagonists by Amino Acid Replacement in the D-Helix of Human IL-21," *J. Leuk Biol Supp.* 2001.

Onoda, Masashi et al., "IL-21 expression analysis trials using anti-human IL-21 monoclonal antibody," Proceedings of the 35th Meeting of the Japanese Society for Immunology, p. 286, Abstract No. 3-H-W47-14-O/P (2005).

Alexopoulos, Sophoclis et al., "Tolerance Induction Using IL-21 Antagonizing Fusion Protein," Experimental Tolerance Induction I, p. 186, Poster Board #-Session P97-1, Abstract No. 101 (2004).

Brandt, Katja et al., "Interleukin-21 inhibits dendritic cell activation and maturation," Blood, vol. 102(12):4090-4098 (2003).

Brandt, Katja et al., "Interleukin-21 Inhibits Dendritic Cell-Mediated T Cell Activation and Induction of Contact Hypersensitivity in Vivo," J. Invest. Dermatol., vol. 121:1379-1382 (2003).

Caruso, Roberta et al., "A Functional Role for Interleukin-21 in Promoting the Synthesis of the T-Cell Chemoattractant, MIP-3alpha, by Gut Epithelial Cells," Gastroenterology, vol. 132:166-175 (2007).

Cohen, J. et al., "Increased expression of CD132 and multiple IL-2 family receptors in *Psoriasis vulgaris*," The Journal of Investigative Dermatology, Abstract No. 0115 (2003).

Distler, Jorg et al., "Inflammation-independent Overexpression of IL-21 Receptor mRNA in Keratinocytes from Patients with Systemic Sclerosis," American College of Rheumatology, p. S353, Abstract No. 848 (2003).

Distler, Jorg H. et al., "Overexpression of IL-21 Receptor mRNA in the Epidermis of Patients with Systemic Sclerosis: Lessons from the SCID Mouse Transplantation Model," Annals of the Rheumatic Diseases, vol. 63(S1):107, Abstract No. OP0158 (2004).

Hecker, M. et al., "Novel genetic variation of human interleukin-21 receptor is associated with elevated IgE levels in females," Genes and Immunity, vol. 4:228-233 (2003).

Kasaian, Marion et al., "IL21 blocks IL15-induced NK cell expansion and enhances IFNgamma production," Journal of Leukocyte Biology Supplement, p. 36, abstract No. 76 (2001).

O'Shea, John J. et al., "A New Modality for Immunosuppression: Targeting the JAK/STAT Pathway," Nature Reviews Drug Discovery, vol. 3:555-564 (2004).

Suto, Akira et al., "Interleukin 21 prevents antigen-induced IgE production by inhibiting germ line Cε transcription of IL-4-stimulated B cells," Blood, vol. 4565-4573 (2002).

Wood, Nancy et al., "IL-21 effects on human IgE production in response to IL-4 or IL-13," Cellular Immunology, vol. 231:133-145 (2004).

Fig. 1

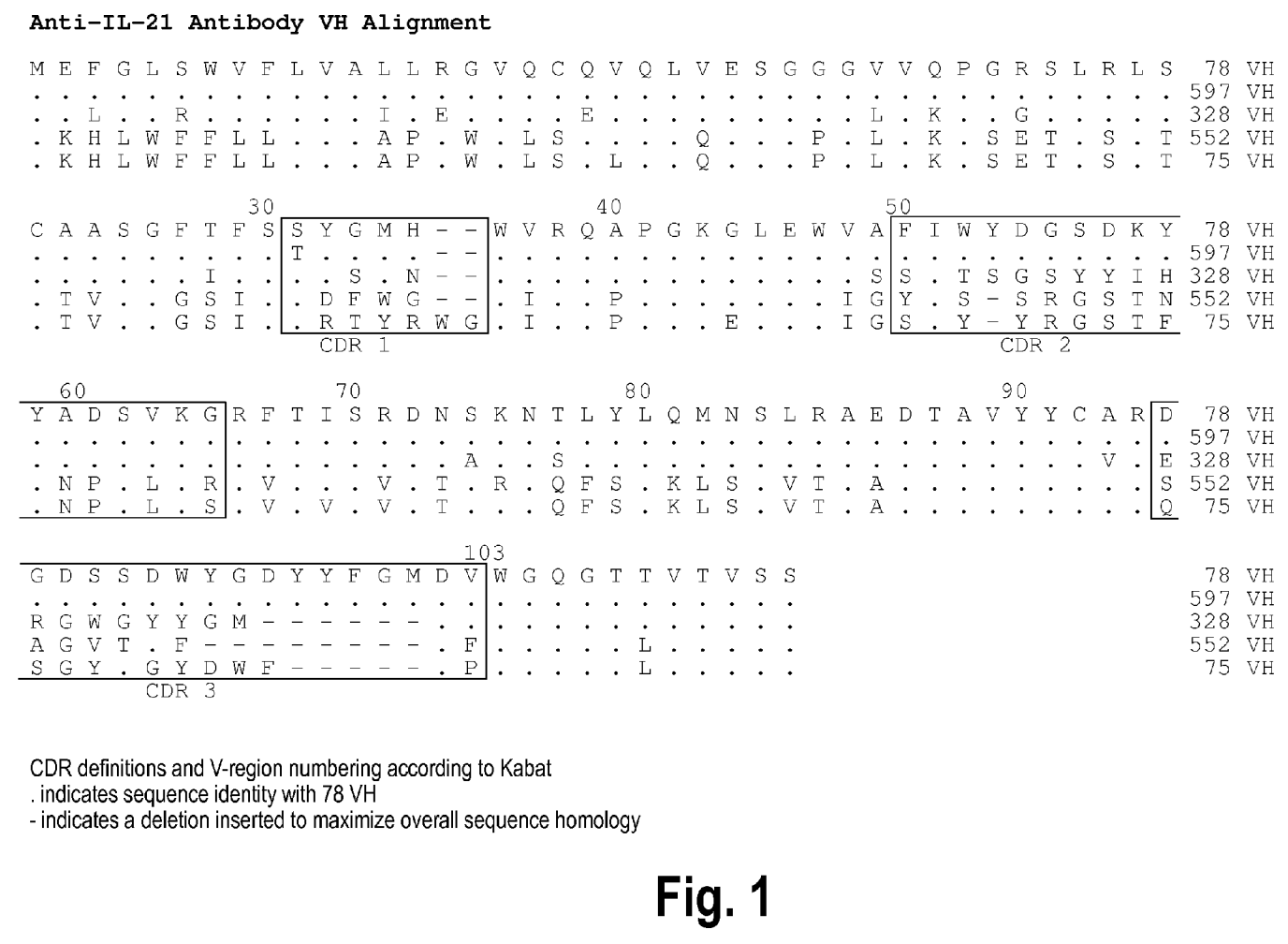

Anti-IL-21 Antibody VH Alignment

CDR definitions and V-region numbering according to Kabat
. indicates sequence identity with 78 VH
- indicates a deletion inserted to maximize overall sequence homology Anti-IL-21 Antibody VL Alignment

```
1                                                                                     
        M E T P A Q L L F L L L W L P D T T G E I V L T Q S P G T L S L S P G E R    78  VL
M D . . . R V . . . . . . . G . . . . . . . Q . . . . . . . . . A . . . . . D .    597 VL
M D . . . M V . . . . . . . G . . . . . . . D Q . . . . . . . V . A . . . V D .    328 VL
. . . . . A . . . . . . . . F . . . . . . . . M . . . . . . . . A . . . . . . .    552 VL
                                                                                      75  VL 20                                                   50
      A T L S C R A S Q S V S S S Y L A W Y Q Q K P G Q A P R L L I Y G A S S R A T G    78  VL
. . . . . . . . . . - D I D . . . . . . . . . . . . . . K . . . . H D . . . L E S .    597 VL
V . . . . . . . . . - I T . . A . . . . . . . . K . . . . K I . . V D . . . L Q S .    328 VL
V . . . . . . . . . - I T . . W . . . . . . . . K . . . . K . . . . D . . . . . N .    552 VL
. . . . . . . . . . - S V . . F . . . . . . . . . . . . . . . . . . . . . . . . .     75  VL
                          CDR 1                                          CDR 2

80
      I P D R F S G S G S G T D F T L T I S R L E P E D F A V Y Y C Q Q Y G S - - W T    78  VL
. . . . . . . . . . . . . . . . . . . . . . S . . Q . . . . . . . T . . F N . Y P Y .   597 VL
V . . . . . . . . . . . . . . . . . . . . . S . . Q . . . . . . . T . . A N . F P L .   328 VL
V . . . . . . . . . . . . . . . . . . . . . S . . . . . . . . . . . . . R S N - W I .   552 VL
A . . . . . . . . . . . . . . . . . . . . . . . . . . . . . . . . . . . . . . . . .      75 VL
                                                                        CDR 3

105
F G Q G T K V E I K    78  VL
. . . . . . L . . .    597 VL
. . . G . . . . . .    328 VL
. . . . . R L . . .    552 VL
                       75  VL
```

CDR definitions and V-region numbering according to Kabat
. indicates sequence identity with 78 VH
- indicates a deletion inserted to maximize overall sequence homology

Fig. 2

SEQUENCE LISTING

```
<160> NUMBER OF SEQ ID NOS: 97

<210> SEQ ID NO 1
<211> LENGTH: 642
<212> TYPE: DNA
<213> ORGANISM: Homo sapiens

<400> SEQUENCE: 1
gctgaagtga aaacgagacc aaggtctagc tctactgttg gtacttatga gatccagtcc      60
tggcaacatg gagaggattg tcatctgtct gatggtcatc ttcttgggga cactggtcca     120
caaatcaagc tcccaaggtc aagatcgcca catgattaga atgcgtcaac ttatagatat     180
tgttgatcag ctgaaaaatt atgtgaatga cttggtccct gaatttctgc cagctccaga     240
agatgtagag acaaactgtg agtggtcagc ttttcctgt tttcagaagg cccaactaaa     300
gtcagcaaat acaggaaaca atgaaaggat aatcaatgta tcaattaaaa agctgaagag     360
gaaaccacct tccacaaatg cagggagaag acagaaacac agactaacat gcccttcatg     420
tgattcttat gagaaaaaac cacccaaaga attcctagaa agattcaaat cacttctcca     480
aaagatgatt catcagcatc tgtcctctag aacacacgga agtgaagatt cctgaggatc     540
taacttgcag ttggacacta tgttacatac tctaatatag tagtgaaagt catttctttg     600
tattccaagt ggaggagccc tattaaatta tataaagaaa ta                       642

<210> SEQ ID NO 2
<211> LENGTH: 162
<212> TYPE: PRT
<213> ORGANISM: Homo sapiens

<400> SEQUENCE: 2

Met Arg Ser Ser Pro Gly Asn Met Glu Arg Ile Val Ile Cys Leu Met
 1               5                   10                  15

Val Ile Phe Leu Gly Thr Leu Val His Lys Ser Ser Ser Gln Gly Gln
                20                  25                  30

Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
        50                  55                  60

Glu Asp Val Glu Thr Asn Cys Glu Trp Ser Ala Phe Ser Cys Phe Gln
65                  70                  75                  80
```

-continued

```
Lys Ala Gln Leu Lys Ser Ala Asn Thr Gly Asn Asn Glu Arg Ile Ile
                85                  90                  95
Asn Val Ser Ile Lys Lys Leu Lys Arg Lys Pro Pro Ser Thr Asn Ala
            100                 105                 110
Gly Arg Arg Gln Lys His Arg Leu Thr Cys Pro Ser Cys Asp Ser Tyr
        115                 120                 125
Glu Lys Lys Pro Pro Lys Glu Phe Leu Glu Arg Phe Lys Ser Leu Leu
    130                 135                 140
Gln Lys Met Ile His Gln His Leu Ser Ser Arg Thr His Gly Ser Glu
145                 150                 155                 160
Asp Ser

<210> SEQ ID NO 3
<211> LENGTH: 21
<212> TYPE: PRT
<213> ORGANISM: Artificial Sequence
<220> FEATURE:
<223> OTHER INFORMATION: Peptide #1

<400> SEQUENCE: 3

Glu Gln Asp Arg His Met Ile Arg Met Arg Gln Leu Ile Asp Ile Val
1               5                   10                  15
Asp Gln Leu Lys Cys
            20

<210> SEQ ID NO 4
<211> LENGTH: 19
<212> TYPE: PRT
<213> ORGANISM: Artificial Sequence
<220> FEATURE:
<223> OTHER INFORMATION: Peptide #2

<400> SEQUENCE: 4

Asn Asp Leu Val Pro Glu Phe Leu Pro Ala Pro Glu Asp Val Glu Asn
1               5                   10                  15
Thr Asn Cys

<210> SEQ ID NO 5
<211> LENGTH: 26
<212> TYPE: PRT
<213> ORGANISM: Artificial Sequence
<220> FEATURE:
<223> OTHER INFORMATION: Peptide #3

<400> SEQUENCE: 5

Asn Val Ser Ile Lys Lys Leu Lys Arg Lys Pro Pro Ser Thr Asn Ala
1               5                   10                  15
Gly Arg Arg Gln Lys His Arg Leu Thr Cys
            20                  25

<210> SEQ ID NO 6
<211> LENGTH: 29
<212> TYPE: PRT
<213> ORGANISM: Artificial Sequence
<220> FEATURE:
<223> OTHER INFORMATION: Peptide #4

<400> SEQUENCE: 6

Cys Asp Ser Tyr Glu Lys Lys Pro Pro Lys Glu Phe Leu Glu Arg Phe
1               5                   10                  15
Lys Ser Leu Leu Gln Lys Met Ile His Gln His Leu Ser
            20                  25
```

<210> SEQ ID NO 7
<211> LENGTH: 162
<212> TYPE: PRT
<213> ORGANISM: Artificial Sequence
<220> FEATURE:
<223> OTHER INFORMATION: Mutant recombinant IL-21 aa

<400> SEQUENCE: 7

```
Met Asp Ser Ser Pro Gly Asn Met Glu Arg Ile Val Ile Cys Leu Met
 1               5                  10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
        50                  55                  60

Glu Asp Val Glu Thr Asn Cys Glu Trp Ser Ala Phe Ser Cys Phe Gln
 65                 70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
        130                 135                 140

Asp Lys Met Asp His Gln His Leu Ser Ser Arg Thr His Gly Ser Glu
145                 150                 155                 160

Asp Ser
```

<210> SEQ ID NO 8
<211> LENGTH: 545
<212> TYPE: DNA
<213> ORGANISM: Cynomylous

<400> SEQUENCE: 8

```
cgagaccaag gtctagctct actgttggta cttatgagat ccagtcctgg caacatggag      60
aggatagtca tctgtctgat ggtcatcttc ttggggacac tggtccacaa atcaagctcc     120
caaggtcaag atcgccacat gattagaatg cgtcaactta tagatattgt tgatcagctg     180
aaaaattatg tgaatgactt ggaccctgaa tttctgccag ctccagaaga tgtagagaca     240
aactgtgagt ggtcagctat ttcctgtttt cagaaggccc aactaaagtc agcaaataca     300
ggaaacaatg aaaggataat caatttatca attaaaaagc tgaagaggaa atcaccttcc     360
acaggtgcag agagaagaca gaaacacaga ctaacatgcc cttcatgtga ttcttatgag     420
aaaaaaccac ccaagaaatt cctagaaaga ttcaaatcac ttctccaaaa gatgattcat     480
cagcatctgt cctctagaac acatggaagt gaagattcct gaggatctaa cttgcagttg     540
gacac                                                                545
```

<210> SEQ ID NO 9
<211> LENGTH: 162
<212> TYPE: PRT
<213> ORGANISM: Cynomylous

<400> SEQUENCE: 9

```
Met Arg Ser Ser Pro Gly Asn Met Glu Arg Ile Val Ile Cys Leu Met
1               5                   10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
            35                  40                  45

Leu Lys Asn Tyr Val Asn Asp Leu Asp Pro Glu Phe Leu Pro Ala Pro
        50                  55                  60

Glu Asp Val Glu Thr Asn Cys Glu Trp Ser Ala Ile Ser Cys Phe Gln
65                  70                  75                  80

Lys Ala Gln Leu Lys Ser Ala Asn Thr Gly Asn Asn Glu Arg Ile Ile
                85                  90                  95

Asn Leu Ser Ile Lys Lys Leu Lys Arg Lys Ser Pro Ser Thr Gly Ala
            100                 105                 110

Glu Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
        130                 135                 140

Gln Lys Met Ile His Gln His Leu Ser Ser Arg Thr His Gly Ser Glu
145                 150                 155                 160

Asp Ser
```

<210> SEQ ID NO 10
<211> LENGTH: 3072
<212> TYPE: DNA
<213> ORGANISM: Murine

<400> SEQUENCE: 10

```
gagaaccaga ccaaggccct gtcatcagct cctggagact cagttctggt ggcatggaga      60
ggacccttgt ctgtctggta gtcatcttct tggggacagt ggcccataaa tcaagccccc     120
aagggccaga tcgcctcctg attagacttc gtcaccttat tgacattgtt aacagctga     180
aaatctatga aaatgacttg gatcctgaac ttctatcagc tccacaagat gtaaaggggc     240
actgtgagca tgcagctttt gcctgttttc agaaggccaa actcaagcca tcaaaccctg     300
gaaacaataa gacattcatc attgacctcg tgcccagct caggaggagg ctgcctgcca     360
ggagggagg aaagaaacag aagcacatag ctaaatgccc ttcctgtgat tcgtatgaga     420
aaaggacacc caagaattc ctagaaagac taaaatggcc ccttcaaaag atgattcatc     480
agcatctctc ctagaacaca taggacccga agattcctga ggatccgaga agattcccga     540
ggactgagga gacgccggac actatagacg ctcacgaatg caggagtaca tcttgcctct     600
tgggattgca agtggagaag tacgatacgt tatgataaga acaactcaga aaagctatag     660
gttaagatcc tttcgcccat taactaagca gacattgtgg ttccctgcac agactccatg     720
ctgtcaacat ggaaaatctc aactcaacaa gagcccagct tcccgtgtca gggatttctg     780
gtgcttctca agctgtggct tcatcttatt gcccaactgt gacattcttt gattggaagg     840
ggaaaactaa agcttttagc aaaaatacag ctagggaatt tgtcgatctg cgagagtaag     900
acctcttatg atcctaacgg aatgatgtaa gctggaaata ataagcataa gatgaaattg     960
aaaattgaag tctttattct ttaagaaaaa ctttgtactt gaaagcatgt ctgaagagtt    1020
tactcattac cacaaacatc tagcatattg ataactaaca tctttatact ctacaagaga    1080
ggctttccag ataggtacag ttttttcttct ctattaggtc tatcaaaatt taacctatta    1140
```

```
tgagggtcac ccctggcttt cactgttttt ctaaagaggc aagggtgtag taagaagcag    1200
gcttaagttg ccttcctccc aatgtcaagt tcctttataa gctaatagtt taatcttgtg    1260
aagatggcaa tgaaagcctg tggaagtgca acctcactca tcttctggag ccaagtagaa    1320
ttttcaagtt tgtagctctc acctcaagtg gttatgggtg tcctgtgatg aatctgctag    1380
ctccagcctc agtctcctct cccacatcct ttcctttctt tcctctttga aacttctaag    1440
aaaaagcaat ccaaacaagt tcagcactta agacacattg catgcacact tttgataagt    1500
taaatccaac catctatttta aaatcaaaat caggagatga gccaagagac cagaggttct    1560
gttccagttt taaacagact tttactgaac atcccaatct tttaaccaca gaggctaaat    1620
tgagcaaata gttttgccat ttgatataat ttccaacagt atgtttcaat gtcaagttaa    1680
aaagtctaca aagctatttt ccctggagtg gtatcatcgc tttgagaatt tcttatggtt    1740
aaaatggatc tgagatccaa gcatggcctg ggggatggtt ttgatctaag gaaaaaggtg    1800
tctgtacctc acagtgcctt taaaacaagc agagatcccg tgtaccgccc taagatagca    1860
cagactagtg ttaactgatt cccagaaaag tgtcacaatc agaaccaacg cattctctta    1920
aactttaaaa atatgtattg caagaacttg tgtaactgt aaatgtgtga ctgttgatga    1980
cattatacac acatagccca cgtaagtgtc caatggtgct agcattggtt gctgagtttg    2040
ctgctcgaaa gctgaagcag agatgcagtc cttcacaaag caatgatgga cagagagggg    2100
agtctccatg ttttattctt ttgttgtttc tggctgtgta actgttgact tcttgacatt    2160 gtgatttta tatttaagac aatgtattta ttttggtgtg tttattgttc tagccttttta    2220 aatcactgac aatttctaat caagaagtac aaataattca atgcagcaca ggctaagagc    2280
ttgtatcgtt tggaaaagcc agtgaaggct tctccactag ccatgggaaa gctacgcttt    2340
agagtaaact agacaaaatt gcacagcagt cttgaacctc tctgtgctca agactcagcc    2400
agtcctttga cattattgtt cactgtgggt gggaacacat tggacctgac acactgttgt    2460
gtgtccatga aggttgccac tggtgtaagc tttttttggt tttcattctc ttatctgtag    2520
aacaagaatg tggggctttc ctaagtctat tctgtatttt attctgaact tcgtatgtct    2580
gagttttaat gttttgagta ctcttacagg aacacctgac cacactttg agttaaattt    2640 tatcccaagt gtgatattta gttgttcaaa aagggaaggg atatacatac atacatacat    2700
acatacatac atatatatat atatatatac atatatatat atatatatat gtatatatat    2760
atatatatag agagagagag agagagagag agagaaagag agagaggttg ttgtaggtca    2820
taggagttca gaggaaatca gttatggccg ttaatactgt agctgaaagt gttttctttg    2880
tgaataaatt catagcatta ttgatctatg ttattgctct gttttatttta cagtcacacc    2940 tgagaattta gttttaatat gaatgatgta ctttataact taatgattat ttattatgta    3000
tttggttttg aatgtttgtg ttcatggctt cttatttaag acctgatcat attaaatgct    3060
acccagtccg ga                                                       3072
```

<210> SEQ ID NO 11
<211> LENGTH: 146
<212> TYPE: PRT
<213> ORGANISM: Murine

<400> SEQUENCE: 11

```
Met Glu Arg Thr Leu Val Cys Leu Val Val Ile Phe Leu Gly Thr Val
1               5                   10                  15

Ala His Lys Ser Ser Pro Gln Gly Pro Asp Arg Leu Leu Ile Arg Leu
            20                  25                  30
```

```
Arg His Leu Ile Asp Ile Val Glu Gln Leu Lys Ile Tyr Glu Asn Asp
         35                  40                  45

Leu Asp Pro Glu Leu Leu Ser Ala Pro Gln Asp Val Lys Gly His Cys
     50                  55                  60

Glu His Ala Ala Phe Ala Cys Phe Gln Lys Ala Lys Leu Lys Pro Ser
 65                  70                  75                  80

Asn Pro Gly Asn Asn Lys Thr Phe Ile Ile Asp Leu Val Ala Gln Leu
                 85                  90                  95

Arg Arg Arg Leu Pro Ala Arg Gly Gly Lys Lys Gln Lys His Ile
             100                 105                 110

Ala Lys Cys Pro Ser Cys Asp Ser Tyr Glu Lys Arg Thr Pro Lys Glu
         115                 120                 125

Phe Leu Glu Arg Leu Lys Trp Leu Leu Gln Lys Met Ile His Gln His
130                 135                 140

Leu Ser
145

<210> SEQ ID NO 12
<211> LENGTH: 423
<212> TYPE: DNA
<213> ORGANISM: Homo sapiens
<220> FEATURE:
<221> NAME/KEY: CDS
<222> LOCATION: (1)...(423)

<400> SEQUENCE: 12 atg aag cac ctg tgg ttc ttc ctc ctg ctg gtg gcg gct ccc aga tgg      48
Met Lys His Leu Trp Phe Phe Leu Leu Leu Val Ala Ala Pro Arg Trp
  1               5                  10                  15 gtc ctg tcc cag cta caa ctg cag gag tcg ggc cca gga ctg gtg aag      96
Val Leu Ser Gln Leu Gln Leu Gln Glu Ser Gly Pro Gly Leu Val Lys
             20                  25                  30 cct tcg gag acc ctg tcc ctc acc tgc act gtc tct ggt ggc tcc atc     144
Pro Ser Glu Thr Leu Ser Leu Thr Cys Thr Val Ser Gly Gly Ser Ile
         35                  40                  45 agc agt agg act tac cgc tgg ggc tgg atc cgc cag ccc cca ggg aag     192
Ser Ser Arg Thr Tyr Arg Trp Gly Trp Ile Arg Gln Pro Pro Gly Lys
     50                  55                  60 gaa ctg gag tgg att ggg agt atc tat tat aga ggg agt acc ttc tac     240
Glu Leu Glu Trp Ile Gly Ser Ile Tyr Tyr Arg Gly Ser Thr Phe Tyr
 65                  70                  75                  80 aac ccg tcc ctc aag agt cga gtc acc gta tcc gta gac acg tcc aag     288
Asn Pro Ser Leu Lys Ser Arg Val Thr Val Ser Val Asp Thr Ser Lys
                 85                  90                  95 aac cag ttc tcc ctg aaa ctg agc tct gtg acc gcc gca gac acg gct     336
Asn Gln Phe Ser Leu Lys Leu Ser Ser Val Thr Ala Ala Asp Thr Ala
            100                 105                 110 gtg tat tac tgt gcg aga cag agt gga tat agt ggc tac gac tgg ttc     384
Val Tyr Tyr Cys Ala Arg Gln Ser Gly Tyr Ser Gly Tyr Asp Trp Phe
        115                 120                 125 gac ccc tgg ggc cag gga acc ctg gtc acc gtc tcc tca                 423
Asp Pro Trp Gly Gln Gly Thr Leu Val Thr Val Ser Ser
130                 135                 140

<210> SEQ ID NO 13
<211> LENGTH: 141
<212> TYPE: PRT
<213> ORGANISM: Homo sapiens
```

<400> SEQUENCE: 13

Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Arg Thr Tyr Arg Trp Gly Trp Ile Arg Gln Pro Pro Gly Lys
    50                  55                  60

Glu Leu Glu Trp Ile Gly Ser Ile Tyr Tyr Arg Gly Ser Thr Phe Tyr
65                  70                  75                  80

Asn Pro Ser Leu Lys Ser Arg Val Thr Val Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Gln Ser Gly Tyr Ser Gly Tyr Asp Trp Phe
        115                 120                 125

Asp Pro Trp Gly Gln Gly Thr Leu Val Thr Val Ser Ser
    130                 135                 140

<210> SEQ ID NO 14
<211> LENGTH: 21
<212> TYPE: DNA
<213> ORGANISM: Homo sapiens
<220> FEATURE:
<221> NAME/KEY: CDS
<222> LOCATION: (1)...(21)

<400> SEQUENCE: 14 agt agg act tac cgc tgg ggc                                         21
Ser Arg Thr Tyr Arg Trp Gly
1               5

<210> SEQ ID NO 15
<211> LENGTH: 7
<212> TYPE: PRT
<213> ORGANISM: Homo sapiens

<400> SEQUENCE: 15

Ser Arg Thr Tyr Arg Trp Gly
1               5

<210> SEQ ID NO 16
<211> LENGTH: 48
<212> TYPE: DNA
<213> ORGANISM: Homo sapiens
<220> FEATURE:
<221> NAME/KEY: CDS
<222> LOCATION: (1)...(48)

<400> SEQUENCE: 16 agt atc tat tat aga ggg agt acc ttc tac aac ccg tcc ctc aag agt    48
Ser Ile Tyr Tyr Arg Gly Ser Thr Phe Tyr Asn Pro Ser Leu Lys Ser
1               5                   10                  15

<210> SEQ ID NO 17
<211> LENGTH: 16
<212> TYPE: PRT
<213> ORGANISM: Homo sapiens

<400> SEQUENCE: 17

Ser Ile Tyr Tyr Arg Gly Ser Thr Phe Tyr Asn Pro Ser Leu Lys Ser
1               5                   10                  15

<210> SEQ ID NO 18
<211> LENGTH: 36
<212> TYPE: DNA
<213> ORGANISM: Homo sapiens
<220> FEATURE:
<221> NAME/KEY: CDS
<222> LOCATION: (1)...(36)

<400> SEQUENCE: 18

```
cag agt gga tat agt ggc tac gac tgg ttc gac ccc          36
Gln Ser Gly Tyr Ser Gly Tyr Asp Trp Phe Asp Pro
1               5                   10
```

<210> SEQ ID NO 19
<211> LENGTH: 12
<212> TYPE: PRT
<213> ORGANISM: Homo sapiens

<400> SEQUENCE: 19

```
Gln Ser Gly Tyr Ser Gly Tyr Asp Trp Phe Asp Pro
1               5                   10
```

<210> SEQ ID NO 20
<211> LENGTH: 378
<212> TYPE: DNA
<213> ORGANISM: Homo sapiens
<220> FEATURE:
<221> NAME/KEY: CDS
<222> LOCATION: (1)...(378)

<400> SEQUENCE: 20

```
atg gaa gcc cca gct cag ctt ctc ttc ctc ctg cta ctc tgg ctc cca          48
Met Glu Ala Pro Ala Gln Leu Leu Phe Leu Leu Leu Leu Trp Leu Pro
1               5                   10                  15 gat acc acc gga gaa att gtg ttg aca cag tct cca gcc acc ctg tct          96
Asp Thr Thr Gly Glu Ile Val Leu Thr Gln Ser Pro Ala Thr Leu Ser
            20                  25                  30 ttg tct cca ggg gaa aga gcc acc ctc tcc tgc agg gcc agt cag agt         144
Leu Ser Pro Gly Glu Arg Ala Thr Leu Ser Cys Arg Ala Ser Gln Ser
        35                  40                  45 gtt agc agc ttc tta gcc tgg tac caa cag aaa cct ggc cag gct ccc         192
Val Ser Ser Phe Leu Ala Trp Tyr Gln Gln Lys Pro Gly Gln Ala Pro
    50                  55                  60 agg ctc ctc atc tat gat gca tcc aac agg gcc act ggc atc cca gcc         240
Arg Leu Leu Ile Tyr Asp Ala Ser Asn Arg Ala Thr Gly Ile Pro Ala
65                  70                  75                  80 agg ttc agt ggc agt ggg tct ggg aca gac ttc act ctc acc atc agc         288
Arg Phe Ser Gly Ser Gly Ser Gly Thr Asp Phe Thr Leu Thr Ile Ser
                85                  90                  95 agc cta gag cct gaa gat ttt gca gtt tat tac tgt cag cag cgt agc         336
Ser Leu Glu Pro Glu Asp Phe Ala Val Tyr Tyr Cys Gln Gln Arg Ser
            100                 105                 110 aac tgg atc acc ttc ggc caa ggg aca cga ctg gag att aaa             378
Asn Trp Ile Thr Phe Gly Gln Gly Thr Arg Leu Glu Ile Lys
        115                 120                 125
```

<210> SEQ ID NO 21
<211> LENGTH: 126
<212> TYPE: PRT
<213> ORGANISM: Homo sapiens -continued

```
<400> SEQUENCE: 21

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Phe Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Ile Thr Phe Gly Gln Gly Thr Arg Leu Glu Ile Lys
        115                 120                 125

<210> SEQ ID NO 22
<211> LENGTH: 33
<212> TYPE: DNA
<213> ORGANISM: Homo sapiens
<220> FEATURE:
<221> NAME/KEY: CDS
<222> LOCATION: (1)...(33)

<400> SEQUENCE: 22 agg gcc agt cag agt gtt agc agc ttc tta gcc                     33
Arg Ala Ser Gln Ser Val Ser Ser Phe Leu Ala
1               5                   10

<210> SEQ ID NO 23
<211> LENGTH: 11
<212> TYPE: PRT
<213> ORGANISM: Homo sapiens

<400> SEQUENCE: 23

Arg Ala Ser Gln Ser Val Ser Ser Phe Leu Ala
1               5                   10

<210> SEQ ID NO 24
<211> LENGTH: 21
<212> TYPE: DNA
<213> ORGANISM: Homo sapiens
<220> FEATURE:
<221> NAME/KEY: CDS
<222> LOCATION: (1)...(21)

<400> SEQUENCE: 24 gat gca tcc aac agg gcc act                                     21
Asp Ala Ser Asn Arg Ala Thr
1               5

<210> SEQ ID NO 25
<211> LENGTH: 7
<212> TYPE: PRT
<213> ORGANISM: Homo sapiens

<400> SEQUENCE: 25

Asp Ala Ser Asn Arg Ala Thr
1               5
```

<210> SEQ ID NO 26
<211> LENGTH: 24
<212> TYPE: DNA
<213> ORGANISM: Homo sapiens
<220> FEATURE:
<221> NAME/KEY: CDS
<222> LOCATION: (1)...(24)

<400> SEQUENCE: 26

```
cag cag cgt agc aac tgg atc acc                                          24
Gln Gln Arg Ser Asn Trp Ile Thr
  1               5
```

<210> SEQ ID NO 27
<211> LENGTH: 8
<212> TYPE: PRT
<213> ORGANISM: Homo sapiens

<400> SEQUENCE: 27

```
Gln Gln Arg Ser Asn Trp Ile Thr
  1               5
```

<210> SEQ ID NO 28
<211> LENGTH: 435
<212> TYPE: DNA
<213> ORGANISM: Homo sapiens
<220> FEATURE:
<221> NAME/KEY: CDS
<222> LOCATION: (1)...(435)

<400> SEQUENCE: 28

```
atg gag ttt ggg ctg agc tgg gtt ttc ctc gtt gct ctt tta aga ggt          48
Met Glu Phe Gly Leu Ser Trp Val Phe Leu Val Ala Leu Leu Arg Gly
  1               5                  10                  15 gtc cag tgt cag gtg cag ctg gtg gag tct ggg gga ggc gtg gtc cag          96
Val Gln Cys Gln Val Gln Leu Val Glu Ser Gly Gly Gly Val Val Gln
             20                  25                  30 cct ggg agg tcc ctg aga ctc tcc tgt gca gcg tct gga ttc acc ttc         144
Pro Gly Arg Ser Leu Arg Leu Ser Cys Ala Ala Ser Gly Phe Thr Phe
         35                  40                  45 agt agc tat ggc atg cac tgg gtc cgc cag gct cca ggc aag ggg ctg         192
Ser Ser Tyr Gly Met His Trp Val Arg Gln Ala Pro Gly Lys Gly Leu
     50                  55                  60 gag tgg gtg gcg ttt ata tgg tat gat gga agt gat aaa tac tat gca         240
Glu Trp Val Ala Phe Ile Trp Tyr Asp Gly Ser Asp Lys Tyr Tyr Ala
 65                  70                  75                  80 gac tct gtg aag ggc cga ttc acc atc tcc aga gac aat tcc aag aac         288
Asp Ser Val Lys Gly Arg Phe Thr Ile Ser Arg Asp Asn Ser Lys Asn
                 85                  90                  95 acg ctg tat ctg caa atg aac agc ctg aga gcc gag gac acg gct gtg         336
Thr Leu Tyr Leu Gln Met Asn Ser Leu Arg Ala Glu Asp Thr Ala Val
            100                 105                 110 tat tac tgt gcg aga gat ggg gat agc agt gac tgg tac ggg gac tac         384
Tyr Tyr Cys Ala Arg Asp Gly Asp Ser Ser Asp Trp Tyr Gly Asp Tyr
        115                 120                 125 tac ttc ggt atg gac gtc tgg ggc caa ggg acc acg gtc acc gtc tcc         432
Tyr Phe Gly Met Asp Val Trp Gly Gln Gly Thr Thr Val Thr Val Ser
    130                 135                 140 tca                                                                     435
Ser
145
```

```
<210> SEQ ID NO 29
<211> LENGTH: 145
<212> TYPE: PRT
<213> ORGANISM: Homo sapiens

<400> SEQUENCE: 29

Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Phe Ile Trp Tyr Asp Gly Ser Asp Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Gly Asp Ser Ser Asp Trp Tyr Gly Asp Tyr
        115                 120                 125

Tyr Phe Gly Met Asp Val Trp Gly Gln Gly Thr Thr Val Thr Val Ser
    130                 135                 140

Ser
145

<210> SEQ ID NO 30
<211> LENGTH: 16
<212> TYPE: DNA
<213> ORGANISM: Homo sapiens
<220> FEATURE:
<221> NAME/KEY: CDS
<222> LOCATION: (1)...(16)

<400> SEQUENCE: 30 agc tat ggc atg cac t                                         16
Ser Tyr Gly Met His
 1               5

<210> SEQ ID NO 31
<211> LENGTH: 5
<212> TYPE: PRT
<213> ORGANISM: Homo sapiens

<400> SEQUENCE: 31

Ser Tyr Gly Met His
 1               5

<210> SEQ ID NO 32
<211> LENGTH: 51
<212> TYPE: DNA
<213> ORGANISM: Homo sapiens
<220> FEATURE:
<221> NAME/KEY: CDS
<222> LOCATION: (1)...(51)

<400> SEQUENCE: 32 ttt ata tgg tat gat gga agt gat aaa tac tat gca gac tct gtg aag   48
Phe Ile Trp Tyr Asp Gly Ser Asp Lys Tyr Tyr Ala Asp Ser Val Lys
 1               5                  10                  15 ggc                                                               51
Gly
```

<210> SEQ ID NO 33
<211> LENGTH: 17
<212> TYPE: PRT
<213> ORGANISM: Homo sapiens

<400> SEQUENCE: 33

Phe Ile Trp Tyr Asp Gly Ser Asp Lys Tyr Tyr Ala Asp Ser Val Lys
1               5                   10                  15

Gly

<210> SEQ ID NO 34
<211> LENGTH: 51
<212> TYPE: DNA
<213> ORGANISM: Homo sapiens
<220> FEATURE:
<221> NAME/KEY: CDS
<222> LOCATION: (1)...(51)

<400> SEQUENCE: 34 gat ggg gat agc agt gac tgg tac ggg gac tac tac ttc ggt atg gac       48
Asp Gly Asp Ser Ser Asp Trp Tyr Gly Asp Tyr Tyr Phe Gly Met Asp
1               5                   10                  15 gtc                                                                   51
Val

<210> SEQ ID NO 35
<211> LENGTH: 17
<212> TYPE: PRT
<213> ORGANISM: Homo sapiens

<400> SEQUENCE: 35

Asp Gly Asp Ser Ser Asp Trp Tyr Gly Asp Tyr Tyr Phe Gly Met Asp
1               5                   10                  15

Val

<210> SEQ ID NO 36
<211> LENGTH: 378
<212> TYPE: DNA
<213> ORGANISM: Homo sapiens
<220> FEATURE:
<221> NAME/KEY: CDS
<222> LOCATION: (1)...(378)

<400> SEQUENCE: 36 atg gaa acc cca gcg cag ctt ctc ttc ctc ctg cta ctc tgg ctc cca       48
Met Glu Thr Pro Ala Gln Leu Leu Phe Leu Leu Leu Leu Trp Leu Pro
1               5                   10                  15 gat acc acc gga gaa att gtg ttg acg cag tct cca ggc acc ctg tct       96
Asp Thr Thr Gly Glu Ile Val Leu Thr Gln Ser Pro Gly Thr Leu Ser
                20                  25                  30 ttg tct cca ggg gaa aga gcc acc ctc tcc tgc agg gcc agt cag agt      144
Leu Ser Pro Gly Glu Arg Ala Thr Leu Ser Cys Arg Ala Ser Gln Ser
            35                  40                  45 gtt agc agc agc tac tta gcc tgg tac cag cag aaa cct ggc cag gct      192
Val Ser Ser Ser Tyr Leu Ala Trp Tyr Gln Gln Lys Pro Gly Gln Ala
        50                  55                  60 ccc agg ctc ctc atc tat ggt gca tcc agc agg gcc act ggc atc cca      240
Pro Arg Leu Leu Ile Tyr Gly Ala Ser Ser Arg Ala Thr Gly Ile Pro
65                  70                  75                  80 gac agg ttc agt ggc agt ggg tct ggg aca gac ttc act ctc acc atc      288
Asp Arg Phe Ser Gly Ser Gly Ser Gly Thr Asp Phe Thr Leu Thr Ile
                85                  90                  95

```
agc aga ctg gag cct gaa gat ttt gca gtg tat tac tgt cag cag tat      336
Ser Arg Leu Glu Pro Glu Asp Phe Ala Val Tyr Tyr Cys Gln Gln Tyr
        100                 105                 110 ggt agc tgg acg ttc ggc caa ggg acc aag gtg gaa atc aaa              378
Gly Ser Trp Thr Phe Gly Gln Gly Thr Lys Val Glu Ile Lys
    115                 120                 125
```

<210> SEQ ID NO 37
<211> LENGTH: 126
<212> TYPE: PRT
<213> ORGANISM: Homo sapiens

<400> SEQUENCE: 37

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Trp Thr Phe Gly Gln Gly Thr Lys Val Glu Ile Lys
        115                 120                 125
```

<210> SEQ ID NO 38
<211> LENGTH: 36
<212> TYPE: DNA
<213> ORGANISM: Homo sapiens
<220> FEATURE:
<221> NAME/KEY: CDS
<222> LOCATION: (1)...(36)

<400> SEQUENCE: 38

```
agg gcc agt cag agt gtt agc agc agc tac tta gcc                      36
Arg Ala Ser Gln Ser Val Ser Ser Ser Tyr Leu Ala
1               5                   10
```

<210> SEQ ID NO 39
<211> LENGTH: 12
<212> TYPE: PRT
<213> ORGANISM: Homo sapiens

<400> SEQUENCE: 39

```
Arg Ala Ser Gln Ser Val Ser Ser Ser Tyr Leu Ala
1               5                   10
```

<210> SEQ ID NO 40
<211> LENGTH: 21
<212> TYPE: DNA
<213> ORGANISM: Homo sapiens
<220> FEATURE:
<221> NAME/KEY: CDS
<222> LOCATION: (1)...(21)

<400> SEQUENCE: 40

```
ggt gca tcc agc agg gcc act                                          21
Gly Ala Ser Ser Arg Ala Thr
1               5
```

```
<210> SEQ ID NO 41
<211> LENGTH: 7
<212> TYPE: PRT
<213> ORGANISM: Homo sapiens

<400> SEQUENCE: 41

Gly Ala Ser Ser Arg Ala Thr
 1               5

<210> SEQ ID NO 42
<211> LENGTH: 21
<212> TYPE: DNA
<213> ORGANISM: Homo sapiens
<220> FEATURE:
<221> NAME/KEY: CDS
<222> LOCATION: (1)...(21)

<400> SEQUENCE: 42 cag cag tat ggt agc tgg acg                                          21
Gln Gln Tyr Gly Ser Trp Thr
 1               5

<210> SEQ ID NO 43
<211> LENGTH: 7
<212> TYPE: PRT
<213> ORGANISM: Homo sapiens

<400> SEQUENCE: 43

Gln Gln Tyr Gly Ser Trp Thr
 1               5

<210> SEQ ID NO 44
<211> LENGTH: 435
<212> TYPE: DNA
<213> ORGANISM: Homo sapiens
<220> FEATURE:
<221> NAME/KEY: CDS
<222> LOCATION: (1)...(435)

<400> SEQUENCE: 44 atg gag ttt ggg ctg agc tgg gtt ttc ctc gtt gct ctt tta aga ggt    48
Met Glu Phe Gly Leu Ser Trp Val Phe Leu Val Ala Leu Leu Arg Gly
 1               5                  10                  15 gtc cag tgt cag gtg cag ctg gtg gaa tct ggg gga ggc gtg gtc cag    96
Val Gln Cys Gln Val Gln Leu Val Glu Ser Gly Gly Gly Val Val Gln
                20                  25                  30 cct ggg agg tcc ctg aga ctc tcc tgt gca gcg tct gga ttc acc ttc   144
Pro Gly Arg Ser Leu Arg Leu Ser Cys Ala Ala Ser Gly Phe Thr Phe
            35                  40                  45 agt acc tat ggc atg cac tgg gtc cgc cag gct cca ggc aag ggg ctg   192
Ser Thr Tyr Gly Met His Trp Val Arg Gln Ala Pro Gly Lys Gly Leu
        50                  55                  60 gag tgg gtg gcc ttt ata tgg tat gat gga agt gat aaa tac tat gca   240
Glu Trp Val Ala Phe Ile Trp Tyr Asp Gly Ser Asp Lys Tyr Tyr Ala
    65                  70                  75                  80 gac tct gtg aag ggc cga ttc acc atc tcc aga gac aat tcc aag aac   288
Asp Ser Val Lys Gly Arg Phe Thr Ile Ser Arg Asp Asn Ser Lys Asn
                85                  90                  95 acg ctg tat ctg caa atg aac agc ctg aga gcc gag gac acg gct gtg   336
Thr Leu Tyr Leu Gln Met Asn Ser Leu Arg Ala Glu Asp Thr Ala Val
                100                 105                 110 tat tac tgt gcg aga gat ggg gat agc agt gac tgg tac ggg gac tac   384
Tyr Tyr Cys Ala Arg Asp Gly Asp Ser Ser Asp Trp Tyr Gly Asp Tyr
            115                 120                 125
```

```
tac ttc ggt atg gac gtc tgg ggc caa ggg acc acg gtc acc gtc tcc      432
Tyr Phe Gly Met Asp Val Trp Gly Gln Gly Thr Thr Val Thr Val Ser
        130                 135                 140 tca                                                                   435
Ser
145

<210> SEQ ID NO 45
<211> LENGTH: 145
<212> TYPE: PRT
<213> ORGANISM: Homo sapiens

<400> SEQUENCE: 45

Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Thr Tyr Gly Met His Trp Val Arg Gln Ala Pro Gly Lys Gly Leu
    50                  55                  60

Glu Trp Val Ala Phe Ile Trp Tyr Asp Gly Ser Asp Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Gly Asp Ser Ser Asp Trp Tyr Gly Asp Tyr
        115                 120                 125

Tyr Phe Gly Met Asp Val Trp Gly Gln Gly Thr Thr Val Thr Val Ser
    130                 135                 140

Ser
145

<210> SEQ ID NO 46
<211> LENGTH: 15
<212> TYPE: DNA
<213> ORGANISM: Homo sapiens
<220> FEATURE:
<221> NAME/KEY: CDS
<222> LOCATION: (1)...(15)

<400> SEQUENCE: 46 acc tat ggc atg cac                                                    15
Thr Tyr Gly Met His
 1               5

<210> SEQ ID NO 47
<211> LENGTH: 5
<212> TYPE: PRT
<213> ORGANISM: Homo sapiens

<400> SEQUENCE: 47

Thr Tyr Gly Met His
 1               5

<210> SEQ ID NO 48
<211> LENGTH: 51
<212> TYPE: DNA
<213> ORGANISM: Homo sapiens
<220> FEATURE:
<221> NAME/KEY: CDS
<222> LOCATION: (1)...(51)
```

-continued

<400> SEQUENCE: 48

```
ttt ata tgg tat gat gga agt gat aaa tac tat gca gac tct gtg aag      48
Phe Ile Trp Tyr Asp Gly Ser Asp Lys Tyr Tyr Ala Asp Ser Val Lys
1               5                   10                  15 ggc                                                                  51
Gly
```

<210> SEQ ID NO 49
<211> LENGTH: 17
<212> TYPE: PRT
<213> ORGANISM: Homo sapiens

<400> SEQUENCE: 49

```
Phe Ile Trp Tyr Asp Gly Ser Asp Lys Tyr Tyr Ala Asp Ser Val Lys
1               5                   10                  15

Gly
```

<210> SEQ ID NO 50
<211> LENGTH: 51
<212> TYPE: DNA
<213> ORGANISM: Homo sapiens
<220> FEATURE:
<221> NAME/KEY: CDS
<222> LOCATION: (1)...(51)

<400> SEQUENCE: 50

```
gat ggg gat agc agt gac tgg tac ggg gac tac tac ttc ggt atg gac      48
Asp Gly Asp Ser Ser Asp Trp Tyr Gly Asp Tyr Tyr Phe Gly Met Asp
1               5                   10                  15 gtc                                                                  51
Val
```

<210> SEQ ID NO 51
<211> LENGTH: 17
<212> TYPE: PRT
<213> ORGANISM: Homo sapiens

<400> SEQUENCE: 51

```
Asp Gly Asp Ser Ser Asp Trp Tyr Gly Asp Tyr Tyr Phe Gly Met Asp
1               5                   10                  15

Val
```

<210> SEQ ID NO 52
<211> LENGTH: 378
<212> TYPE: DNA
<213> ORGANISM: Homo sapiens
<220> FEATURE:
<221> NAME/KEY: CDS
<222> LOCATION: (1)...(378)

<400> SEQUENCE: 52

```
atg gaa acc cca gcg cag ctt ctc ttc ctc ctg cta ctc tgg ctc cca      48
Met Glu Thr Pro Ala Gln Leu Leu Phe Leu Leu Leu Leu Trp Leu Pro
1               5                   10                  15 gat acc acc gga gaa att gtg ttg acg cag tct cca ggc acc ctg tct      96
Asp Thr Thr Gly Glu Ile Val Leu Thr Gln Ser Pro Gly Thr Leu Ser
                20                  25                  30 ttg tct cca ggg gaa aga gcc acc ctc tcc tgc agg gcc agt cag agt     144
Leu Ser Pro Gly Glu Arg Ala Thr Leu Ser Cys Arg Ala Ser Gln Ser
            35                  40                  45 gtt agc agc agc tac tta gcc tgg tac cag cag aaa cct ggc cag gct     192
Val Ser Ser Ser Tyr Leu Ala Trp Tyr Gln Gln Lys Pro Gly Gln Ala
        50                  55                  60
```

```
ccc agg ctc ctc atc tat ggt gca tcc agc agg gcc act ggc atc cca         240
Pro Arg Leu Leu Ile Tyr Gly Ala Ser Ser Arg Ala Thr Gly Ile Pro
65                  70                  75                  80 gac agg ttc agt ggc agt ggg tct ggg aca gac ttc act ctc acc atc         288
Asp Arg Phe Ser Gly Ser Gly Ser Gly Thr Asp Phe Thr Leu Thr Ile
                85                  90                  95 agc aga ctg gag cct gaa gat ttt gca gtg tat tac tgt cag cag tat         336
Ser Arg Leu Glu Pro Glu Asp Phe Ala Val Tyr Tyr Cys Gln Gln Tyr
            100                 105                 110 ggt agc tgg acg ttc ggc caa ggg acc aag gtg gaa atc aaa                 378
Gly Ser Trp Thr Phe Gly Gln Gly Thr Lys Val Glu Ile Lys
        115                 120                 125
```

<210> SEQ ID NO 53
<211> LENGTH: 126
<212> TYPE: PRT
<213> ORGANISM: Homo sapiens

<400> SEQUENCE: 53

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Ser Ser Ser Tyr Leu Ala Trp Tyr Gln Gln Lys Pro Gly Gln Ala
        50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Trp Thr Phe Gly Gln Gly Thr Lys Val Glu Ile Lys
        115                 120                 125
```

<210> SEQ ID NO 54
<211> LENGTH: 36
<212> TYPE: DNA
<213> ORGANISM: Homo sapiens
<220> FEATURE:
<221> NAME/KEY: CDS
<222> LOCATION: (1)...(36)

<400> SEQUENCE: 54

```
agg gcc agt cag agt gtt agc agc agc tac tta gcc                         36
Arg Ala Ser Gln Ser Val Ser Ser Ser Tyr Leu Ala
1               5                   10
```

<210> SEQ ID NO 55
<211> LENGTH: 12
<212> TYPE: PRT
<213> ORGANISM: Homo sapiens

<400> SEQUENCE: 55

```
Arg Ala Ser Gln Ser Val Ser Ser Ser Tyr Leu Ala
1               5                   10
```

<210> SEQ ID NO 56
<211> LENGTH: 21
<212> TYPE: DNA
<213> ORGANISM: Homo sapiens

```
<220> FEATURE:
<221> NAME/KEY: CDS
<222> LOCATION: (1)...(21)

<400> SEQUENCE: 56 ggt gca tcc agc agg gcc act                                           21
Gly Ala Ser Ser Arg Ala Thr
 1               5

<210> SEQ ID NO 57
<211> LENGTH: 7
<212> TYPE: PRT
<213> ORGANISM: Homo sapiens

<400> SEQUENCE: 57

Gly Ala Ser Ser Arg Ala Thr
 1               5

<210> SEQ ID NO 58
<211> LENGTH: 21
<212> TYPE: DNA
<213> ORGANISM: Homo sapiens
<220> FEATURE:
<221> NAME/KEY: CDS
<222> LOCATION: (1)...(21)

<400> SEQUENCE: 58 cag cag tat ggt agc tgg acg                                           21
Gln Gln Tyr Gly Ser Trp Thr
 1               5

<210> SEQ ID NO 59
<211> LENGTH: 7
<212> TYPE: PRT
<213> ORGANISM: Homo sapiens

<400> SEQUENCE: 59

Gln Gln Tyr Gly Ser Trp Thr
 1               5

<210> SEQ ID NO 60
<211> LENGTH: 417
<212> TYPE: DNA
<213> ORGANISM: Homo sapiens
<220> FEATURE:
<221> NAME/KEY: CDS
<222> LOCATION: (1)...(417)

<400> SEQUENCE: 60 atg gaa ctg ggg ctc cgc tgg gtt ttc ctt gtt gct att tta gaa ggt       48
Met Glu Leu Gly Leu Arg Trp Val Phe Leu Val Ala Ile Leu Glu Gly
 1               5                  10                  15 gtc cag tgt gag gtg cag ctg gtg gag tct ggg gga ggc ctg gtc aag       96
Val Gln Cys Glu Val Gln Leu Val Glu Ser Gly Gly Gly Leu Val Lys
                 20                  25                  30 cct ggg ggg tcc ctg aga ctc tcc tgt gca gcc tct gga ttc atc ttc      144
Pro Gly Gly Ser Leu Arg Leu Ser Cys Ala Ala Ser Gly Phe Ile Phe
             35                  40                  45 agt agc tat agc atg aac tgg gtc cgc cag gct cca ggg aag ggg ctg      192
Ser Ser Tyr Ser Met Asn Trp Val Arg Gln Ala Pro Gly Lys Gly Leu
         50                  55                  60 gag tgg gtc tca tcc att act agt ggt agt tat tac ata cac tac gca      240
Glu Trp Val Ser Ser Ile Thr Ser Gly Ser Tyr Tyr Ile His Tyr Ala
 65                  70                  75                  80
```

```
gac tca gtg aag ggc cga ttc acc atc tcc aga gac aac gcc aag aac    288
Asp Ser Val Lys Gly Arg Phe Thr Ile Ser Arg Asp Asn Ala Lys Asn
            85                  90                  95 tca ctg tat ctg caa atg aac agc ctg aga gcc gag gac acg gct gtg    336
Ser Leu Tyr Leu Gln Met Asn Ser Leu Arg Ala Glu Asp Thr Ala Val
        100                 105                 110 tat tac tgt gtg aga gag aga gga tgg ggc tac tac ggt atg gac gtc    384
Tyr Tyr Cys Val Arg Glu Arg Gly Trp Gly Tyr Tyr Gly Met Asp Val
            115                 120                 125 tgg ggc caa ggg acc acg gtc acc gtc tcc tca                        417
Trp Gly Gln Gly Thr Thr Val Thr Val Ser Ser
        130                 135
```

<210> SEQ ID NO 61
<211> LENGTH: 139
<212> TYPE: PRT
<213> ORGANISM: Homo sapiens

<400> SEQUENCE: 61

```
Met Glu Leu Gly Leu Arg Trp Val Phe Leu Val Ala Ile Leu Glu Gly
 1               5                  10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Ile Phe
        35                  40                  45

Ser Ser Tyr Ser Met Asn Trp Val Arg Gln Ala Pro Gly Lys Gly Leu
    50                  55                  60

Glu Trp Val Ser Ser Ile Thr Ser Gly Ser Tyr Tyr Ile His Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Val Arg Glu Arg Gly Trp Gly Tyr Tyr Gly Met Asp Val
        115                 120                 125

Trp Gly Gln Gly Thr Thr Val Thr Val Ser Ser
    130                 135
```

<210> SEQ ID NO 62
<211> LENGTH: 15
<212> TYPE: DNA
<213> ORGANISM: Homo sapiens
<220> FEATURE:
<221> NAME/KEY: CDS
<222> LOCATION: (1)...(15)

<400> SEQUENCE: 62

```
agc tat agc atg aac                                                 15
Ser Tyr Ser Met Asn
 1               5
```

<210> SEQ ID NO 63
<211> LENGTH: 5
<212> TYPE: PRT
<213> ORGANISM: Homo sapiens

<400> SEQUENCE: 63

```
Ser Tyr Ser Met Asn
 1               5
```

```
<210> SEQ ID NO 64
<211> LENGTH: 51
<212> TYPE: DNA
<213> ORGANISM: Homo sapiens
<220> FEATURE:
<221> NAME/KEY: CDS
<222> LOCATION: (1)...(51)

<400> SEQUENCE: 64 tcc att act agt ggt agt tat tac ata cac tac gca gac tca gtg aag      48
Ser Ile Thr Ser Gly Ser Tyr Tyr Ile His Tyr Ala Asp Ser Val Lys
1               5                   10                  15 ggc                                                                  51
Gly

<210> SEQ ID NO 65
<211> LENGTH: 17
<212> TYPE: PRT
<213> ORGANISM: Homo sapiens

<400> SEQUENCE: 65

Ser Ile Thr Ser Gly Ser Tyr Tyr Ile His Tyr Ala Asp Ser Val Lys
1               5                   10                  15

Gly

<210> SEQ ID NO 66
<211> LENGTH: 33
<212> TYPE: DNA
<213> ORGANISM: Homo sapiens
<220> FEATURE:
<221> NAME/KEY: CDS
<222> LOCATION: (1)...(33)

<400> SEQUENCE: 66 gag aga gga tgg ggc tac tac ggt atg gac gtc                         33
Glu Arg Gly Trp Gly Tyr Tyr Gly Met Asp Val
1               5                   10

<210> SEQ ID NO 67
<211> LENGTH: 11
<212> TYPE: PRT
<213> ORGANISM: Homo sapiens

<400> SEQUENCE: 67

Glu Arg Gly Trp Gly Tyr Tyr Gly Met Asp Val
1               5                   10

<210> SEQ ID NO 68
<211> LENGTH: 387
<212> TYPE: DNA
<213> ORGANISM: Homo sapiens
<220> FEATURE:
<221> NAME/KEY: CDS
<222> LOCATION: (1)...(387)

<400> SEQUENCE: 68 atg gac atg agg gtc ccc gct cag ctc ctg ggg ctt ctg ctg ctc tgg      48
Met Asp Met Arg Val Pro Ala Gln Leu Leu Gly Leu Leu Leu Leu Trp
1               5                   10                  15 ctc cca ggt gcc aga tgt gcc atc cag ttg acc cag tct cca tcc tcc      96
Leu Pro Gly Ala Arg Cys Ala Ile Gln Leu Thr Gln Ser Pro Ser Ser
                20                  25                  30 ctg tct gca tct gtt gga gac aga gtc acc atc act tgc cgg gca agt     144
Leu Ser Ala Ser Val Gly Asp Arg Val Thr Ile Thr Cys Arg Ala Ser
            35                  40                  45
```

-continued

| | |
|---|---|
| cag gac att gac agt gct tta gcc tgg tat cag cag aaa cca ggg aaa<br>Gln Asp Ile Asp Ser Ala Leu Ala Trp Tyr Gln Gln Lys Pro Gly Lys<br>  50                         55                         60 | 192 |
| gct cct aag atc ctg atc cat gat gcc tcc agt ttg gaa agt ggg gtc<br>Ala Pro Lys Ile Leu Ile His Asp Ala Ser Ser Leu Glu Ser Gly Val<br>65                        70                        75                       80 | 240 |
| cca tca agg ttc agc ggc agt gga tct ggg aca gat ttc act ctc acc<br>Pro Ser Arg Phe Ser Gly Ser Gly Ser Gly Thr Asp Phe Thr Leu Thr<br>                  85                        90                       95 | 288 |
| atc agc agc ctg cag cct gaa gat ttt gca act tat tac tgt caa cag<br>Ile Ser Ser Leu Gln Pro Glu Asp Phe Ala Thr Tyr Tyr Cys Gln Gln<br>              100                    105                    110 | 336 |
| ttt aat agt tac ccg tac act ttt ggc cag ggg acc aag ctg gag atc<br>Phe Asn Ser Tyr Pro Tyr Thr Phe Gly Gln Gly Thr Lys Leu Glu Ile<br>              115                    120                    125 | 384 |
| aaa<br>Lys | 387 |

<210> SEQ ID NO 69
<211> LENGTH: 129
<212> TYPE: PRT
<213> ORGANISM: Homo sapiens

<400> SEQUENCE: 69

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Asp Ser Ala Leu Ala Trp Tyr Gln Gln Lys Pro Gly Lys
    50                  55                  60

Ala Pro Lys Ile Leu Ile His Asp Ala Ser Ser Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Tyr Thr Phe Gly Gln Gly Thr Lys Leu Glu Ile
        115                 120                 125

Lys

<210> SEQ ID NO 70
<211> LENGTH: 33
<212> TYPE: DNA
<213> ORGANISM: Homo sapiens
<220> FEATURE:
<221> NAME/KEY: CDS
<222> LOCATION: (1)...(33)

<400> SEQUENCE: 70

| | |
|---|---|
| cgg gca agt cag gac att gac agt gct tta gcc<br>Arg Ala Ser Gln Asp Ile Asp Ser Ala Leu Ala<br>1                    5                    10 | 33 |

<210> SEQ ID NO 71
<211> LENGTH: 11
<212> TYPE: PRT
<213> ORGANISM: Homo sapiens

<400> SEQUENCE: 71

Arg Ala Ser Gln Asp Ile Asp Ser Ala Leu Ala
1               5                   10

<210> SEQ ID NO 72
<211> LENGTH: 21
<212> TYPE: DNA
<213> ORGANISM: Homo sapiens
<220> FEATURE:
<221> NAME/KEY: CDS
<222> LOCATION: (1)...(21)

<400> SEQUENCE: 72 gat gcc tcc agt ttg gaa agt                                    21
Asp Ala Ser Ser Leu Glu Ser
1               5

<210> SEQ ID NO 73
<211> LENGTH: 7
<212> TYPE: PRT
<213> ORGANISM: Homo sapiens

<400> SEQUENCE: 73

Asp Ala Ser Ser Leu Glu Ser
1               5

<210> SEQ ID NO 74
<211> LENGTH: 27
<212> TYPE: DNA
<213> ORGANISM: Homo sapiens
<220> FEATURE:
<221> NAME/KEY: CDS
<222> LOCATION: (1)...(27)

<400> SEQUENCE: 74 caa cag ttt aat agt tac ccg tac act                            27
Gln Gln Phe Asn Ser Tyr Pro Tyr Thr
1               5

<210> SEQ ID NO 75
<211> LENGTH: 9
<212> TYPE: PRT
<213> ORGANISM: Homo sapiens

<400> SEQUENCE: 75

Gln Gln Phe Asn Ser Tyr Pro Tyr Thr
1               5

<210> SEQ ID NO 76
<211> LENGTH: 408
<212> TYPE: DNA
<213> ORGANISM: Homo sapiens
<220> FEATURE:
<221> NAME/KEY: CDS
<222> LOCATION: (1)...(408)

<400> SEQUENCE: 76 atg aaa cat ctg tgg ttc ttc ctt ctc ctg gtg gca gct ccc aga tgg    48
Met Lys His Leu Trp Phe Phe Leu Leu Leu Val Ala Ala Pro Arg Trp
1               5                   10                  15 gtc ctg tcc cag gta cag ctg cag gag tcg ggc cca gga ctg gtg aag    96
Val Leu Ser Gln Val Gln Leu Gln Glu Ser Gly Pro Gly Leu Val Lys
                20                  25                  30 cct tcg gag acc ctg tcc ctc acc tgc act gtc tct ggt ggc tcc atc   144
Pro Ser Glu Thr Leu Ser Leu Thr Cys Thr Val Ser Gly Gly Ser Ile
            35                  40                  45

```
agt agt gac ttc tgg ggc tgg atc cgg cag ccc cca ggg aag gga ctg     192
Ser Ser Asp Phe Trp Gly Trp Ile Arg Gln Pro Pro Gly Lys Gly Leu
    50                  55                  60 gag tgg att gga tat atc tct tcc cgt ggg agc acc aac tac aac ccc     240
Glu Trp Ile Gly Tyr Ile Ser Ser Arg Gly Ser Thr Asn Tyr Asn Pro
65                  70                  75                  80 tcc ctc aag agg cga gtc acc ata tca gtc gac acg tcc agg aac cag     288
Ser Leu Lys Arg Arg Val Thr Ile Ser Val Asp Thr Ser Arg Asn Gln
                85                  90                  95 ttc tcc ctg aag ctg agc tct gtg acc gct gcg gac acg gcc gtg tat     336
Phe Ser Leu Lys Leu Ser Ser Val Thr Ala Ala Asp Thr Ala Val Tyr
            100                 105                 110 tac tgt gcg aga tct gcg gga gta acg gat ttt gac ttc tgg ggc cag     384
Tyr Cys Ala Arg Ser Ala Gly Val Thr Asp Phe Asp Phe Trp Gly Gln
        115                 120                 125 gga acc ctg gtc acc gtc tcc tca                                     408
Gly Thr Leu Val Thr Val Ser Ser
    130                 135

<210> SEQ ID NO 77
<211> LENGTH: 136
<212> TYPE: PRT
<213> ORGANISM: Homo sapiens

<400> SEQUENCE: 77

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Asp Phe Trp Gly Trp Ile Arg Gln Pro Pro Gly Lys Gly Leu
    50                  55                  60

Glu Trp Ile Gly Tyr Ile Ser Ser Arg Gly Ser Thr Asn Tyr Asn Pro
65                  70                  75                  80

Ser Leu Lys Arg Arg Val Thr Ile Ser Val Asp Thr Ser Arg Asn Gln
                85                  90                  95

Phe Ser Leu Lys Leu Ser Ser Val Thr Ala Ala Asp Thr Ala Val Tyr
            100                 105                 110

Tyr Cys Ala Arg Ser Ala Gly Val Thr Asp Phe Asp Phe Trp Gly Gln
        115                 120                 125

Gly Thr Leu Val Thr Val Ser Ser
    130                 135

<210> SEQ ID NO 78
<211> LENGTH: 15
<212> TYPE: DNA
<213> ORGANISM: Homo sapiens
<220> FEATURE:
<221> NAME/KEY: CDS
<222> LOCATION: (1)...(15)

<400> SEQUENCE: 78 agt gac ttc tgg ggc                                                  15
Ser Asp Phe Trp Gly
1               5

<210> SEQ ID NO 79
<211> LENGTH: 5
<212> TYPE: PRT
<213> ORGANISM: Homo sapiens
```

-continued

<400> SEQUENCE: 79

Ser Asp Phe Trp Gly
1               5

<210> SEQ ID NO 80
<211> LENGTH: 49
<212> TYPE: DNA
<213> ORGANISM: Homo sapiens
<220> FEATURE:
<221> NAME/KEY: CDS
<222> LOCATION: (1)...(49)

<400> SEQUENCE: 80 tat atc tct tcc cgt ggg agc acc aac tac aac ccc tcc ctc aag agg    48
Tyr Ile Ser Ser Arg Gly Ser Thr Asn Tyr Asn Pro Ser Leu Lys Arg
1               5                   10                  15 c                                                                  49

<210> SEQ ID NO 81
<211> LENGTH: 16
<212> TYPE: PRT
<213> ORGANISM: Homo sapiens

<400> SEQUENCE: 81

Tyr Ile Ser Ser Arg Gly Ser Thr Asn Tyr Asn Pro Ser Leu Lys Arg
1               5                   10                  15

<210> SEQ ID NO 82
<211> LENGTH: 27
<212> TYPE: DNA
<213> ORGANISM: Homo sapiens
<220> FEATURE:
<221> NAME/KEY: CDS
<222> LOCATION: (1)...(27)

<400> SEQUENCE: 82 tct gcg gga gta acg gat ttt gac ttc                                27
Ser Ala Gly Val Thr Asp Phe Asp Phe
1               5

<210> SEQ ID NO 83
<211> LENGTH: 9
<212> TYPE: PRT
<213> ORGANISM: Homo sapiens

<400> SEQUENCE: 83

Ser Ala Gly Val Thr Asp Phe Asp Phe
1               5

<210> SEQ ID NO 84
<211> LENGTH: 387
<212> TYPE: DNA
<213> ORGANISM: Homo sapiens
<220> FEATURE:
<221> NAME/KEY: CDS
<222> LOCATION: (1)...(387)

<400> SEQUENCE: 84 atg gac atg atg gtc ccc gct cag ctc ctg ggg ctc ctg ctg ctc tgg    48
Met Asp Met Met Val Pro Ala Gln Leu Leu Gly Leu Leu Leu Leu Trp
1               5                   10                  15 ttc cca ggt tcc aga tgc gac atc cag atg acc cag tct cca tct tcc    96
Phe Pro Gly Ser Arg Cys Asp Ile Gln Met Thr Gln Ser Pro Ser Ser
            20                  25                  30

```
gtg tct gca tct gta gga gac aga gtc acc atc act tgt cgg gcg agt      144
Val Ser Ala Ser Val Gly Asp Arg Val Thr Ile Thr Cys Arg Ala Ser
        35                  40                  45 cag ggt att agc agc tgg tta gcc tgg tat cag cat aaa cca ggg aaa      192
Gln Gly Ile Ser Ser Trp Leu Ala Trp Tyr Gln His Lys Pro Gly Lys
 50                  55                  60 gcc cct aag ctc ctg atc tat gtt gca tcc agt ttg caa agt ggg gtc      240
Ala Pro Lys Leu Leu Ile Tyr Val Ala Ser Ser Leu Gln Ser Gly Val
 65                  70                  75                  80 cca tca agg ttc agc ggc agt gga tct ggg aca gat ttc act ctc acc      288
Pro Ser Arg Phe Ser Gly Ser Gly Ser Gly Thr Asp Phe Thr Leu Thr
                 85                  90                  95 atc agc agc ctg cag cct gaa gat ttt gca act tac tat tgt caa cag      336
Ile Ser Ser Leu Gln Pro Glu Asp Phe Ala Thr Tyr Tyr Cys Gln Gln
            100                 105                 110 gct aat agt ttc cct ctc act ttc ggc gga ggg acc aag gtg gag atc      384
Ala Asn Ser Phe Pro Leu Thr Phe Gly Gly Gly Thr Lys Val Glu Ile
             115                 120                 125 aaa                                                                   387
Lys

<210> SEQ ID NO 85
<211> LENGTH: 129
<212> TYPE: PRT
<213> ORGANISM: Homo sapiens

<400> SEQUENCE: 85

Met Asp Met Met Val Pro Ala Gln Leu Leu Gly Leu Leu Leu Leu Trp
 1               5                  10                  15

Phe Pro Gly Ser Arg Cys Asp Ile Gln Met Thr Gln Ser Pro Ser Ser
                 20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln His Lys Pro Gly Lys
 50                  55                  60

Ala Pro Lys Leu Leu Ile Tyr Val Ala Ser Ser Leu Gln Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Ala Asn Ser Phe Pro Leu Thr Phe Gly Gly Gly Thr Lys Val Glu Ile
             115                 120                 125

Lys

<210> SEQ ID NO 86
<211> LENGTH: 33
<212> TYPE: DNA
<213> ORGANISM: Homo sapiens
<220> FEATURE:
<221> NAME/KEY: CDS
<222> LOCATION: (1)...(33)

<400> SEQUENCE: 86 cgg gcg agt cag ggt att agc agc tgg tta gcc                           33
Arg Ala Ser Gln Gly Ile Ser Ser Trp Leu Ala
 1               5                  10
```

```
<210> SEQ ID NO 87
<211> LENGTH: 11
<212> TYPE: PRT
<213> ORGANISM: Homo sapiens

<400> SEQUENCE: 87

Arg Ala Ser Gln Gly Ile Ser Ser Trp Leu Ala
 1               5                  10

<210> SEQ ID NO 88
<211> LENGTH: 21
<212> TYPE: DNA
<213> ORGANISM: Homo sapiens
<220> FEATURE:
<221> NAME/KEY: CDS
<222> LOCATION: (1)...(21)

<400> SEQUENCE: 88 gtt gca tcc agt ttg caa agt                                       21
Val Ala Ser Ser Leu Gln Ser
 1               5

<210> SEQ ID NO 89
<211> LENGTH: 7
<212> TYPE: PRT
<213> ORGANISM: Homo sapiens

<400> SEQUENCE: 89

Val Ala Ser Ser Leu Gln Ser
 1               5

<210> SEQ ID NO 90
<211> LENGTH: 27
<212> TYPE: DNA
<213> ORGANISM: Homo sapiens
<220> FEATURE:
<221> NAME/KEY: CDS
<222> LOCATION: (1)...(27)

<400> SEQUENCE: 90 caa cag gct aat agt ttc cct ctc act                               27
Gln Gln Ala Asn Ser Phe Pro Leu Thr
 1               5

<210> SEQ ID NO 91
<211> LENGTH: 9
<212> TYPE: PRT
<213> ORGANISM: Homo sapiens

<400> SEQUENCE: 91

Gln Gln Ala Asn Ser Phe Pro Leu Thr
 1               5

<210> SEQ ID NO 92
<211> LENGTH: 153
<212> TYPE: PRT
<213> ORGANISM: Homo sapiens

<400> SEQUENCE: 92

Met Tyr Arg Met Gln Leu Leu Ser Cys Ile Ala Leu Ser Leu Ala Leu
 1               5                  10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45
```

Asn Asn Tyr Lys Asn Pro Lys Leu Thr Arg Met Leu Thr Phe Lys Phe
            50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 93
<211> LENGTH: 153
<212> TYPE: PRT
<213> ORGANISM: Homo sapiens

<400> SEQUENCE: 93

Met Gly Leu Thr Ser Gln Leu Leu Pro Pro Leu Phe Phe Leu Leu Ala
 1               5                  10                  15

Cys Ala Gly Asn Phe Val His Gly His Lys Cys Asp Ile Thr Leu Gln
                20                  25                  30

Glu Ile Ile Lys Thr Leu Asn Ser Leu Thr Glu Gln Lys Thr Leu Cys
            35                  40                  45

Thr Glu Leu Thr Val Thr Asp Ile Phe Ala Ala Ser Lys Asn Thr Thr
 50                  55                  60

Glu Lys Glu Thr Phe Cys Arg Ala Ala Thr Val Leu Arg Gln Phe Tyr
 65                  70                  75                  80

Ser His His Glu Lys Asp Thr Arg Cys Leu Gly Ala Thr Ala Gln Gln
                 85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
            115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 94
<211> LENGTH: 162
<212> TYPE: PRT
<213> ORGANISM: Homo sapiens

<400> SEQUENCE: 94

Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
 50                  55                  60

```
Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser
```

<210> SEQ ID NO 95
<211> LENGTH: 177
<212> TYPE: PRT
<213> ORGANISM: Homo sapiens

<400> SEQUENCE: 95

```
Met Phe His Val Ser Phe Arg Tyr Ile Phe Gly Leu Pro Pro Leu Ile
  1               5                  10                  15

Leu Val Leu Leu Pro Val Ala Ser Ser Asp Cys Asp Ile Glu Gly Lys
             20                  25                  30

Asp Gly Lys Gln Tyr Glu Ser Val Leu Met Val Ser Ile Asp Gln Leu
         35                  40                  45

Leu Asp Ser Met Lys Glu Ile Gly Ser Asn Cys Leu Asn Asn Glu Phe
 50                  55                  60

Asn Phe Phe Lys Arg His Ile Cys Asp Ala Asn Lys Glu Gly Met Phe
 65                  70                  75                  80

Leu Phe Arg Ala Ala Arg Lys Leu Arg Gln Phe Leu Lys Met Asn Ser
                 85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

<210> SEQ ID NO 96
<211> LENGTH: 144
<212> TYPE: PRT
<213> ORGANISM: Homo sapiens

<400> SEQUENCE: 96

```
Met Leu Leu Ala Met Val Leu Thr Ser Ala Leu Leu Leu Cys Ser Val
  1               5                  10                  15

Ala Gly Gln Gly Cys Pro Thr Leu Ala Gly Ile Leu Asp Ile Asn Phe
             20                  25                  30
```

-continued

```
Leu Ile Asn Lys Met Gln Glu Asp Pro Ala Ser Lys Cys His Cys Ser
        35                  40                  45

Ala Asn Val Thr Ser Cys Leu Cys Leu Gly Ile Pro Ser Asp Asn Cys
 50                  55                  60

Thr Arg Pro Cys Phe Ser Glu Arg Leu Ser Gln Met Thr Asn Thr Thr
 65                  70                  75                  80

Met Gln Thr Arg Tyr Pro Leu Ile Phe Ser Arg Val Lys Lys Ser Val
                 85                  90                  95

Glu Val Leu Lys Asn Asn Lys Cys Pro Tyr Phe Ser Cys Glu Gln Pro
                100                 105                 110

Cys Asn Gln Thr Thr Ala Gly Asn Ala Leu Thr Phe Leu Lys Ser Leu
            115                 120                 125

Leu Glu Ile Phe Gln Lys Glu Lys Met Arg Gly Met Arg Gly Lys Ile
        130                 135                 140

<210> SEQ ID NO 97
<211> LENGTH: 146
<212> TYPE: PRT
<213> ORGANISM: Rattus norvegicus

<400> SEQUENCE: 97

Met Glu Arg Thr Leu Val Cys Leu Ile Leu Ile Phe Leu Gly Thr Val
 1               5                  10                  15

Ala His Lys Ser Ser Pro Gln Arg Pro Asp His Leu Leu Ile Arg Leu
                20                  25                  30

Arg His Leu Met Asp Ile Val Glu Gln Leu Lys Ile Tyr Glu Asn Asp
            35                  40                  45

Leu Asp Pro Glu Leu Leu Thr Ala Pro Gln Asp Val Lys Gly Gln Cys
 50                  55                  60

Glu His Glu Ala Phe Ala Cys Phe Gln Lys Ala Lys Leu Lys Pro Ser
 65                  70                  75                  80

Asn Thr Gly Asn Asn Lys Thr Phe Ile Asn Asp Leu Leu Ala Gln Leu
                85                  90                  95

Arg Arg Arg Leu Pro Ala Lys Arg Thr Gly Asn Lys Gln Arg His Met
                100                 105                 110

Ala Lys Cys Pro Ser Cys Asp Leu Tyr Glu Lys Lys Thr Pro Lys Glu
            115                 120                 125

Phe Leu Glu Arg Leu Lys Trp Leu Leu Gln Lys Met Ile His Gln His
        130                 135                 140

Leu Ser
145
```

ANTI-HUMAN IL-21 MONOCLONAL ANTIBODIES

REFERENCE TO RELATED APPLICATIONS

This application is a divisional of U.S. patent application Ser. No. 12/330,334, filed Dec. 8, 2008 now U.S. Pat. No. 7,883,700; which claims the benefit of U.S. Provisional Application Ser. No. 61/012,329, filed Dec. 7, 2007, which is herein incorporated by reference.

BACKGROUND OF THE INVENTION

The immune system is the body's primary defense against diseases caused by pathogens, namely bacteria, viruses, fungi etc, as well as against diseases caused by abnormal growth of the body's own cells and tissues (i.e. cancerous tumors). Normally, the immune system is able to distinguish between the body's normal cells or "self" and foreign pathogens or abnormal cells or "non-self". The processes by which the immune system refrains from reacting to one's own body is called tolerance. Sometimes, the immune system loses the ability to recognize "self" as normal and the subsequent response directed against the tissue or cells, results in loss of tolerance, a state of autoimmunity. The pathologies resulting from autoimmunity often have serious clinical consequences and are one of the major health problems in the world, especially in developed nations.

IL-21 is a potent immunomodulatory four-α-helical bundle type I cytokine that binds to a heterodimeric receptor composed of IL-21R and the common gamma chain (reviewed by Spolski and Leonard, *Annu Rev Immunol*. Nov. 8; 2007). IL-21 is produced by NK-T and CD4+ T cells (including pro-inflammatory Th17 cells and follicular helper $T_{FH}$ cells that are important for germinal center responses) and has pleiotropic effects on both innate and adaptive immune responses, including enhanced proliferation of B and T cells, increased cytotoxicity of CD8+ T cells and natural killer (NK) cells, differentiation of B cells into immunoglobulin-secreting plasma cells, and regulation of the Th17 cell lineage (see below). IL-21 can also inhibit the antigen-presentation function of dendritic cells and can induce apoptosis in B cells and NK cells under certain conditions. IL-21 has potent anti-tumor activity, but has also been associated with the development of various autoimmune diseases, including systemic lupus erythematosus (SLE), rheumatoid arthritis (RA), inflammatory bowel disease (IBD) and psoriasis (reviewed by Spolski and Leonard, *Annu Rev Immunol*. Nov. 8, 2007).

IL-21 has been shown to modulate antibody responses by directly acting on B cells. (Mehta et al., *J. Immunol.*, 170: 4111-4118, 2003; Ozaki et al., *Science*, 298:1630-1634, 2002; Suto et al., *Blood*, 100:4565-4573, 2002). IL-21 can induce the differentiation of naïve human B cells into antibody-secreting plasma cells (Ozaki et al. *J. Immunol.* 173: 5361, 2004; Ettinger et al., *J Immunol.* 175:7867-79, 2005; Ettinger et al, *J Immunol.* 178:2872-82, 2007; Kuchen et al. *J Immunol.* 179:5886-96, 2007) and to stimulate the production of IgE in human B cell (Kobayashi et al. *Human Immunol.* doi:10:1016/j.humimm.2008.10.) In IL-21 or IL-21R deficient animals, fewer antibody-secreting cells are generated from the germinal center reaction and affinity maturation is reduced (Zotos et al., submitted). Extrafollicular antibody forming cells, which are implicated in autoimmunity, require cognate help from a subset of specialized CD4 T cells that secrete IL-21 (Odegard, et al., *JEM* 205(12):2873-2886, 2008).

Generation of antibodies against allogenic MHC is a pivotal phenomenon in transplant rejection. Transplant recipients who develop titres of anti-MHC antibodies (highly sensitized transplant patients) are t risk for chronic rejection and are poor candidates for new grafts due to likelihood of antibody mediated rejection of the new transplant (Smith, et al., *Am J Transplantation* 8: 1-11, 2008). In a rat model of acute renal allograft rejection, IL-21 and IL-21R were uniquely increased in intravascular mononuclear cells of renal allografts but not isografts (Hecker, et al., *Immunobiology*: doi:10.1016/j.imbio. 2008 Apr. 4, (2008)). In human cardiac transplants undergoing rejection, expression levels of IL-21 and IL-21R correlate with the ISHLT rejection grade, and highest expression is present in grades 1R and 2R (Baan, et al., *Transplantation* 83(11): 1485-1492, 2007).

In graft-versus-host-disease (GVHD), the anti-allo response is mediated by uncontrolled activation of T lymphocytes from the graft, which direct an inflammatory response against host tissues. Regulatory T cells (Treg) can modulate this response in animal models. IL-21 has been shown to counteract the regulatory functions of Treg (Clough et al., *J Immunol* 180: 5395-5401, 2008). In mouse models of GVHD, transfer of IL-21 deficient T cells resulted in significantly reduced clinical signs and histological scores and increased survival, compared with WT T cells. Decreased frequency of IFN-gamma secreting T cells and increased Tregs were observed in the colon mucosa. IL-21 blockade using anti-mIL-21 mAb and WT T cell transfer produced similar results (Bucher et al., *Blood* (ASH Annual Meeting Abstracts) 2008 112: Abstract #2342).

It has also recently been shown that IL-21 is both produced by and required for the differentiation of mouse pro-inflammatory Th17 cells (Korn et al. *Nature*. 448:484-487, 2007; Nurieva et al. *Nature* 448:480-483, 2007; Zhou et al., *Nat Immunol*. 8:967-974, 2007; Wei et al. *J Biol Chem*. 282: 34605-34610, 2007). Human Th17 cells also produce IL-21 and studies are ongoing to determine whether IL-21 acts as an autocrine factor for human Th17 cells, as it does for mouse Th17 cells. Ozaki et al. (*J. Immunol*. 173:5361, 2004) demonstrated that IL-21 expression is elevated in lupus-prone BXSB-Yaa mice, a model for systemic lupus erythematosus (SLE), at an age when the early characteristics of autoimmune processes first become evident. Treatment of these BXSB-Yaa mice with a soluble mouse IL-21 receptor (mIL-21R-Fc) partially inhibits various disease parameters, including glomerulonephritis (Bubier et al., *Ann N Y Acad Sci*. 1110:590-601, 2007). Treatment with mIL-21R-Fc has also been shown to be efficacious in another pre-clinical disease model of SLE, the MRL/lpr mouse (Herber et al. *J. Immunol*. 178: 3822-3830, 2007), as well as in the collagen-induced arthritis (CIA) model of rheumatoid arthritis (Young et al., *Arthr Rheum* 56:1152-1163, 2007). Preliminary human data also suggest dysregulation of IL-21 and IL-21R in SLE (Mitoma et al. *Int J Mol Med*. 16:609-615, 2005; Wang et al., *Chinese J. Cell. Mol. Immunol*. 23(11):1041-1042, 2007; Sawalha et al. *Ann Rheum Dis* 67: 458-461, 2008). More recently, Rus et al. data obtained from 24 SLE patients and 15 healthy controls (Nguyen et al., ACR/ARHP Scientific Meeting, 1760/482, 2008 Oct. 24-29 San Francisco, Calif.). Rus et al. showed that 1) IL-21 mRNA expression is significantly increased in CD4+ T cells from lupus patients compared to controls, 2) IL-21 levels are significantly elevated in sera from patients with active compared to inactive SLE or controls, 3) IL-21 enhances CD4+ T cells and CD19+ B cells proliferation in patients and controls in a dose dependent fashion, 4) IL-21 enhances anti-CD40 induced plasma cell differentiation in normal controls and SLE patients, and 5) elevated levels of IL-21 may contribute to proliferation of autoreactive CD4+ T cells and plasma cell differentiation in SLE.

Monteleone et al have demonstrated that IL-21 RNA and protein expression is increased in inflamed but not uninflamed tissue from Crohn's disease (CD) (and, to a lesser degree, ulcerative colitis) patients and that IL-21 production by CD3+ cells from lamina propria mononuclear cells from CD patients is also enhanced (Monteleone et al. *Gastroenterology* 128:687-694, 2005; Monteleone et al. *Gut* 55:1774-1780, 2006; Peluso et al., *J Immunol* 178:732-739, 2007). These authors suggested that IL-21 regulates experimental colitis by modulating the balance between regulatory T cells (Tregs) and Th17 cells (Fantini et al. *Eur. J. Immunol.* 37:3155-3163, 2007). Inhibition of IL-21 in vivo with a soluble IL-21 receptor in either mouse or rat models of colitis leads to significant reductions in clinical signs of colitis (Young et al. US 2006/0039902).

The IL-21 receptor is expressed by NK cells, and NK cells have been shown to be responsive to treatment with IL-21 both in vivo and in vitro. In oncology patients treated with recombinant human IL-21, altered recirculation patterns in lymphocyte subsets including NK cells, and increased expression of markers of NK cell activation and cytolytic effector capacity were observed (Frederiksen, et al., *Cancer Immunol Immunother* 57(10): 1439-1449, 2008). In autoimmune diseases, NK cell activity may play a role in promoting inflammation and associated tissue damage. Tissue homing of NK cells is directed by chemoattractants released at the site of inflammation (Morris and Ley, *Curr Mol Med.*; 4(4):431-8, 2004). Lamina propria NK cells from patients with Crohn's Disease released greater quantities of IFN-γ and TNF-α when stimulated in vitro with IL-21 and IgG, compared with LPNK cells from controls (Liu and Jiu, *Chronic Inflammation of Liver and Gut, Falk Symposium abst. No.* 163, 2008 Mar. 14-15). NK cells are also reported to regulate autoimmunity and transplant rejection through their interactions with dendritic cells (DC), by killing immature or activated DC, and by releasing cytokines that affect the activation state and antigen presentation functions of the DC (Vivier et al., *Nat Immunol* 9(5):503-510, 2008; Laffont et al., *Blood* 112:661-671, 2008). A comparison of peripheral blood mononuclear cells from tolerant and non-tolerant liver allograft recipients showed changes in the transcriptional program of NK cells (Martinez-Llordella et al., *J Clin Invest* 118(8):2845-2857, 2008). Thus, blockade of IL-21 may modulate the activation status of NK cells, reduce their contribution to tissue inflammation in autoimmune diseases, and alter the clinical course of transplant rejection. NK cells are also reported to regulate autoimmunity and transplant rejection through their interactions with dendritic cells (DC), by killing immature or activated DC and by releasing cytokines that affect the activation state and alter antigen presentation functions of the DC. Thus, blockade of IL-21 may modulate the activation of NK cells and reduce their contribution to tissue inflammation in autoimmune diseases.

The present invention provides anti-human IL-21 monoclonal antibodies and methods of using those antibodies that inhibit the symptoms and biological activities that manifest as autoimmune and inflammatory disorders and are associated with IL-21/IL-21 receptor interactions.

BRIEF DESCRIPTION OF THE FIGURES

FIG. 1 is an alignment based on the Kabat numbering system of amino acid residues comprising the variable heavy chain regions of antibodies designated by clone numbers 362.78.1.44 (78), 362.597.3 (597), 362.75.1.1 (75), 366.552.11 (552), 366.328.10 (328), and correspond with SEQ ID NO: 29, SEQ ID NO: 45, SEQ ID NO: 13, SEQ ID NO: 77 and SEQ ID NO: 61, respectively.

FIG. 2 is an alignment based on the Kabat numbering system of amino acid residues comprising the variable light chain region of antibodies designated by clone numbers 362.78.1.44 (78), 362.597.3 (597), 362.75.1.1 (75), 366.552.11 (552), 366.328.10 (328), and correspond with SEQ ID NO: 37, SEQ ID NO: 53, SEQ ID NO: 21, SEQ ID NO: 85 and SEQ ID NO: 69, respectively.

BRIEF DESCRIPTION OF THE INVENTION

Figure 3:
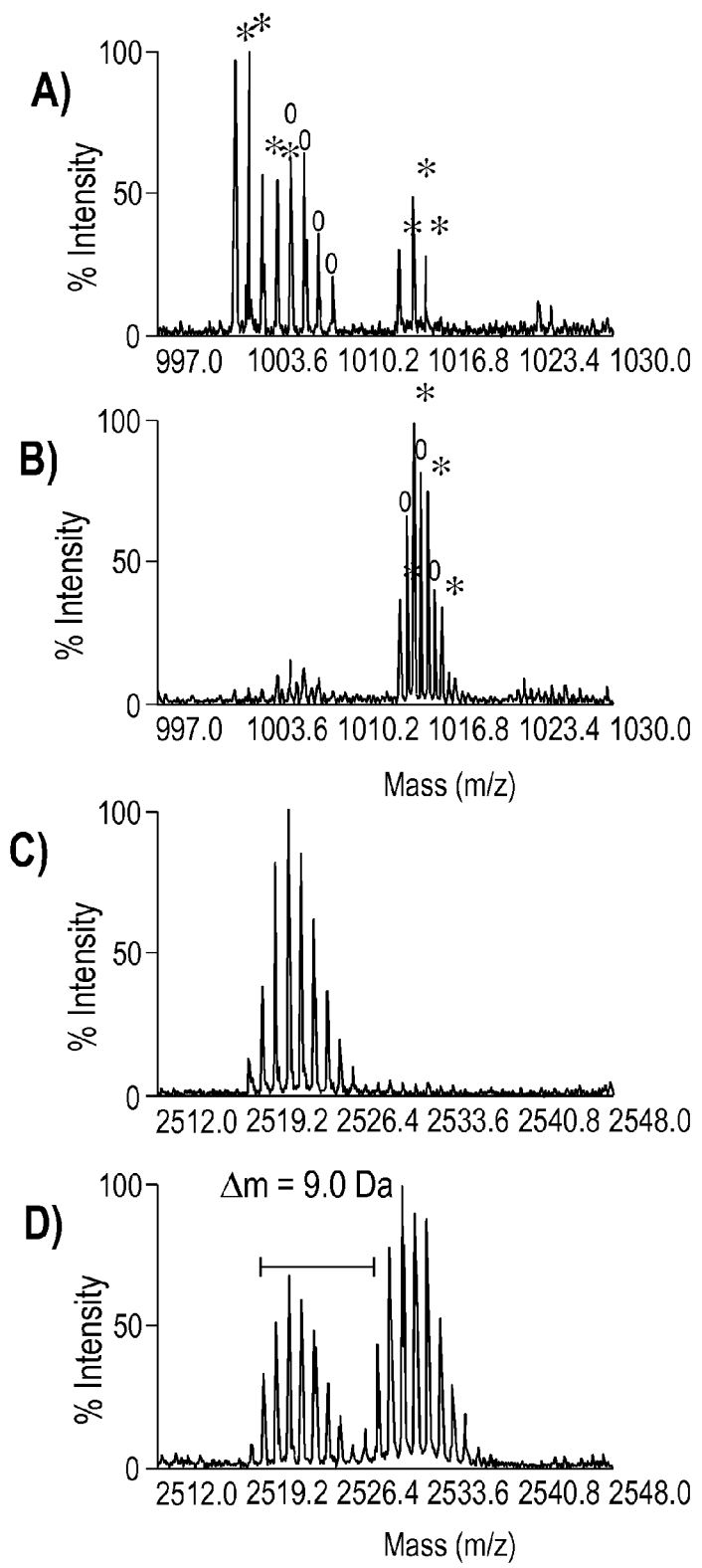
FIG. 3 illustrates MALDI/TOF mass spectra of IL-21 peptide sequence regions obtained from IL-21 alone and the IL-21 immune complex. IL-21 peptide sequences, EKKPPKEF (SEQ ID NO: 2 from residue 129 to 136) (m/z, 1002.5619 Da) and LERFKSLL (SEQ ID NO: 2 from residue 137 to 144) (m/z, 1005.6091 Da) of the free-state of IL-21 (A). Peptide mass shifting due to the retention of amide deuteration in the presence of IL-21 mAb (B). Another IL-21 peptide sequence region, KSLLQKMIHQHLSSRTHGSEDS (SEQ ID NO: 2 from residue 141 to 162) (m/z, 2519.2451) of the free-state of IL-21 (C). A partial peptide mass shifting due to the retention of amide deuteration in the presence of IL-21 mAb (D).

In one aspect, the present invention provides an anti-human IL-21 monoclonal antibody comprising at least 80% identity to amino acid residues 20 to 145 of SEQ ID NO: 29 and at least 80% identity to amino acid residues 21 to 126 of SEQ ID NO: 37. In certain embodiments, the antibodies comprise changes of at least 80% identity that are in the heavy chain variable region CDR1 of SEQ ID NO: 31.

In another aspect, the present invention provides an anti-human IL-21 monoclonal antibody comprising: (a) a heavy chain region comprising: (i) a heavy chain variable region CDR1 comprising SEQ ID NO: 31; (ii) a heavy chain variable region CDR2 comprising SEQ ID NO: 33; and (iii) a heavy chain variable region CDR3 comprising SEQ ID NO: 35; and (b) a light chain region comprising: (i) a light chain variable region CDR1 comprising SEQ ID NO: 39; (ii) a light chain variable region CDR2 comprising SEQ ID NO: 41; and (iii) a light chain variable region CDR3 comprising SEQ ID NO: 43. In certain embodiments, the invention provides an anti-human IL-21 monoclonal antibody comprising amino acids residues 20 to 145 of SEQ ID NO: 29 and amino acid residues 21 to 126 of SEQ ID NO: 37. In other embodiments, the antibody is further comprising amino acid residues 1 to 145 of SEQ ID NO: 29 and amino acid residues 1 to 126 of SEQ ID NO: 37. Another embodiment of the present invention provides a hybridoma designated 362.78.1.44, wherein the hybridoma is deposited with the American Type Culture Collection having the ATCC Patent Deposit Designation PTA-8790, and the invention includes the antibody produced by the hybridoma.

Another aspect of the present invention provides an anti-human IL-21 monoclonal antibody comprising: (a) a heavy chain region comprising: (i) a heavy chain variable region CDR1 comprising SEQ ID NO: 47; (ii) a heavy chain variable region CDR2 comprising SEQ ID NO: 49; and (iii) a heavy chain variable region CDR3 comprising SEQ ID NO: 51; and (b) a light chain region comprising: (i) a light chain variable region CDR1 comprising SEQ ID NO: 55; (ii) a light chain variable region CDR2 comprising SEQ ID NO: 57; and (iii) a light chain variable region CDR3 comprising SEQ ID NO: 59. In certain embodiments, the invention provides an anti-human IL-21 monoclonal antibody comprising amino acid residues 20-145 of SEQ ID NO: 45 and amino acid residues 21 to 126 of SEQ ID NO: 53. In other embodiments, the invention further comprises amino acid residues 1 to 145 of SEQ ID NO: 45 and amino acid residues 21 to 126 of SEQ ID NO: 53. Another embodiment of the present invention provides a hybridoma designated 362.597.3, wherein the hybridoma is deposited with the American Type Culture Collection having the ATCC Patent Deposit Designation PTA-8786 (deposited Nov. 15, 2007, American Type Culture Collection, 10801 University Boulevard., Manassas, Va. 20110-2209), and the invention includes the antibody produced by the hybridoma.

In another aspect, the present invention provides an anti-human IL-21 monoclonal antibody comprising at least 80% identity to amino acid residues 20 to 141 of SEQ ID NO: 13 and at least 80% identity to amino acid residues 21 to 126 of SEQ ID NO: 21. In one embodiment, the invention includes a monoclonal antibody where any amino acid changes are conservative amino acid changes.

In another aspect, the present invention provides an anti-human IL-21 monoclonal antibody comprising: (a) a heavy chain region comprising: (i) a heavy chain variable region CDR1 comprising SEQ ID NO: 15; (ii) a heavy chain variable region CDR2 comprising SEQ ID NO: 17; and (iii) a heavy chain variable region CDR3 comprising SEQ ID NO: 19; and (b) a light chain region comprising: (i) a light chain variable region CDR1 comprising SEQ ID NO: 23; (ii) a light chain variable region CDR2 comprising SEQ ID NO: 25; and (iii) a light chain variable region CDR3 comprising SEQ ID NO: 27. In certain embodiments, the present invention includes an anti-human IL-21 monoclonal antibody comprising amino acid residues 20 to 141 of SEQ ID NO: 13 and amino acid residues 21 to 126 of SEQ ID NO: 21. In another embodiment, the invention is further comprising amino acid residues 1 to 141 of SEQ ID NO: 13 and amino acid residues 1 to 126 of SEQ ID NO: 21. Another embodiment of the present invention provides a hybridoma designated 362.75.1.1, wherein the hybridoma is deposited with the American Type Culture Collection having the ATCC Patent Deposit Designation PTA-8791, and the antibody produced by the hybridoma.

In another aspect, the present invention provides an anti-human IL-21 monoclonal antibody comprising: (a) a heavy chain region comprising: (i) a heavy chain variable region CDR1 comprising SEQ ID NO: 79; (ii) a heavy chain variable region CDR2 comprising SEQ ID NO: 81; and (iii) a heavy chain variable region CDR3 comprising SEQ ID NO: 83; and (b) a light chain region comprising: (i) a light chain variable region CDR1 comprising SEQ ID NO: 87; (ii) a light chain variable region CDR2 comprising SEQ ID NO: 89; and (iii) a light chain variable region CDR3 comprising SEQ ID NO: 91. In one embodiment, the present invention provides an anti-human IL-21 monoclonal antibody comprising amino acids residues 20 to 136 of SEQ ID NO: 77 and amino acid residues 23 to 129 of SEQ ID NO: 85. In another embodiment, the invention is further comprising amino acid residues 1 to 136 of SEQ ID NO: 77 and amino acid residues 1 to 129 of SEQ ID NO: 85. Another embodiment of the present invention provides a hybridoma designated 366.552.11, wherein the hybridoma is deposited with the American Type Culture Collection having the ATCC Patent Deposit Designation PTA-8787, and the antibody produced by the hybridoma.

In another aspect, the present invention provides an anti-human IL-21 monoclonal antibody comprising: (a) a heavy chain region comprising: (i) a heavy chain variable region CDR1 comprising SEQ ID NO: 63; (ii) a heavy chain variable region CDR2 comprising SEQ ID NO: 65; and (iii) a heavy chain variable region CDR3 comprising SEQ ID NO: 67; and (b) a light chain region comprising: (i) a light chain variable region CDR1 comprising SEQ ID NO: 71; (ii) a light chain variable region CDR2 comprising SEQ ID NO: 73; and (iii) a light chain variable region CDR3 comprising SEQ ID NO: 75. In certain embodiments, the present invention provides an anti-human IL-21 monoclonal antibody comprising amino acids residues 20 to 139 of SEQ ID NO: 61 and amino acid residues 23 to 129 of SEQ ID NO: 69. In other embodiments, the present invention is further comprising amino acid residues 1 to 139 of SEQ ID NO: 61 and amino acid residues 1 to 129 of SEQ ID NO: 69. Another embodiment of the present invention provides a hybridoma designated 366.328.10, wherein the hybridoma is deposited with the American Type Culture Collection having the ATCC Patent Deposit Designation PTA-8789 and the antibody produced the hybridoma.

In another aspect, the present invention provides a hybridoma designated 366.345.6.11, wherein the hybridoma is deposited with the American Type Culture Collection having the ATCC Patent Deposit Designation PTA-8788 and the includes the antibody produced by the hybridoma.

In another aspect of the present invention, the present invention provides an isolated monoclonal antibody that binds to a discontinuous epitope comprising at least two regions on an IL-21 protein, wherein the first region consists of at least one amino acid from residue Ile45 to residue Leu56 of SEQ ID NO: 2 and the second region consists at least one amino acid residue Glu129 to residue Leu144 of SEQ ID NO: 2. In one embodiment, the invention provides that the first region consists of between 1 and 12 amino acids from residue Ile45 to residue Leu56 of SEQ ID NO: 2, and the second region consists of between 1 and 16 amino acids from residue Glu129 to residue Leu144 of SEQ ID NO: 2.

In each aspect of the inventions described above, included is an embodiment where the monoclonal antibody further comprises an Fc portion, and another embodiment, wherein the Fc portion is selected the group consisting of IgG1, IgG2 and IgG4 and another embodiment, wherein the Fc portion has reduced effector function.

In another aspect, the present invention provides a method of treating T follicular helper cell-mediated or B cell-mediated diseases in a subject by administering a therapeutic amount of the claimed anti-human IL-21 monoclonal antibodies described herein, wherein the T follicular helper cell-mediated and B cell-mediated diseases are selected from the group consisting of systemic lupus erythematosus, autoimmune hearing loss, Graves' Disease, pemphigus vulgaris, myasthenia gravis, neuromyelitis optica, Goodpasture's syndrome, autoimmune nephritis, cryoglobulinemia, Guillain Bane syndrome, chronic inflammatory demyelinating polyneuropathy (CIDP), autoimmune hemolytic anemia, and idiopathic thrombocytopenic purpura (ITP).

In another aspect, the present invention provides a method of treating TH1 cell-mediated or TH17 cell-mediated diseases in a subject by administering a therapeutic amount of the claimed an anti-human IL-21 monoclonal antibodies described herein, wherein the TH1 cell-mediated or TH17 cell-mediated diseases are selected from the group consisting of psoriasis, spondyloarthropathy, reactive arthritis, enteropathic arthritis, autoimmune myocarditis, Kawasaki disease, celiac disease, uveitis, Behcet's disease, coronary artery disease, chronic obstructive pulmonary disease (COPD), and interstitial lung disease.

In another aspect, the present invention provides a method of treating inflammatory bowel disease (IBD) in a subject by administering a therapeutic amount of the claimed anti-human IL-21 monoclonal antibodies described herein, wherein the inflammatory bowel disease is selected from the group consisting of Crohn's Disease, ulcerative colitis and irritable bowel syndrome.

In another aspect, the present invention provides a method of treating rheumatoid arthritis in a subject by administering a therapeutic amount of the claimed anti-human IL-21 monoclonal antibodies described herein.

In another aspect, the present invention provides a method of treating multiple sclerosis in a subject by administering a therapeutic amount of the claimed anti-human IL-21 monoclonal antibodies described herein.

In another aspect, the present invention provides a method of treating type I diabetes (IDDM) in a subject by administering a therapeutic amount of the claimed anti-human IL-21 monoclonal antibodies.

In another aspect, the present invention provides a method of treating Sjogren's syndrome in a subject by administering a therapeutic amount of the claimed anti-human IL-21 monoclonal antibodies described herein.

In another aspect, the present invention provides a method of treating a transplant subject by administering a therapeutic amount of the claimed anti-human IL-21 monoclonal antibodies described herein, wherein transplant rejection is suppressed, tolerance in the pre-transplant therapeutic regimen is established or alloantibody titers in the subject are reduced.

In another aspect, the present invention provides a method of treating an autoimmune disease in a subject by administering a therapeutic amount of the claimed anti-human IL-21 monoclonal antibodies described herein, wherein the autoimmune disease is selected from the group consisting of pancreatitis, inflammatory muscle disease (polymyositis, dermatomyositis), microscopic polyangiitis, autoimmune aplastic anemia, autoimmune thyroiditis, autoimmune hepatitis, Wegener's syndrome, diverticulosis, ankylosing spondylitis, scleroderma, systemic sclerosis, psoriatic arthritis, osteoarthritis, atopic dermatitis, vitiligoi, graft vs. host disease (GVHD), cutaneous T cell lymphoma (CTCL), glomerulonephritis, IgA nephropathy, highly sensitized transplant patients, anti-phospholipid syndrome, and asthma, and other autoimmune diseases, or other diseases mediated by IL-21 and IL-21 receptor agonists.

In another aspect, the present invention provides a method of treating systemic lupus erythematosus (SLE) in a subject by administering a therapeutic amount of the claimed anti-human IL-21 monoclonal antibodies described herein.

In another aspect, the present invention provides a method of treating psoriasis in a subject by administering a therapeutic amount of the claimed anti-human IL-21 monoclonal antibodies described herein.

DESCRIPTION OF THE INVENTION

The following definitions are provided to facilitate understanding of the inventions described herein.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "antagonist" refers to any compound including a protein, polypeptide, peptide, antibody, antibody fragment, large molecule, or small molecule (less than 10 kD), that decreases the activity, activation or function of another molecule. IL-21 antagonists cause at least one of the following: decreased immune function of NK cells, dendritic cells, T cell subsets and B cell subsets; bind IL-21 such that the interaction of IL-21 protein with its receptor is blocked, inhibited, reduced or neutralized.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. Thus, as used herein, the term "antibody" or "antibody peptide(s)" refers to an intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')$_2$, Fv, and single-chain antibodies, ScFv. "Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide-linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al., *J. Mol. Biol.* 186:651 (1985); Novotny and Haber, *Proc. Natl. Acad. Sci. U.S.A.* 82:4592 (1985)).

The term "chimeric antibody" or "chimeric antibodies" refers to antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant domain from a human antibody, although other mammalian species may be used. Specifically, a chimeric antibody is produced by recombinant DNA technology in which all or part of the hinge and constant regions of an immunoglobulin light chain, heavy chain, or both, have been substituted for the corresponding regions from another animal's immunoglobulin light chain or heavy chain. In this way, the antigen-binding portion of the parent monoclonal antibody is grafted onto the backbone of another species' antibody.

The term "epitope" refers to any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. More specifically, the term "IL-21 epitope" as used herein refers to a portion of the IL-21 polypeptide having antigenic or immunogenic activity in an animal, preferably in a mammal, and most preferably in a mouse or a human. An epitope having immunogenic activity is a portion of a IL-21 polypeptide that elicits an antibody response in an animal. An epitope having antigenic activity is a portion of a IL-21 polypeptide to which an antibody immunospecifically binds as determined by any method well known in the art, for example, by immunoassays. Antigenic epitopes need not necessarily be immunogenic. "Discontinuous epitopes" are conformational epitopes formed from at least two separate regions in the primary sequence of the IL-21 protein. Conformational epitopes lose the ability to specifically bind in the presence of denaturing solvents (e.g. in western blot analyses).

The present invention provides monoclonal antibodies and antibody fragments that specifically bind to IL-21 proteins and polypeptides. Human and mouse IL-21 polypeptides, proteins and polynucleotides encoding the polypeptides are disclosed in Parrish-Novak et al., Nature 408:57-63, 2003; U.S. Pat. Nos. 6,307,024 and 6,686,178; and 7,250,274. Described herein are structural and functional characteristics defining regions (epitopes) of the human IL-21 protein that have been identified as targets for a therapeutic monoclonal antibody. Exemplary human anti-human IL-21 monoclonal antibodies are presented. Certain of these antibodies have the ability to bind native human IL-21, recombinant wildtype human IL-21, a recombinant mutant IL-21 protein and/or peptide regions of human IL-21.

The present invention provides anti-IL-21 antibodies which are useful in therapeutic treatment of autoimmune and inflammatory diseases. For example, anti-IL-21 antibodies are useful in the treatment of psoriasis, pancreatitis, type I diabetes (IDDM), Graves' Disease, inflammatory bowel disease (IBD), Crohn's Disease, ulcerative colitis, irritable bowel syndrome, multiple sclerosis, rheumatoid arthritis, reactive arthritis, enteropathic arthritis, spondyloarthropathy, autoimmune myocarditis, Kawasaki disease, celiac disease, uveitis, Behcet's disease, coronary artery disease, chronic obstructive pulmonary disease (COPD), interstitial lung disease, inflammatory muscle disease (polymyositis, dermatomyositis), microscopic polyangiitis, autoimmune aplastic anemia, autoimmune thyroiditis, autoimmune hepatitis, Wegener's syndrome, diverticulosis, systemic lupus erythematosus, ankylosing spondylitis, scleroderma, systemic sclerosis, psoriatic arthritis, osteoarthritis, atopic dermatitis, vitiligo, graft vs. host disease (GVHD), cutaneous T cell lymphoma (CTCL), Sjogren's syndrome, glomerulonephritis, IgA nephropathy, autoimmune nephritis, pemphigus vulgaris, myasthenia gravis, autoimmune hearing loss, neuromyelitis optica, Goodpasture's syndrome, cryoglobulinemia, Guillain Bane syndrome, chronic inflammatory demyelinating polyneuropathy (CIDP), autoimmune hemolytic anemia, idiopathic thrombocytopenic purpura (ITP), transplant rejection, highly sensitized transplant patients, anti-phospholipid syndrome, allergy, and asthma, and other autoimmune diseases, or other diseases mediated by IL-21 and IL-21 receptor agonists.

Five classes of immunoglobulin, IgG, IgA, IgM, IgD, and IgE, have been identified in higher vertebrates. IgG, IgD, and IgE proteins are characteristically disulfide linked heterotetramers consisting of two identical heavy chains and two identical light chains. Typically, IgM is found as a pentamer of a tetramer, whereas IgA occurs as a dimer of a tetramer. Modifications can be introduced in the immunoglobulin moiety.

IgG comprises the major class as it normally exists as the second most abundant protein found in plasma. In humans, IgG consists of four subclasses, designated IgG1, IgG2, IgG3, and IgG4. Each immunoglobulin heavy chain possesses a constant region that consists of constant region protein domains ($C_H1$, hinge, $C_H2$, and $C_H3$) that are invariant for a given subclass. The heavy chain constant regions of the IgG class are identified with the Greek symbol γ. For example, immunoglobulins of the IgG1 subclass contain a γ1 heavy chain constant region.

The Fc fragment, or Fc domain, consists of the disulfide linked heavy chain hinge regions, $C_H2$, and $C_H3$ domains. In immunoglobulin fusion proteins, Fc domains of the IgG1 subclass are often used as the immunoglobulin moiety, because IgG1 has the longest serum half-life of any of the serum proteins. Lengthy serum half-life can be a desirable protein characteristic for animal studies and potential human therapeutic use. In addition, the IgG1 subclass possesses the strongest ability to carry out antibody mediated effector functions. The primary effector function that may be most useful in an immunoglobulin fusion protein is the ability for an IgG1 antibody to mediate antibody dependent cellular cytotoxicity. On the other hand, this could be an undesirable function for a fusion protein that functions primarily as an antagonist. Several of the specific amino acid residues that are important for antibody constant region-mediated activity in the IgG1 subclass have been identified. Inclusion or exclusion of these specific amino acids therefore allows for inclusion or exclusion of specific immunoglobulin constant region-mediated activity (see, U.S. Pat. Nos. 5,648,260; 5,624,821).

Modified human IgG1 Fc have been generated for creating Fc fusion proteins. For example, Fc4, Fc5, and Fc6 mutations to reduce effector functions mediated by the Fc by reducing FcγRI binding and complement C1q binding are described in U.S. Patent Application 2006-0034852, incorporated by reference herein in its entirety. Specifically, three amino acid substitutions were introduced to reduce FcγRI binding. These are the substitutions at EU index positions 234, 235, and 237. Substitutions at these positions have been shown to reduce binding to FcγRI (Duncan et al., Nature 332:563 (1988)). These amino acid substitutions may also reduce FcγRIIa binding, as well as FcγRIII binding (Sondermann et al., Nature 406:267 (2000); Wines et al., J. Immunol. 164:5313 (2000)). These mutations do not alter binding to FcRn, which promotes long serum half-life by salvaging IgG through an endocytic recycling pathway.

Several groups have described the relevance of EU index positions 330 and 331 in complement C1q binding and subsequent complement fixation (Canfield and Morrison, J. Exp. Med. 173:1483 (1991); Tao et al., J. Exp. Med. 178:661 (1993)). Amino acid substitutions at these positions were introduced in Fc4 to reduce complement fixation. The $C_H3$ domain of Fc4 is identical to that found in the corresponding wild-type polypeptide, except for the stop codon, which was changed from TGA to TAA to eliminate a potential dam methylation site when the cloned DNA is grown in dam plus strains of E. coli. In Fc5, the arginine residue at EU index position 218 is a lysine and the remainder of the Fc5 sequence matches the above description for Fc4.

The present invention also includes genetically altered antibodies that are functionally equivalent to the above-described antibodies. Modified antibodies providing improved stability and/or therapeutic efficacy are preferred. Examples of modified antibodies include those with conservative substitutions of amino acid residues, and one or more deletions or additions of amino acids which do not significantly deleteriously alter the antigen binding utility. Substitutions can range from changing or modifying one or more amino acid residues to complete redesign of a region as long as the therapeutic utility is maintained. Antibodies of the present invention can be can be modified post-translationally (e.g., acetylation, and phosphorylation) or can be modified synthetically (e.g., the attachment of a labeling group).

Antibodies of the present invention may be described or specified in terms of the epitope(s) or portion(s) of an IL-21 polypeptide of the present invention that they recognize or specifically bind. The epitope(s) or polypeptide portion(s) may be specified as described herein, e.g., by N-terminal and C-terminal positions, or by size in contiguous amino acid residues. Antibodies of the present invention may also be described or specified in terms of their cross-reactivity. Antibodies that do not bind any other analog, ortholog, or homolog of a polypeptide of the present invention are included.

Epitope binning refers to the use of competitive binding assays to identify pairs of antibodies that are, or are not, capable of binding IL-21 protein simultaneously thereby identifying antibodies that bind to the same, or overlapping epitopes on protein. Families of antibodies (or bins) having the same or overlapping binding specificity can then be used to help define specific epitopes on IL-21. Epitope binning experiments provide evidence that antigenically distinct epitopes are present. However, by themselves, they do not identify, or "map" the epitope to a specific amino acid sequence or location on the IL-21 protein molecule.

Competition for binding can be evaluated for any pair of antibodies or fragments. For example, using the appropriate detection reagents, the binding specificity of antibodies or binding fragments from any species/source can be compared to the binding specificity of the monoclonal antibodies disclosed herein. Epitope binning can be performed with "isolated antibodies" or with cell culture supernatants. Frequently, binning is performed with first round clonal supernatants to guide the choice of clones to be developed further. The antibodies to be compared should have substantially homogeneous antigen binding domains. In the case of "bispecific" or "bifunctional" antibodies the binding specificity of the two different binding sites need to be evaluated or binned independently.

The present invention features ligand-specific antibodies. In addition to competitive binding of antibodies, epitope binning can also be used to identify antibodies to either a receptor or a ligand that competitively interfere with the binding of a ligand to its receptor or the ligand mediated activation of its receptor. Frequently, favorable properties, of a family (or bin) of antibodies can be correlated with a binding to a specific epitope defined by the epitope bin.

Competitive binding experiments do not directly measure the binding affinity, however the antibodies to be tested must bind sufficiently strongly to act as competitors. Generally experimental conditions are designed to minimize the effects of differences in binding affinity.

Anti-IL-21 antibodies may also be useful in diagnostic assays for IL-21 protein, e.g., detecting its expression in specific cells, tissues, or serum. Antibodies assigned to different bins and capable of binding to different immunogenic portions, or epitopes, of IL-21 may be used as the reagents for sandwich assays. In a sandwich assay, the test sample analyte is captured by a first antibody which is immobilized on a solid support, and thereafter detected by a second antibody that also binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies of the present invention may be assayed for specific binding by any method known in the art. Many different competitive binding assay format(s) can be used for epitope binning The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name just a few. Such assays are routine and well known in the art (see, e.g., Ausubel et al, eds, 1994, *Current Protocols in Molecular Biology*, Vol. 1, John Wiley & Sons, Inc., New York). Exemplary immunoassays are described briefly below (but are not intended by way of limitation). Additionally, a routine cross-blocking assay such as that described in *Antibodies, A Laboratory Manual*, Cold Spring Harbor Laboratory, Ed Harlow and David Lane (1988), can be performed.

The BIACORE® (GE Healthcare, Piscataway, N.J.) is only one of a variety of surface plasmon resonance assay formats that are routinely used to epitope bin panels of monoclonal antibodies. Many references (e.g. The Epitope Mapping Protocols, *Methods in Molecular Biology*, Volume 66 Glenn E. Morris ed. Humana Press, 1996) describe alternative methods that could be used to bin antibodies and would be expected to provide comparable information regarding the binding specificity of the antibodies to IL-21 protein. When using the BIACORE® system, epitope binning experiments are performed with soluble, native or recombinant antigen. Epitope binning studies can be performed on a BIACORE1000® system (GE Healthcare, Piscataway, N.J.). BIAlogue® v. 1.2 software can be used for programming run methods. For the example of using the BIACORE® to bin mouse monoclonal antibodies raised against IL-21, polyclonal goat anti-Mouse IgG Fc antibody (Jackson ImmunoResearch Laboratories, West Grove, Pa.) can be covalently immobilized to a BIACORE® CM5 sensor chip and used to bind (capture) the primary monoclonal antibody of test series to the chip. Unoccupied Fc binding sites on the chip are then blocked using a polyclonal IgG Fc fragment (Jackson ImmunoResearch Laboratories, West Grove, Pa.). Subsequently, IL-21 protein is injected and allowed to specifically bind to the captured primary monoclonal antibody. The BIACORE® instrument measures the mass of protein bound to the sensor chip, and the binding of both the primary antibody and IL-21 antigen can be verified for each cycle. Following the binding of the primary antibody and antigen to the chip, soluble secondary antibody is injected and allowed to bind to the pre-bound antigen. If the secondary monoclonal antibody is capable of binding the IL-21 antigen simultaneously with the primary monoclonal antibody, its binding is detected by the BIACORE®. If, however, the secondary monoclonal antibody is not capable of binding the IL-21 antigen simultaneously with the primary monoclonal antibody, no additional binding is detected. Each monoclonal antibody is tested against itself as a negative control to establish the level of the background (no-binding) signal.

A label-free competitive ELISA format (LFC-ELISA) can also be used to bin antibodies. This method is described by Nagata et al., *J. Immuno Methods* 292:141-155, 2004. This method for epitope binning utilized biotinylated IL-21. For the example of binning mouse monoclonal antibodies raised against IL-21, microtiter plates are coated at 100 µL/well with 1 µg/mL of a goat anti-mouse IgG Fc-γ specific antibody (Jackson ImmunoResearch) diluted in ELISA B (PBS, 0.1% Tween 20, 1% BSA). After binding of this coating antibody for 3 hours at ambient temperature, each mAb-containing conditioned media is diluted in ELISA B to yield an approximate mAb concentration of 0.5 µg/mL and allowed to bind to the goat anti-mouse IgG coated plates overnight at 4° C. (mAb#1). In parallel, a second set of conditioned medias (mAb#2) are diluted in polystyrene test tubes to approximately 0.5 µg/mL mAb in ELISA B, mixed with 50 ng/mL biotinylated IL-21 antigen, and incubated overnight at 4° C. After incubation of mAb#1 with the coating antibody, the plates are blocked with an unrelated antibody to saturate unoccupied binding sites on the plate. The mAb#2-biotin-IL-21 mixtures are added to the plate and allowed to bind. As a control for (non-competition) in the assay, 50 ng/mL biotinylated IL-21 is added directly (without pre-incubation with mAb#2) to wells containing immobilized mAb#1. After incubation with the biotinylated-IL-21-mAb#2 complex, streptavidin-HRP (Pierce, Rockford, Ill.) is added to the plate at 0.5 µg/mL. The plates are developed with TMB substrate (BioFX Laboratories, Owings Mills, Md.), and the absorbance of the individual wells at 450 nm is measured with a plate reader (Molecular Devices SPECTRAMAX®340, Sunnyvale, Calif.). If mAb#1 binds to a different epitope from mAb#2, the biotin-IL-21-mAb#2 complex will bind to the plate resulting in a high absorbance reading. If mAb#1 binds to the same epitope as mAb#2, the biotin-IL-21-MAb#2 complex will not bind to the plate resulting in a low absorbance reading.

Ligand-specific antibodies of the present invention can simply bind to or act as antagonists of IL-21. For example, the present invention includes antibodies which do not disrupt IL-21's receptor/ligand interactions or disrupt IL-21's receptor/ligand interactions either partially or fully. The invention features ligand-specific antibodies that prevent receptor activation. The invention includes neutralizing antibodies which bind the ligand and prevent binding of the ligand to the receptor, as well as antibodies which bind the ligand, thereby preventing receptor activation, but do not prevent the ligand from binding the receptor. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot or luminex based analysis (for example, as described supra). In specific embodiments, antibodies are provided that inhibit ligand or receptor activity by at least 90%, at least 80%, at least 70%, at least 60%, or at least 50% of the activity in absence of the antibody.

Production of Anti-IL-21 Antibodies

Antibodies to IL-21 can be generated, for example, using protein that is the product of an IL-21 expression vector or IL-21 isolated from a natural source as an antigen. Anti-IL-21 antibodies of the present invention "bind specifically" to IL-21. Antibodies are considered to be specifically binding if the antibodies exhibit at least one of the following two properties: (1) antibodies bind to IL-21 with a threshold level of binding activity, and (2) antibodies do not significantly cross-react with polypeptides related to IL-21. Related polypeptides could include those of other members of the Type 1 cytokines that bind gamma common chain (γc)-containing receptors, such as IL-2, IL-4, IL-7, IL-9 and IL-15.

With regard to the first characteristic, antibodies specifically bind if they bind to a IL-21 polypeptide, peptide or epitope with a binding affinity as reflected in the measured affinity constants. To determine the affinity characteristics, measurements of the kinetic rate constants, equilibrium association constants, and equilibrium dissociation constants were assessed for the interaction of IL-21 antagonists with the IL-21 antigen via surface plasmon resonance. The association rate constant ($k_a$ ($M^{-1}s^{-1}$)) is a value that reflects the rate of the antigen-antagonist complex formation. The dissociation rate constant ($k_d$ ($s^{-1}$)) is a value that reflects the stability of this complex. Equilibrium binding affinity is typically expressed as either a dissociation equilibrium constant ($K_D$ (M)) or an association equilibrium constant ($K_A$ ($M^{-1}$)). $K_D$ is obtained by dividing the dissociation rate constant by the association rate constant ($k_d/k_a$), while $K_A$ is obtained by dividing the association rate constant by the dissociation rate constant ($k_a/k_d$). Antagonists with similar $K_D$ (or a similar $K_A$) can have widely variable association and dissociation rate constants. Consequently, measuring the $k_a$ and $k_d$ as well as the $K_A$ or $K_D$ helps to more uniquely describe the affinity of the antagonist-antigen interaction. The preferred affinity of an antibody is reflected in a KA (equilibrium association constant) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, Ann. NY Acad. Sci. 51:660, 1949), or using a commercially available biosensor instrument. With regard to the second characteristic, antibodies do not significantly cross-react with related polypeptide molecules, for example, if they detect IL-21, but not other known polypeptides using a standard Western blot analysis or capture ELISA. Examples of known related polypeptides include known members of the IL-2 family to which IL-21 belongs (for example, IL-2, IL-4, IL-7, IL-9 and IL-15).

Monoclonal anti-IL-21 antibodies can be produced using antigenic IL-21 epitope-bearing peptides and polypeptides. Antibodies of the present invention bind antigenic epitope-bearing peptides and polypeptides containing a sequence of at least nine, or between 15 to about 30 amino acids contained within SEQ ID NO:2 or another amino acid sequence disclosed herein. However, peptides or polypeptides comprising a larger portion of an amino acid sequence containing from 30 to 50 amino acids, or any length up to and including the entire amino acid sequence of a polypeptide also are useful for inducing antibodies that bind with IL-21. It is desirable that the amino acid sequence of the epitope-bearing peptide is selected to provide substantial solubility in aqueous solvents (i.e., the sequence includes relatively hydrophilic residues, while hydrophobic residues are typically avoided). Moreover, amino acid sequences containing proline residues may be also be desirable for large scale-antibody production.

Monoclonal anti-IL-21 antibodies can be generated by methods known to those skilled in the art. Rodent monoclonal antibodies to specific antigens may be obtained by known methods (see, for example, Kohler et al., *Nature* 256:495 (1975), Coligan et al. (eds.), Current Protocols in Immunology, Vol. 1, pages 2.5.1-2.6.7 (John Wiley & Sons 1991)

["Coligan"], Picksley et al., "Production of monoclonal antibodies against proteins expressed in *E. coli*," in *DNA Cloning 2: Expression Systems,* 2nd Edition, Glover et al. (eds.), page 93 (Oxford University Press 1995)).

The antibodies of the invention can be produced by any method known in the art for the synthesis of antibodies, in particular, by chemical synthesis or preferably, by recombinant expression techniques. Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., MPSV, CMV, the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus, CMV enhancer or MPSV promoter is an effective expression system for antibodies (Foecking et al., 1986, *Gene* 45:101; Cockett et al., 1990, *Bio/Technology* 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, *EMBO J.* 2:1791), in which the antibody coding sequence may be ligated individually into the vector in frame with the lacZ coding region so that a fusion protein is produced; pIN vectors (Inouye & Inouye, *Nucleic Acids Res.* 13:3101-3109, 1985; Van Heeke & Schuster, *J. Biol. Chem.* 24:5503-5509, 1989); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa califomica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355-359, 1984). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544, 1987).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell* 11:223, 1977), hypoxanthine-guanine phosphoribosyltransferase (Szybalska & Szybalski, *Proc. Natl. Acad. Sci. USA* 48:202, 1992), and adenine phosphoribosyltransferase (Lowy et al., *Cell* 22:817, 1980) genes can be employed in tk-, hgprt- or aprt-cells, respectively. Also, antimetabolite resistance can be used as the basis of selection for the following genes: dhfr, which confers resistance to methotrexate (Wigler et al., *Proc. Natl. Acad. Sci. USA* 77:357, 1980; O'Hare et al., *Proc. Natl. Acad. Sci. USA* 78:1527, 1981); gpt, which confers resistance to mycophenolic acid (Mulligan & Berg, *Proc. Natl. Acad. Sci. USA* 78:2072, 1981); neo, which confers resistance to the aminoglycoside G-418 (Wu and Wu, *Biotherapy* 3:87-95, 1991; Tolstoshev, *Ann. Rev. Pharmacol. Toxicol.* 32:573-596, 1993; Mulligan, *Science* 260:926-932, 1993; and Morgan and Anderson, *Ann. Rev. Biochem.* 62:191-217, 1993; *TIB TECH* 11(5):155-215), May, 1993; and hygro, which confers resistance to hygromycin (Santerre et al., *Gene* 30:147, 1984). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., *J. Mol. Biol.* 150:1, 1981; which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257, 1983).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, *Nature* 322:52, 1986; Kohler, *Proc. Natl. Acad. Sci. USA* 77:2197, 1980). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

For particular uses, it may be desirable to prepare fragments of anti-IL-21 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5 S fragment denoted F(ab')2. This fragment can be further cleaved using a thiol reducing agent to produce 3.5 S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., Arch *Biochem. Biophys.* 89:230, 1960; Porter, *Biochem. J.* 73:119, 1959; Edelman et al., in Methods in Enzymology Vol. 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of VH and VL chains. This association can be noncovalent, as described by Inbar et al., *Proc. Nat'l Acad. Sci. USA* 69:2659, 1972. Alternatively, the variable chains can be linked by an intermolecular disulfide bond or cross-linked by chemicals such as glutaraldehyde (see, for example, Sandhu, *Crit. Rev. Biotech.* 12:437, 1992).

The Fv fragments may comprise VH and VL chains which are connected by a peptide linker. These single-chain antigen binding proteins (scFv) are prepared by constructing a structural gene comprising DNA sequences encoding the VH and VL domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., Methods: A Companion to Methods in Enzymology 2:97 (1991) (also see, Bird et al., *Science* 242:423, 1988, Ladner et al., U.S. Pat. No. 4,946,778, Pack et al., *Bio/Technology* 11:1271, 1993, and Sandhu, supra).

It is also possible to construct alternative frameworks by using a collection of monomeric proteins to form a monomer domain. These monomer domains can be small enough to penetrate tissues. The monomer domains can be naturally-occurring or non-natural variants or combination thereof. Monomer domains can form multimers of two or more domains. The monomer domain binds a position, analogous to epitopes described herein, on a target molecule. In some cases, the multimer can be formed from a variety of monomer domains. (See, e.g. U.S. Patent Application 2004-0132028 and U.S. Patent Application 2006-0177831.)

The antibodies of the present invention include derivatives that are modified, i.e., by the covalent attachment of any type of molecule to the antibody such that covalent attachment does not prevent the antibody from binding IL-21 or blocking receptor activation. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

An anti-IL-21 antibody can be conjugated with a detectable label to form an anti-IL-21 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below. The detectable label can be a radioisotope that is detected by autoradiography. Isotopes that are particularly useful for the purpose of the present invention are $^3H$, $^{125}I$, $^{131}I$, $^{35}S$ and $^{14}C$.

Anti-IL-21 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde, alexadyes, fluorescent nonparticles (e.g. Q dots) and fluorescamine.

It is also possible that anti-IL-21 immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-IL-21 immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-IL-21 immunoconjugates can be detectably labeled by linking an anti-IL-21 antibody component to an enzyme. When the anti-IL-21-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-IL-21 antibodies can be accomplished using standard techniques known to the art. Typical methodology in this regard is described by the following: Kennedy et al., *Clin. Chim. Acta* 70:1, 1976; Schurs et al., *Clin. Chim. Acta* 81:1, 1977; Shih et al., *Int'l J. Cancer* 46:1101, 1990; Stein et al., *Cancer Res.* 50:1330, 1990; and Coligan, supra.

Moreover, the convenience and versatility of immunochemical detection can be enhanced by using anti-IL-21 antibodies that have been conjugated with avidin, streptavidin, and biotin (see, for example, Wilchek et al. (eds.), "Avidin-Biotin Technology," Methods In Enzymology, Vol. 184 (Academic Press 1990), and Bayer et al., "Immunochemical Applications of Avidin-Biotin Technology," in Methods In Molecular Biology, Vol. 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180-208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107-120 (Wiley-Liss, Inc. 1995), and Diamandis, *Immunoassay* (Academic Press, Inc. 1996).

Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG, for example, to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Pharmaceutical Compositions

The present invention further includes pharmaceutical compositions, comprising a pharmaceutically acceptable carrier and a polypeptide or antibody described herein. The pharmaceutical composition can include additional therapeutic agents, including but not limited to cytotoxic agents a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). For example, the pharmaceutical composition can comprise a protein or polypeptide possessing a desired biological activity. Such proteins may include, for example, a toxin such as abrin, ricin A, pseudomonas exotoxin, or diphtheria toxin; a protein such as tumor necrosis factor, α-IFN, β-IFN, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), antibodies designed to antagonize biological response modifiers, other antibodies, other Fc fusion proteins or other growth factors.

For purposes of therapy, anti-IL-21 antibody molecules and a pharmaceutically acceptable carrier are administered to a patient in a therapeutically effective amount. A combination of a therapeutic molecule of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response.

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332, 1995; Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161, 1998; Putney and Burke, *Nature Biotechnology* 16:153, 1998; Putney, *Curr. Opin. Chem. Biol.* 2:548, 1998). Polyethylene glycol (PEG)-coated nanospheres can also provide carriers for intravenous administration of therapeutic proteins (see, for example, Gref et al., *Pharm. Biotechnol.* 10:167, 1997).

Other dosage forms can be devised by those skilled in the art, as shown, for example, by Ansel and Popovich, *Pharmaceutical Dosage Forms and Drug Delivery Systems*, 5th Edition (Lea & Febiger 1990), Gennaro (ed.), *Remington's Pharmaceutical Sciences*, 19th Edition (Mack Publishing Company 1995), and by Ranade and Hollinger, *Drug Delivery Systems* (CRC Press 1996).

Pharmaceutical compositions may be supplied as a kit comprising a container that comprises a neutralizing anti-IL-21 antibody. Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition.

A pharmaceutical composition comprising anti-IL-21 antibodies can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239, 1997; Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Therapeutic Uses for Anti-IL-21 Antibodies

IL-21 is a $CD4^+$ T cell-derived cytokine that is important for optimal $CD8^+$ T cell mediated immunity, NK cell activation, and optimal humoral responses, such as antibody production and B cell maturation. IL-21 has been shown to induce a number of proinflammatory chemokines and cytokines, such as IL-18, IL-15, IL-5, IL-6, IL-7A, IL-17F, TNFRII, sCD25, and RANTES. IL-21 also induces an acute phase response in non-human primates and humans when administered by IV or SC injection (Dodds et al., *Cancer Immunol Immunother* 2008 Oct. 17 [electronic publication]). In vitro, stimulates the growth of certain neoplastic immune cell populations such as multiple myeloma cells and acute T-cell leukemia (Brenne et al *Blood* 99(10):3756-62 (2002), diCarlo E, et al *Cancer Immunol Immunother* 56(9):1323-1324 (2007)). IL-21 is also produced by Hodgkin Reed-Sternberg cells in Hodgkin's Lymphoma (Lamprecht et al., *Blood* 112(8):3339-47, 2008). Increased expression of IL-21 receptor has been shown in epidermis in patients with systemic sclerosis (Distler et al., *Arthritis & Rheumatism* 52:865-864, 2004) and rheumatoid arthritis synovial fibroblasts (Jungel et al., *Arthritis & Rheumatism* 50:1468-1476, 2004). Moreover, autoimmune, diabetic NOD mice have increased IL-21 receptor expression (King et al., *Cell* 117: 265-277, 2004.) It has been shown that IgG and IL-21 expression is increased in the BXSB-Yaa mouse model which develop an autoimmune lupus erythematosus-like disease (Ozaki et al., *J. Immunol.* 173:5361-5371, 2004); IL-21 expression is higher in lupus-prone sanroque mice (Vinuesa et al. *Nature* 435:452, 2005); IL-21 expression is higher in inflamed vs uninflamed gut tissues from patients with Crohn's disease (Monteleone, et al., *Gastroenterology* 128: 687-694, 2005). IL-21 is also overproduced in the mucosa of celiac disease patients (Finn et al. *Gut, PMID*:17965065, 2007).

A therapeutically effective amount of an anti-IL-21 antibody refers to an amount of antibody which when administered to a subject is effective to prevent, delay, reduce or inhibit a symptom or biological activity associated with a disease or disorder. Administration may consist of a single dose or multiple doses and may be given in combination with other pharmaceutical compositions.

The present invention provides compositions and methods for using anti-IL-21 monoclonal antibodies in inflammatory and immune diseases or conditions such as psoriasis, pancreatitis, type I diabetes (IDDM), Graves' Disease, inflammatory bowel disease (IBD), Crohn's Disease, ulcerative colitis, irritable bowel syndrome, multiple sclerosis, rheumatoid arthritis, reactive arthritis, enteropathic arthritis, spondyloarthropathy, autoimmune myocarditis, Kawasaki disease, celiac disease, uveitis, Behcet's disease, coronary artery disease, chronic obstructive pulmonary disease (COPD), interstitial lung disease, inflammatory muscle disease (polymyositis, dermatomyositis), microscopic polyangiitis, autoimmune aplastic anemia, autoimmune thyroiditis, autoimmune hepatitis, Wegener's syndrome, diverticulosis, systemic lupus erythematosus, ankylosing spondylitis, scleroderma, systemic sclerosis, psoriatic arthritis, osteoarthritis, atopic dermatitis, vitiligo, graft vs. host disease (GVHD), cutaneous T cell lymphoma (CTCL), Sjogren's syndrome, glomerulonephritis, IgA nephropathy, autoimmune nephritis, pemphigus vulgaris, myasthenia gravis, autoimmune hearing loss, neuromyelitis optica, Goodpasture's syndrome, cryoglobulinemia, Guillain Bane syndrome, chronic inflammatory demyelinating polyneuropathy (CIDP), autoimmune hemolytic anemia, idiopathic thrombocytopenic purpura (ITP), transplant rejection, highly sensitized transplant patients, anti-phospholipid syndrome, allergy, and asthma, and other autoimmune diseases. The present invention provides compositions and methods for using anti-IL-21 monoclonal antibodies in the therapy for certain immune cell cancers such as multiple myeloma, acute T-cell leukemia, or Hodgkin's Lymphoma.

Contact Dermatitis

Allergic contact dermatitis is defined as a T cell mediated immune reaction to an antigen that comes into contact with the skin. The CLA+ T cell population is believed to be involved in the initiation of dermatitis since allergen dependent T cell responses are largely confined to the CLA+ population of cells (See Santamaria-Babi, et al., *J Exp Med* 181: 1935, (1995)). Recent data have found that only memory (CD45RO+) CD4+ CLA+ and not CD8+ T cells proliferate and produce both type-1 (IFN-γ) and type-2 (IL-5) cytokines in response to nickel, a common contact hypersensitivity allergen. Furthermore, cells expressing CLA in combination with CD4, CD45RO (memory) or CD69 are increased after nickel-specific stimulation and express the chemokine receptors CXCR3, CCR4, CCR10 but not CCR6. See Moed et al., *Br J Dermatol* 51:32, (2004).

In animal models, it has been demonstrated that allergic contact dermatitis is T cell-dependent and that the allergic-responsive T cells migrate to the site of allergen application. See generally: Engeman, et al., *J Immunol* 164:5207, (2000); Ferguson & Kupper, *J Immunol* 150:1172, (1993); and Gorbachev & Fairchild, *Crit Rev Immunol*. 21:451 (2001).

Administration anti-IL-21 antibodies to mousse models of contact hypersensitivity is used to evaluate the clinical utility of anti-IL-21 antibodies to ameliorate symptoms and alter the course of disease.

Atopic Dermatitis

Atopic dermatitis (AD) is a chronically relapsing inflammatory skin disease with a dramatically increasing incidence over the last decades. Clinically AD is characterized by highly pruritic, often excoriated, plaques and papules that show a chronic relapsing course. The diagnosis of AD is mostly based on major and minor clinical findings. See Hanifin J. M., *Arch Dermatol* 135:1551 (1999). Histopathology reveals spongiosis, hyperparakeratosis and focal parakeratosis in acute lesions, whereas marked epidermal hyperplasia with hyperparakeratosis and parakeratosis, acanthosis/hypergranulosis and perivascular infiltration of the dermis with lymphocytes and abundant mast cells are the hallmarks of chronic lesions.

T cells play a central role in the initiation of local immune responses in tissues and evidence suggests that skin-infiltrating T cells in particular, may play a key role in the initiation and maintenance of disregulated immune responses in the skin. Approximately 90% of infiltrating T cells in cutaneous inflammatory sites express the cutaneous lymphocyte-associated antigen which binds E-selectin, an inducible adhesion molecule on endothelium (reviewed in Santamaria-Babi, et al., *Eur J Dermatol* 14:13, (2004)). A significant increase in circulating CLA+ T cells among AD patients compared with control individuals has been documented (See Teraki, et al., *Br J Dermatol* 143:373 (2000), while others have demonstrated that memory CLA+ T cells from AD patients preferentially respond to allergen extract compared to the CLA– population (See Santamaria-Babi, L. F., et al., *J Exp Med*. 181:1935, (1995)). In humans, the pathogenesis of atopic disorders of the skin have been associated with increases in CLA+ T cells that express increased levels of Th-2-type cytokines like IL-5 and IL-13. See Akdis et al., *Eur J Immunol* 30:3533 (2000); and Hamid et al., *J Allergy Clin Immunol* 98: 225 (1996).

NC/Nga mice spontaneously develop AD-like lesions that parallel human AD in many aspects, including clinical course and signs, histopathology and immunopathology when housed in non-specified pathogen-free (non-SPF) conditions at around 6-8 weeks of age. In contrast, NC/Nga mice kept under SPF conditions do not develop skin lesions. However, onset of spontaneous skin lesions and scratching behaviour can be synchronized in NC/Nga mice housed in a SPF facility by weekly intradermal injection of crude dust mite antigen. See Matsuoka et al., *Allergy* 58:139 (2003). Therefore, the development of AD in NC/Nga is a useful model for the evaluation of novel therapeutics for the treatment of AD.

In addition to the NC/Nga model of spontaneous AD, epicutaneous sensitization of mice using OVA can also be used as a model to induce antigen-dependent epidermal and dermal thickening with a mononuclear infiltrate in skin of sensitized mice. This usually coincides with elevated serum levels of total and specific IgE, however no skin barrier dysfunction or pruritus normally occurs in this model. See Spergel et al., *J Clin Invest*, 101:1614, (1998). This protocol can be modified in order to induce skin barrier disregulation and pruritus by sensitizing DO11.10 OVA TCR transgenic mice with OVA. Increasing the number of antigen-specific T cells that could recognize the sensitizing antigen may increase the level of inflammation in the skin to induce visible scratching behaviour and lichenification/scaling of the skin.

Administration of anti-IL-21 antibodies to mouse models of atopic dermatitis is used to evaluate the clinical utility of anti-IL-21 antibodies to ameliorate symptoms and alter the course of disease.

Arthritis

Arthritis, including osteoarthritis, rheumatoid arthritis, arthritic joints as a result of injury, and the like, are common inflammatory conditions which would benefit from the therapeutic use of anti-inflammatory antibodies and binding polypeptides. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid Arthritis

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149, 2002).

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is administered as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995).

The administration of anti-IL-21 antibodies to these CIA model mice is used to evaluate the use of anti-IL-21 antibodies to ameliorate symptoms and alter the course of disease.

Inflammatory Bowel Disease (IBD)

In the United States approximately 500,000 people suffer from inflammatory bowel disease (IBD) which can affect either colon and rectum (ulcerative colitis) or both, small and large intestine (Crohn's Disease). The pathogenesis of these diseases is unclear, but they involve chronic inflammation of the affected tissues. Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the immune systems thinks are "non-self" (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (e.g. azathioprine, mercaptopurine, and methotrexate) and aminosalicytates are available to treat the disease. However, the long-term use of immunosuppressives such as corticosteroids and azathioprine can result in serious side effects including bone-thinning, cataracts, infection, and liver and bone marrow effects. In the patients in whom current therapies are not successful, surgery is an option. However, the surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanied by the clinical picture of progressive weight loss (wasting), bloody diarrhea, rectal prolapse, and large bowel wall thickening (Neurath et al. *Intern. Rev. Immunol.* 19:51-62, 2000). Adoptive transfer of naive T cells into minor histocompatibility mismatched or syngeneic immunocompromised mice leads to development of colitis (Leach M W et al 1996, Powrie F et al, 1997) as well as skin lesions resembling psoriasis (Schon M P et al., *Nat Med.* 2:183-8, 1997; Davenport C M et al., *Int Immunopharmacol.* 5:653-72, 2002). Transplantation of as few as 0.2 million CD4+CD25− T cells from BALB/C or B10.D2 mice into immunocompromised C.B-17 SCID mice results in weight loss, hemoccult positive stool and development of skin lesions. The symptoms in these mice vary from colony to colony. This model of colitis/psoriasis has some similarities to human Crohn's disease and psoriasis, and has been used extensively to test efficacy of therapeutics for these diseases in humans.

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS-induced disease and its relevance to the human disease remain unresolved. DSS is regarded as a T cell-independent model because it is observed in T cell-deficient animals such as SCID mice.

The administration of anti-IL-21 antibodies to these TNBS, DSS or CD4+ T cell-transfer models can be used to evaluate the use of IL-21 antagonists to ameliorate symptoms and alter the course of gastrointestinal disease. IL-21 may play a role in the inflammatory response in colitis, and the neutralization of IL-21 activity by administrating IL-21 antagonists is a potential therapeutic approach for IBD.

Psoriasis

Psoriasis is a chronic skin condition that affects more than seven million Americans. Psoriasis occurs when new skin cells grow abnormally, resulting in inflamed, swollen, and scaly patches of skin where terminal differentiation of keratinocytes is altered. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves T cell activation, altered antigen presentation and cytokine production by inflammatory dendritic cells, and chronic inflammation of the affected tissues. Anti-IL-21 antibodies of the present invention, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet light treatments or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy. Anti-IL-21 antibodies can be tested using a recently developed a model of psoriasis based on the CD4+CD45RB transfer model (Davenport et al., *Internat. Immunopharmacol.*, 2:653-672, 2002).

In addition to other disease models described herein, the activity of anti-IL-21 antibodies on inflammatory tissue derived from human psoriatic lesions can be measured in vivo using a severe combined immune deficient (SCID) based mouse model. Several mouse models have been developed in which human cells or tissue grafts are implanted into immunodeficient mice (collectively referred to as xenograft models); see, for example, Cattan and Douglas, *Leuk. Res.* 18:513-22, 1994 and Flavell, *Hematological Oncology* 14:67-82, 1996. As an in vivo xenograft model for psoriasis, human psoriatic skin tissue is grafted onto SCID mice, and the mice are subsequently challenged with an appropriate antagonist. Moreover, other psoriasis animal models in the art may be used to evaluate IL-21 antagonists, such as human psoriatic skin grafts implanted into the AGR129 mouse model, and challenged with an appropriate antagonist (e.g., see, Boyman et al., *J. Exp. Med.* Online publication #20031482, 2004). Similarly, tissues or cells derived from human colitis, IBD, arthritis, or other inflammatory lesions can be used in the SCID model to assess the anti-inflammatory properties of the anti-IL-21 antibodies described herein.

Efficacy of treatment is measured and statistically evaluated as increased anti-inflammatory effect within the treated population over time using methods well known in the art. Some exemplary methods include, but are not limited to measuring for example, in a psoriasis model, epidermal thickness, the number of inflammatory cells in the upper dermis, and the grades of parakeratosis. Such methods are known in the art and described herein. For example, see Zeigler et al., *Lab Invest* 81:1253, 2001; Zollner et al., *J. Clin. Invest.* 109:671, 2002; Yamanaka et al., *Microbiol. Immunol.* 45:507, 2001; Raychaudhuri et al., *Br. J. Dermatol.* 144:931, 2001; Boehncke et al., *Arch. Dermatol. Res.* 291:104, 1999; Boehncke et al., *J. Invest. Dermatol.* 116:596, 2001; Nickoloff et al., *Am. J. Pathol.* 146:580, 1995; Boehncke et al., *J. Cutan. Pathol.* 24:1, 1997; Sugai et al., *J. Dermatol. Sci.* 17:85, 1998; and Villadsen et al., *J. Clin. Invest.* 112:1571, 2003. Inflammation may also be monitored over time using well-known methods such as flow cytometry (or PCR) to quantitate the number of inflammatory or lesional cells present in a sample, score (weight loss, diarrhea, rectal bleeding, colon length) for IBD, paw disease score and inflammation score for CIA RA model.

The administration of anti-IL-21 antibodies to these psoriasis model mice is used to evaluate the use of anti-IL-21 antibodies to ameliorate symptoms and alter the course of disease.

Systemic Lupus Erythematosus

Systemic lupus erythematosus (SLE) is an immune-complex related disorder characterized by chronic IgG antibody production directed at ubiquitous self antigens (e.g. anti-dsDNA). The effects of SLE are systemic, rather than localized to a specific organ, although glomerulonephritis may result in some cases (i.e. lupus nephritis). Multiple chromosomal loci have been associated with the disease and may contribute towards different aspects of the disease, such as anti-dsDNA antibodies and glomerulonephritis. CD4+ T cells have been shown to play an active part in mouse models of SLE (Horwitz, *Lupus* 10:319-320, 2001; Yellin and Thienel, *Curr. Rheumatol. Rep.*, 2:24-37, 2000). The role for CD8+ T cells is not clearly defined, but there is evidence to suggest that "suppressor" CD8+ T cell function is impaired in lupus patients (Filaci et al., *J. Immunol.*, 166:6452-6457, 2001; Sakane et al, *J. Immunol.*, 137:3809-3813, 1986).

IL-21 has been convincingly shown to induce the differentiation of naïve human B cells into antibody-secreting plasma cells (Ozaki et al., *J. Immunol.* 173:5361, 2004; Ettinger et al., *J Immunol.* 175:7867-79, 2005; Ettinger et al, *J Immunol.* 178:2872-82, 2007; Kuchen et al. *J Immunol.* 179:5886-96, 2007). Ozaki et al., (*J. Immunol.* 173:5361, 2004) also demonstrated that IL-21 expression is elevated in lupus-prone BXSB-Yaa mice, a model for SLE, at an age when the early characteristics of autoimmune processes first become evident. Treatment of these BXSB-Yaa mice with a murine IL-21 antagonist partially inhibits various disease parameters, including glomerulonephritis (Bubier et al., *Ann N Y Acad Sci.* 1110:590-601, 2007). The same IL-21 antagonist has also been shown to be efficacious in another pre-clinical disease model of SLE, the MRL/lpr mouse (Herber et al. *J. Immunol.* 178: 3822-3830, 2007). Moreover, because IL-21 limits development of Treg cells, administration of anti-IL-21 antibodies could provide a more robust T cell suppressor function in lupus patients where that function is compromised (Lamprecht et al. *Blood.* 112(8):3339-47, 2008).

Data obtained from 24 SLE patients and 15 healthy controls showed that 1) IL-21 mRNA expression is significantly increased in CD4+ T cells from lupus patients compared to controls, 2) IL-21 levels are significantly elevated in sera from patients with active compared to inactive SLE or controls, as determined using a commercial IL-21 ELISA kit (Invitrogen, Carlsbad, Calif.), 3) IL-21 enhances CD4+ T cells and CD19+ B cells proliferation in patients and controls in a dose dependent fashion, 4) IL-21 enhances anti-CD40 induced plasma cell differentiation in normal controls and SLE patients, and 5) elevated levels of IL-21 may contribute to proliferation of autoreactive CD4+ T cells and plasma cell differentiation in SLE ((Rus, V., *ACR Presentation* #1760, 2008 American College of Rheumatology meeting, Oct. 24-29, 2008).

Anti-IL-21 antibodies can be administered in combination with other agents already in use in autoimmunity including immune modulators such as IFNγ, NOVANTRONE®, ENBREL®, BETAFERON®, REMICADE®, LEUKINE® and PROLEUKIN®. Anti-IL-21 antibodies can be administered in combination with other agents already in use in the cancer therapy of multiple myeloma, Hodgkin's Lymphoma or acute T-cell leukemia such as THALOMID® or with steroids such as dexamethasone or prednisone. Establishing the optimal dose level and scheduling for anti-IL-21 antibodies is done by a variety of means, including study of the pharmacokinetics and pharmacodynamics of anti-IL-21 antibodies; determination of effective doses in animal models, and evaluation of the toxicity of anti-IL-21 antibodies. Direct pharmacokinetic measurements done in primates and clinical trials can then be used to predict theoretical doses in patients that achieve plasma anti-IL-21 antibody levels that are of sufficient magnitude and duration to achieve a biological response in patients.

Transplant Rejection

Recipients of transplanted solid organs may develop acute or chronic rejection of the allograft due to histocompatibility mismatch. The generation of antibodies directed against the HLA molecules (alloantibodies) in these patients results from presentation of the foreign antigen to T cells. Alloantibodies may mediate tissue damage in the graft through formation of immune complexes, complement fixation, and antibody mediated cellular cytotoxicity directed by bound alloantibodies. The complement cascade also releases local factors that activate endothelial cells and cause vasculopathy within the graft. The complement product C4d is an early marker in both acute and chronic transplant rejection, and can be detected in sub-clinical cases prior to overt pathological changes (Racusen and Haas, *Clin J Am Soc Nephrol* 1: 415-420, 2006; Moll and Pascual, *Am J Transplantation* 5: 2611-2618, 2005; Tinkam and Chandraker, *Clin J Am Soc Nephrol* 1: 404-414, 2006). Patients are screened for anti-HLA alloantibodies (panel reactive antibody) prior to transplantation. Patients may be highly sensitized due to prior allograft failure, blood transfusions, or multiple pregnancies. The presence of alloantibodies in highly sensitized transplant patients complicates their care, as increased immunosuppressive therapies may be required and the chance of acute rejection is high (Baid et al., *Curr Opin Immunol* 13:577-581, 2001). In some cases, B cell targeting agents (mycophenolic acid or rituximab) are used, although this therapeutic strategy does not directly target the antibody-secreting plasma cells. Plasmapheresis is also used to reduce circulating immunoglobulin. In all cases, transplant recipients are treated with T cell targeted immunosuppressive agents to reduce the risk of rejection, and may be slowly "weaned" from these regimens as tolerance to the graft is established (Seyfort-Margolis and Turka, *J Clin Invest* 118 (8): 2684-2685, 2008; Taylor et al., *Crit Rev Oncol Hematol* 56:23-46, 2005; Amante and Ejercito, *Transplant Proc* 40: 2274-2280, 2008).

Development of antibody secreting plasma cells requires cognate help from CD4 T cells in addition to the specialized microenvironments that support plasma cell survival (Tarlington et al., *Curr Opin Immunol* 20:162-169, 2008). Cytokine secretion by activated T cells is necessary for differentiation and survival of plasma cells, and is known to affect the nature of the antibody response and Ig isotype. Models exist to monitor T cell dependent antibody responses in murine and non-human primate species. These methods are well understood by those skilled in the art. Kinetics and magnitude of primary or secondary antibody responses against model peptide antigens such as ovalbumin, tetanus toxoid, sheep red blood cells, or trinitrophenyl modified keyhole limpet hemocyanin are monitored using assays that detect total or antigen-specific antibodies, including IgG sub-types, IgM, IgE, or IgA in serum of treated animals. In some models, affinity maturation of the antibodies can also be monitored. These models may be used to test the effects of therapeutic drugs that alter B cell help by T cells and that block cytokines thought to be important for plasma cell differentiation and survival.

Studies of allograft rejection are conducted in many animal species. For example, a renal transplant model in cynomolgus monkeys may represent the effects of chronic alloantibody mediated renal allograft rejection in humans. Allograft tolerizing regimens are performed prior to transplant in some cases. The presence of donor-specific alloantibodies is monitored by flow cytometric analysis of recipient serum with mismatched peripheral blood leukocytes, and deposition of the complement product C4d is detected in biopsies from the renal allograft (Smith et al., *Am J Transplant* 6:1790-1798, 2006; Smith et al., *Am J Transplant* 8:1-11, 2008). Acute and chronic transplant models may be conducted in murine species by those skilled in the art.

Administration of anti-IL-21 antibodies in a model of T cell dependent antibody response or a model of allograft rejection is used to evaluate the clinical utility of anti-IL-21 antibodies to reduce alloantibody responses, and ameliorate symptoms of allograft rejection, or as part of the pre-transplant therapeutic or tolerizing regimen for transplant recipients, including highly sensitized transplant patients.

The invention is further illustrated by the following non-limiting examples.

EXAMPLES

Example 1

Preparation of IL-21 Proteins and Antibodies

A. Immunizations and Hybridomas

IL-21 protein was produced as described in U.S. Pat. No. 7,250,274, incorporated in its entirety herein. Soluble IL-21 receptor proteins were produced as described in U.S. Patent Application 2007-0122413 and U.S. Pat. No. 6,777,539, both incorporated in their entirety herein. Anti-IL-21 monoclonal antibodies were produced in wild type mice generating murine antibodies and in transgenic mice generating fully human antibodies (Medarex, Princeton, N.J.). Mice were immunized with human IL-21 protein. Briefly, the mice were initially immunized by subcutaneous injection with 30 μg of purified recombinant IL-21 (produced in *E. coli* at ZymoGenetics) conjugated with BSA (Imject Pharmalink Immunogen Kit, Pierce) and administered in combination with CpG (oligonucleotide murine TLR9 ligand and GM-CSF (Granulocyte Macrophage Colony Stimulatory Factor, R&D, Minneapolis, Minn.) and Emulsigen®-P adjuvant (MVP Laboratories, INC, Omaha, Nebr.) as per manufacturer's instructions. Following the initial immunization, each of the mice received three additional 30 μg of IL-21 in Emulsigen®-P adjuvant via the subcutaneous route in weekly intervals. Seven days after the fourth immunization, the mice were bled via the retro orbital plexus and the serum separated from the blood for analysis of its ability to bind to IL-21.

Splenocytes were harvested and pooled from two high-titer BALB/c mice or transgenic mice and fused to P3-X63-Ag8.653 mouse myeloma cells using PEG 1450 in a single fusion procedure (2:1 fusion ratio, splenocytes to myeloma cells, "Antibodies: A Laboratory Manual", E. Harlow and D. Lane, Cold Spring Harbor Press). Following 9 days growth post-fusion, specific antibody-producing hybridoma pools were identified by Direct and Capture ELISA using recombinant IL-21 protein, untagged and human IgG Fc tagged, as specific antibody target. Positive hybridoma pools were analyzed further for their ability to block the Ligand to receptor binding, which is measured as the level of STAT3-phosphorylation following ligand-receptor interaction ("phosphor-STAT3 neutralization assay") of purified recombinant IL-21 protein on BaF3 cells expressing the IL-21 receptor sequence. Monoclonal antibodies purified from tissue culture media were characterized for their ability to block the ligand-receptor interaction ("phosphor-STAT3 neutralization assay") of purified recombinant IL-21 on Baf3 cells expressing the receptor sequences. "Neutralizing" monoclonal antibodies were identified in this manner.

Hybridoma pools yielding positive results by the "phosphor-STAT3 neutralization assay" and ELISA formats were cloned at least two times by limiting dilution. In these assays, samples were titrated using standard low density dilution (less than one cell per well) to see which clone will maintain the highest OD reading. Using the results from both the neutralization and titration assays, two specific clones from each initial master well were selected for further analysis. These are subjected to an additional round of cloning to ensure culture homogeneity and screened using the Direct ELISA. After one additional titration assay, two final IL-21 clones were selected. Hybridoma clones were cultured in a growth medium of 90% Iscove's Modified Dulbecco's medium with 2 mM L-glutamine, 100 μg/mL penicillin, and 100 μg/mL streptomycin sulfate, and 10% Fetal Clone I Serum (Hyclone Laboratories). The clones were propagated by seeding cultures at $2 \times 10^5$ cells/ml and maintaining between $1 \times 10^5$ and $5 \times 10^5$ cell/ml at 37° C. and 5-6% $CO_2$. Cells were adapted to serum free conditions upon subsequent transfers. Cells are frozen in 90% serum, 10% DMSO and stored in vapor phase of a liquid nitrogen freezer.

The purified monoclonal antibodies produced by the hybridoma clones were characterized in a number of ways including binning (i.e., determining if each antibody could inhibit the binding of any other antibody), epitope mapping using peptides, relative affinity, and neutralization.

Methods for producing heterologous antibodies from transgenic mice are known, see for example, Lonberg, *Nat. Biotech.* 23(9):1117-25, 2005; Tomizuka et al. *PNAS* 97(2): 722-727, 2000; and U.S. Pat. No. 5,625,126.

The following hybridomas producing murine anti-human IL-21 monoclonal antibodies have been deposited with the American Type Culture Collection, Manassas, Va. clone 338.5.4 ATCC No. (PTA-8317), clone 338.11.5 ATCC No. (PTA-8314), clone 338.14.3 ATCC No. (PTA-8313), clone 338.15.5 ATCC No. (PTA-8315), clone 338.17.3 ATCC No. (PTA-8316), clone 338.24.5 ATCC No. (PTA-8430), clone 338.25.6 ATCC No. (PTA-8431), clone 338.39.5 ATCC No. (PTA-8432), clone 338.29.2 ATCC No. (PTA-8433), clone 338.28.6 ATCC No. (PTA-8434).

The following hybridomas producing human anti-human IL-21 monoclonal antibodies have been deposited with the American Type Culture Collection, Manassas, Va. Table 1 provides complete amino acid sequences for the variable heavy (VH) and variable light (VL) chains of the antibodies. Also included are sequences for CDR1, CDR2 and CDR3 of VH and VL regions for each antibody. The corresponding nucleotide sequences are found in the sequence listing. Included in the deposit, but not in Table 1, is a hybridoma designated 366.345.6.11, ATCC No. PTA-8788.

TABLE 1

| Clone Number | ATCC No. | VH CDR1 | VH CDR2 | VH CDR3 | VL CDR1 | VL CDR2 | VL CDR3 | Complete Sequence |
|---|---|---|---|---|---|---|---|---|
| 362.75.1.1.7 | PTA-8791 | SRTYRWG SEQ ID NO: 15 | SIYYRGSTFYNPSLKS SEQ ID NO: 17 | QSGYSGYDWFDP SEQ ID NO: 19 | RASQSVSSFLA SEQ ID NO: 23 | DASNRAT SEQ ID NO: 25 | QQRSNWIT SEQ ID NO: 27 | VH<br>MKHLWFFLLLVAAPRWVLSQLQLQESGPGLVKPSETLSL<br>TCTVSGGSISSRTYRWGWIRQPPGKELEWIGSIYYRGSTF<br>YNPSLKSRVTVSVDTSKNQFSLKLSSVTAADTAVYYCAR<br>QSGYSGYDWFDPWGQGTLVTVSS<br>SEQ ID NO: 13<br><br>VL<br>MEAPAQLLFLLLLWLPDTTGEIVLTQSPATLSLSPGERAT<br>LSCRASQSVSSFLAWYQQKPGQAPRLLIYDASNRATGIP<br>ARFSGSGSGTDFTLTISSLEPEDFAVYYCQQRSNWITFGQ<br>GTRLEIK<br>SEQ ID NO: 21 |
| 362.78.1.44 | PTA-8790 | SYGMH SEQ ID NO: 31 | FIWYDGSDKYYADSVKG SEQ ID NO: 33 | DGDSSDWYGDYYFGMDV SEQ ID NO: 35 | RASQSVSSSYLA SEQ ID NO: 39 | GASSRAT SEQ ID NO: 41 | QQYGSWT SEQ ID NO: 43 | VH<br>MEFGLSWVFLVALLRGVQCQVQLVESGGGVVQPGRSLR<br>LSCAASGFTFSSYGMHWVRQAPGKGLEWVAFIWYDGSD<br>KYYADSVKGRFTISRDNSKNTLYLQMNSLRAEDTAVYY<br>CARDGDSSDWYGDYYFGMDVWGQGTTVTVSS<br>SEQ ID NO: 29<br><br>VL<br>METPAQLLFLLLLWLPDTTGEIVLTQSPGTLSLSPGERAT<br>LSCRASQSVSSSYLAWYQQKPGQAPRLLIYGASSRATGIP<br>DRFSGSGSGTDFTLTISRLEPEDFAVYYCQQYGSWTFGQ<br>GTKVEIK<br>SEQ ID NO: 37 |

TABLE 1-continued

| Clone Number | ATCC No. | VH CDR1 | VH CDR2 | VH CDR3 | VL CDR1 | VL CDR2 | VL CDR3 | Complete Sequence |
|---|---|---|---|---|---|---|---|---|
| 362.597. 3.15 | PTA-8786 | TYGMH SEQ ID NO: 47 | FIWYD GSDKY YADSV KG SEQ ID NO: 49 | DGDSS DWYGD YYFGM DV SEQ ID NO: 51 | RASQS VSSSYL A SEQ ID NO: 55 | GASSR AT SEQ ID NO: 57 | QQYGS WT SEQ ID NO: 59 | VH<br>MEFGLSWVFLVALLRGVQCQVQLVESGGGVVQPGRSLR<br>LSCAASGFTFSTYGMHWVRQAPGKGLEWVAFIWYDGS<br>DKYYADSVKGRFTISRDNSKNTLYLQMNSLRAEDTAVY<br>YCARDGDSSDWYGDYYFGMDVWGQGTTVTVSS<br>SEQ ID NO: 45<br><br>VL<br>METPAQLLFLLLLWLPDTTGEIVLTQSPGTLSLSPGERAT<br>LSCRASQSVSSSYLAWYQQKPGQAPRLLIYGASSRATGIP<br>DRFSGSGSGTDFTLTISRLEPEDFAVYYCQQYGSWTFGQ<br>GTKVEIK<br>SEQ ID NO: 53 |
| 366.328. 10.63 | PTA-8789 | SYSMN SEQ ID NO: 63 | SITSGS YYIHY ADSVK G SEQ ID NO: 65 | ERGWG YYGMD V SEQ ID NO: 67 | RASQDI DSALA SEQ ID NO: 71 | DASSLE S SEQ ID NO: 73 | QQFNS YPYT SEQ ID NO: 75 | VH<br>MELGLRWVFLVAILEGVQCEVQLVESGGGLVKPGGSLR<br>LSCAASGFIFSSYSMNWVRQAPGKGLEWVSSITSGSYYIH<br>YADSVKGRFTISRDNAKNSLYLQMNSLRAEDTAVYYCV<br>RERGWGYYGMDVWGQGTTVTVSS<br>SEQ ID NO: 61<br><br>VL<br>MDMRVPAQLLGLLLLWLPGARCAIQLTQSPSSLSASVGD<br>RVTITCRASQDIDSALAWYQQKPGKAPKILIHDASSLESG<br>VPSRFSGSGSGTDFTLTISSLQPEDFATYYCQQFNSYPYTF<br>GQGTKLEIK<br>SEQ ID NO: 69 |
| 366.552. 11.31 | PTA-8787 | SDFWG SEQ ID NO: 79 | YISSRG STNYN- PSLKR SEQ ID NO: 81 | SAGVT DFDF SEQ ID NO: 83 | RASQGI SSWLA SEQ ID NO: 87 | VASSLQ S SEQ ID NO: 89 | QQANS FPLT SEQ ID NO: 91 | VH<br>MKHLWFFLLLVAAPRWVLSQVQLQESGPGLVKPSETLS<br>LTCTVSGGSISSDFWGWIRQPPGKGLEWIGYISSRGSTNY<br>NPSLKRRVTISVDTSRNQFSLKLSSVTAADTAVYYCARS<br>AGVTDFDFWGQGTLVTVSS<br>SEQ ID NO: 77<br><br>VL<br>MDMMVPAQLLGLLLLWFPGSRCDIQMTQSPSSVSASVG<br>DRVTITCRASQGISSWLAWYQHKPGKAPKLLIYVASSLQ<br>SGVPSRFSGSGSGTDFTLTISSLQPEDFATYYCQQANSFPL<br>TFGGGTKVEIK<br>SEQ ID NO: 85 |

1B: Expression of Clone 362.78.1.44 Immunoglobulin Heavy and Light Chain Genes in a Mammalian Cell Line to Produce 362.78-CHO Human anti-human IL-21 monoclonal antibody (derived from hybridoma clone 362.78.1.44) was expressed in CHO cells using two expression cassettes. The VH chain was fused to a modified human IgG1 constant region. The modified IgG1, IgG1.1, contained five amino acid substitutions to reduce effector functions. The human anti-human IL-21 heavy chain was linked to a dihydrofolate reductase (DHFR) selectable marker with an internal ribosomal entry site (IRES) sequence. The expression of the human anti-human IL-21 heavy chain and the DHFR selectable marker were directed by a constitutive synthetic promoter consisting of a fusion of the human cytomegalovirus (CMV) enhancer and the myeloproliferative sarcoma virus (MPSV) enhancer/promoter. The simian virus 40 (SV40) polyadenylation signal was used to terminate transcription at the end of the DHFR selectable marker. The VL chain was fused to the human immunoglobulin kappa constant region. The human anti-human IL-21 light chain was linked to a puromycin resistance (puroR) selectable marker with an IRES sequence. The expression of the human anti-human IL-21 light chain and the puroR selectable marker were directed by a constitutive synthetic promoter consisting of a fusion of the human CMV enhancer and the MPSV enhancer/promoter. The SV40 polyadenylation signal was used to terminate transcription at the end of the puroR selectable marker. The human anti-human IL-21 heavy and light chain expression cassettes were co-transfected into CHO DXB-11 host cells. Puromycin selection was followed by methotrexate selection to obtain high, stable expression of human anti-human IL-21 monoclonal antibody. The CHO-expressed version of IL-21 mAb clone 362.78.1.44 will be referred to in subsequent Examples as "362.78-CHO."

Example 2

Anti-IL-21 Monoclonal Antibodies Bind Human IL-21 Proteins and Peptides

2A. Binding and Neutralization of Peptides

The ability of the anti-human IL-21 binding and neutralizing monoclonal antibodies to bind to human IL-21, mutant human IL-21 protein, and human IL-21 sequence derived synthetic peptides was demonstrated in the Direct ELISA assay format.

The following peptides were used:

```
peptide #1                               ((SEQ ID NO: 3)
pyroGlu GQDRHMIRMRQLIDIVDQLKC;
```

```
peptide #2
                                              ((SEQ ID NO: 4))
NDLVPEFLPAPEDVETNC, peptide #3
                                              ((SEQ ID NO: 5))
NVSIKKLKRKPPSTNAGRRQKHRLTC, peptide #4
                                              ((SEQ ID NO: 6))
CDSYEKKPPKEFLERFKSLLQKMIHQHLS
and
```

Recombinant human IL-21 (SEQ ID NO: 2), human IL-21 sequence derived synthetic peptides:, and recombinant mutant human IL-21 (SEQ ID NO: 7) were separately immobilized onto the surface of 96 well polystyrene ELISA plates in a volume of 100 μL/well at a concentration of 1 μg/mL in Coating Buffer (0.1M Na$_2$CO$_3$, pH 9.6). Plates were incubated overnight at 4° C. after which unbound protein was aspirated and the plates washed twice with 300 μL/well of Wash Buffer (PBS-Tween defined as 0.137M NaCl, 0.0022M KCl, 0.0067M Na$_2$HPO$_4$, 0.0020M KH$_2$PO$_4$, 0.05% v/w polysorbate 20, pH 7.2). Wells were blocked with 200 μL/well of Blocking Buffer (PBS-Tween plus 1% w/v bovine serum albumin (BSA)) for 1 hour, after which the plates were washed twice with Wash Buffer. Antibody dilutions were prepared in 5% fetal bovine serum (FBS)/Iscove's Modified Dulbecco's Media (IMDM) medium and adjusted to 1 ug/ml. Duplicate samples of each antibody dilution were then transferred to the assay plates, 100 μL/well, in order to bind anti-human IL-21 proteins. Following 1 hour incubation at ambient temperature, the wells were aspirated and the plates washed twice as described above. Horseradish peroxidase (HRP) labeled Goat anti Mouse IgG, Fc specific or Goat anti Rat IgG, Fc specific, or Goat anti Human IgG, Fc specific (Jackson ImmunoResearch Laboratories, West Grove, Pa.) at a dilution of 1:5000 with 5% FBS/IMDM medium was then added to each well, 100 μL/well, and the plates incubated at ambient temperature for 1 hour. After removal of unbound HRP conjugated antibody, the plates were washed five times, 100 μL/well of tetra methyl benzidine (TMB) (BioFX Laboratories, Owings Mills, Md.) added to each well and the plates incubated for 3 minutes at ambient temperature. Color development was stopped by the addition of 100 μL/well of 450 nm TMB Stop Reagent (BioFX Laboratories, Owings Mills, Md.) and the absorbance values of the wells read on a Molecular Devices Spectra MAX 340 instrument at 450 nm.

TABLE 2

Monoclonal mouse anti-human IL-21 antibody reactivity to human IL-21 protein, mutant human IL-21 protein and human IL-21 sequence derived peptides

| Mouse Anti-human IL-21 Ab Clone # | Binding (B) Neutralizing (N) Isotype | Purified Ab Lot# | IL-21 | Peptide 1 | Peptide 2 | Peptide 3 | Peptide 4 | IL-21 mutant |
|---|---|---|---|---|---|---|---|---|
| 338.5.4 | B/N IgG1 | E10274 | +/− | 0 | 0 | 0 | 0 | +/− |
| 338.11.5 | B IgG1 | E10276 | +++ | 0 | +++ | 0 | 0 | +++ |
| 338.14.3 | B IgG1 | E10273 | +/− | 0 | 0 | 0 | 0 | 0 |
| 338.15.5 | B IgG1 | E10275 | +++ | 0 | 0 | 0 | +++ | 0 |
| 338.28.6 | B IgG1 | E10329 | +++ | 0 | 0 | 0 | 0 | + |
| 338.39.5 | B IgG1 | E10330 | +++ | 0 | 0 | +++ | 0 | +++ |

Reactivity:
None (0)
Weak (+)
Moderate (++)
Strong (+++)

TABLE 3

Monoclonal human anti-human IL-21 antibody reactivity to human IL-21 protein, mutant human IL-21 protein and human sequence derived peptides

| Human Anti-human IL-21 Ab Clone # | Binding(B) Neutralizing (N) Isotype | Purified Ab Lot# | IL-21 | Peptide 1 N-Term | Peptide 2 | Peptide 3 | Peptide 4 C-Term | IL-21 mutant |
|---|---|---|---|---|---|---|---|---|
| 362.75.1.1 | B/N IgG | E10364 | +++ | 0 | 0 | 0 | +++ | 0 |
| 362.78.1.44 | B/N IgG | E10554 | ++ | 0 | 0 | 0 | 0 | + |
| 362.597.3 | B/N IgG | E10366 | +++ | 0 | 0 | 0 | 0 | ++ |
| 366.328.10 | B/N IgG | E10416 | +++ | 0 | 0 | 0 | 0 | +++ |
| 366.345.6.11 | B IgG | E10476 | +++ | 0 | 0 | 0 | 0 | ++ |

TABLE 3-continued

Monoclonal human anti-human IL-21 antibody reactivity to human IL-21 protein, mutant human IL-21 protein and human sequence derived peptides

| Human Anti-human IL-21 Ab Clone # | Binding(B) Neutralizing (N) Isotype | Purified Ab Lot# | IL-21 | Peptide 1 N-Term | Peptide 2 | Peptide 3 | Peptide 4 C-Term | IL-21 mutant |
|---|---|---|---|---|---|---|---|---|
| 366.552.11 | B/N IgG | E10435 | +++ | 0 | 0 | 0 | ++ | 0 |

Reactivity:
None (0)
Weak (+)
Moderate (++)
Strong (+++)

2B Measurement of the Binding Affinities of Anti-Human IL-21 Monoclonal Antibody 362.78-CHO to Human IL-21 and Cynomolgus Monkey IL-21 by Surface Plasmon Resonance (Biacore)

The anti-IL-21 monoclonal antibody 362.78-CHO was evaluated for its binding affinity to human recombinant IL-21 and cynomolgus recombinant IL-21 using surface plasmon resonance.

Affinity Determination: Kinetic rate constants and equilibrium dissociation constants were measured for the interaction of the anti-human IL-21 monoclonal antibody 362.78-CHO with human IL-21 and cynomolgus IL-21 via surface plasmon resonance. The association rate constant ($k_a$ ($M^{-1}s^{-1}$)) is a value that reflects the rate of the antigen-antibody complex formation. The dissociation rate constant ($k_d$ ($s^{-1}$)) is a value that reflects the stability of this complex. By dividing the dissociation rate constant by the association rate constant ($k_d/k_a$) the equilibrium dissociation constant ($K_D$ (M)) is obtained. This value describes the binding affinity of the interaction. Antibodies with similar $K_D$ can have widely variable association and dissociation rate constants. Consequently, measuring both the $k_a$ and $k_d$ of antibodies helps to more uniquely describe the affinity of the antibody-antigen interaction.

Materials and Methods: Binding kinetics and affinity studies were performed on a Biacore T100™ system (GE Healthcare, Piscataway, N.J.). Methods for the Biacore T100™ were programmed using BIACORE T100™ Control Software, v 1.1.1. For these experiments, the 362.78-CHO antibody was either captured onto a CM4 sensor chip via a goat anti-human IgG Fc-gamma antibody (Jackson ImmunoResearch, West Grove, Pa.), or it was minimally biotinylated with a 1:100 mass ratio of Sulfo-NHS-LC-Biotin (Pierce, Rockford, Ill.) in a buffer of PBS pH 7.4 then captured onto a streptavidin (SA) chip. All binding experiments were performed at 25° C. in a buffer of 10 mM HEPES, 300 mM NaCl, 5 mM $CaCl_2$, 0.05% Surfactant P20 (Biacore), 1 mg/mL bovine serum albumin, pH 8.0.

For the experiments with the goat anti-human IgG Fc-gamma antibody, the capture antibody was diluted to concentration of 50 µg/mL in 10 mM sodium acetate pH 5.0, and then covalently immobilized to all four flow cells of a CM4 sensor chip using amine coupling chemistry (EDC:NHS). After immobilization of the antibody, the remaining active sites on the flow cell were blocked with 1 M ethanolamine A capture antibody density of approximately 3500 RU was obtained. The anti-IL-21 antibody 362.78-CHO was captured onto flow cell 2, 3, and 4 of the CM4 chip at three different densities (ranging from 25 to 150 RU). Capture of the 362.78-CHO antibody to the immobilized surface was performed at a flow rate of 10 µL/min. The Biacore instrument measures the mass of protein bound to the sensor chip surface, and thus, capture of the test antibody was verified for each cycle. Serial dilutions of human recombinant IL-21 or cynomolgus recombinant IL-21 (ZymoGenetics) were prepared from 40 nM-0.003 nM (1:5 serial dilutions). The serial dilutions were injected over the surface and allowed to specifically bind to the 362.78-CHO antibody captured on the sensor chip. Duplicate injections of each IL-21 antigen concentration were performed with an association time of either 6.5 or 7 minutes and dissociation time of either 10, 15, or 60 minutes. Kinetic binding studies were performed with a flow rate of 50 µL/min. In between cycles, the flow cell was washed with 20 mM hydrochloric acid to regenerate the surface. This wash step removed both the captured test antibody and any bound antigen from the immobilized antibody surface. The 362.78-CHO antibody was subsequently captured again in the next cycle.

For the experiments with the minimally biotinylated 362.78-CHO, the biotinylated antibody was captured onto flow cell 2, 3, and 4 of the SA chip at three different densities (ranging from 150 to 1200 RU). Capture of the biotinylated-362.78-CHO antibody to the surface was performed at a flow rate of 10 µL/min. Serial dilutions of human recombinant IL-21 or cynomolgus recombinant IL-21 (ZymoGenetics) were prepared either from 50 nM-0.001 nM (1:4 serial dilutions) or from 40 nM-0.003 nM (1:5 serial dilutions). These serial dilutions were injected over the surface and allowed to specifically bind to the 362.78-CHO antibody captured on the sensor chip. Duplicate injections of each IL-21 antigen concentration were performed with an association time of either 6.5 or 7 minutes and dissociation time of either 10, 15, or 60 minutes. Kinetic binding studies were performed with a flow rate of 50 µL/min. In between cycles, the flow cell was washed with 20 mM hydrochloric acid to regenerate the surface. This wash step removed any bound antigen from the immobilized antibody surface. The wash cycle did not remove the biotinylated 362.78-CHO antibody from the sensor surface, and the antibody was subsequently available to bind the next antigen sample.

Data was compiled using the BIACORE T100™ Evaluation software (version 1.1.1). Data was processed by subtracting reference flow cell and blank injections. Baseline stability was assessed to ensure that the regeneration step provided a consistent binding surface throughout the sequence of injections. Duplicate injection curves were checked for reproducibility. Based on the binding of the monovalent IL-21 to a bivalent antibody, the 1:1 binding interaction model was determined to be appropriate. The reference-subtracted binding curves from three flow cells (FC2-1, FC3-1, FC4-1) were globally fit to the 1:1 binding model with a multiple Rmax and with the RI set to zero. The data fit well to the 1:1 binding model with good agreement between the experimental and theoretical binding curves. The $chi^2$ and standard errors associated the fits were low. There was no trending in the residuals.

Results: For the interaction of 362.78-CHO with human IL-21, data was compiled from four separate experiments. The $k_a$ of the multiple experiments ranged from 3E+07 to 5+07 ($M^{-1}s^{-1}$), while the $k_d$ ranged from 3E−06 to 3E−05 ($s^{-1}$). The calculated $K_D$ ranged from 0.9E−13 to 8E−13 (M).

For the interaction of 362.78-CHO with cynomolgus IL-21, data was compiled from three separate experiments. The $k_a$ was 3E+07 ($M^{-1} s^{-1}$) for each experiment, while the $k_d$ ranged from 2E−04 to 5E−04 ($s^{-1}$). The calculated $K_D$ ranged from 0.9E−11 to 2E−11 (M).

Example 3

Species Cross Reactivity Experiments

Determination of ability of anti-human IL-21 antibodies to cross-react and bind murine or cynomolgous monkey IL-21 protein or human IL-21 sequence derived synthetic peptides Species cross-reactivity studies can be important to demonstrate specificity for therapeutic antagonist development strategies. In order to determine whether the anti-human IL-21 binding and neutralizing entities described herein may cross-react and bind to murine or cynomolgus IL-21 (and therefore, justify the cynomolgus monkey or mouse as a viable test species), it was necessary to demonstrate comparable binding of the antibodies to recombinant human, murine and cynomolgous monkey IL-21 in the various assay formats. One of the methods for testing binding of the monoclonal antibodies is by their performance in immunoblot (Western blot) assays. Recombinant human IL-21 (SEQ ID NO:2), recombinant murine IL-21 (SEQ ID NO:11), recombinant cynomolgus IL-21 (SEQ ID NO:9), human IL-21 sequence derived synthetic peptides: peptide #1 pyr30-K50 (Seq ID 3), peptide #2 N54-C71 (SEQ ID NO:4), peptide #3 N97-C122 (Seq ID NO:5), peptide #4 C125-5153 (SEQ ID NO:6) conjugated to ovalbumin, or an irrelevant control cytokine, recombinant human IFN-λ (ZymoGenetics) were submitted to sodium dodecyl sulfate-polyacrylamide gel electrophoresis (SDS-PAGE) using 4-12% BisTris polyacrylamide gels (Invitrogen, Inc.) and transferred to nitrocellulose membranes using standard methods and a buffer containing 25 mM Tris, 186 mM glycine and 40% methanol.

For Western blots, the non-specific sites on the membranes were blocked with a buffer containing 20 mM Tris, pH 7.4, 0.5 mM EDTA, 0.5% IGEPAL CA-630, 150 mM NaCl, 0.25% gelatin, and 1% casein hydrolysate blocking solution (Western Blocking Reagent, Roche Diagnostics, Inc., Basel Switzerland) (Blocking Buffer). The membranes were then incubated for 2 hrs at room temperature with purified monoclonal antibody (10 ng/ml or 100 ng/ml) in the Blocking Buffer followed by a 2 hr incubation with peroxidase conjugated donkey anti-human IgG (Jackson Laboratories, Bar Harbor, Me.). The membranes were washed 5 times with the Tris/EDTA/IGEPAL/NaCl/gelatin Blocking buffer which lacked the casein hydrolysate and developed with SUPERSIGNAL™ DuraWest Luminol/Enhancer/Peroxidase Solution (Pierce, Rockford, Ill.) for chemoluminescence detection. The blots were visualized using X-ray film based standard methods.

TABLE 4

Monoclonal Human Anti-Human IL-21 Antibody Reactivity in Western Blot Analysis

| Clone* | Hu IL-21 | Cyno IL-21 | Mu IL-21 | +Hu IL-21 Peptide A1744 | +Hu IL-21 Peptide A1750 | +Hu IL-21 Peptide A1751 | +Hu IL-21 Peptide A1752 |
|---|---|---|---|---|---|---|---|
| 362.35.1.2 | 0 | 0 | 0 | 0 | 0 | 0 | 0 |
| 362.37.3 | +++ | +++ | +++ | 0 | 0 | 0 | 0 |
| 362.75.1.1 | +++ | +++ | +++ | 0 | 0 | 0 | +++ |
| 362.78.1 | ++ | ++ | 0 | 0 | 0 | 0 | 0 |
| 362.108.1.2 | 0 | 0 | 0 | 0 | 0 | 0 | 0 |
| 362.172.2 | +++ | +++ | +++ | 0 | 0 | 0 | 0 |
| 362.216.2 | 0 | +/− | 0 | 0 | 0 | 0 | 0 |
| 362.256.1 | 0 | 0 | 0 | 0 | 0 | 0 | 0 |
| 362.303.1.1 | 0 | 0 | 0 | 0 | 0 | 0 | 0 |
| 362.378.1 | +++ | +++ | +++ | 0 | 0 | 0 | + |
| 362.468.3 | +/− | + | 0 | 0 | 0 | 0 | 0 |
| 362.564.1.4 | ++ | ++ | 0 | 0 | 0 | 0 | 0 |
| 362.597.3 | ++ | ++ | +/− | 0 | 0 | 0 | 0 |
| 362.632.2 | +++ | +++ | +++ | 0 | 0 | 0 | +++ |
| 366.328.10 | + | + | 0 | 0 | 0 | 0 | 0 |
| 366.342.8 | +++ | +++ | +++ | 0 | 0 | 0 | 0 |
| 366.345.6.11 | 0 | 0 | 0 | 0 | 0 | 0 | 0 |
| 366.353.11.12 | + | ++ | 0 | 0 | 0 | 0 | 0 |
| 366.398.36 | +++ | +++ | +++ | 0 | 0 | 0 | 0 |
| 366.453.30 | +++ | +++ | +++ | 0 | 0 | 0 | 0 |
| 366.462.24.10 | +++ | +++ | +++ | 0 | 0 | 0 | 0 |
| 366.479.13 | +++ | +++ | +++ | 0 | 0 | 0 | 0 |
| 366.552.11 | +++ | +++ | +++ | 0 | 0 | 0 | 0 |
| 366.565.7 | 0 | 0 | 0 | 0 | 0 | 0 | 0 |
| 366.617.7 | +++ | +++ | +++ | 0 | 0 | 0 | 0 |
| 366.618.20 | ++ | ++ | + | 0 | 0 | 0 | 0 |
| 367.752.5 | +++ | +++ | +++ | 0 | 0 | 0 | 0 |
| 368.626.24 | +++ | +++ | ++ | 0 | 0 | 0 | 0 |

Reactivity:
None (0)
Weak (+)
Moderate (++)
Strong (+++)
*No Signals Observed with IFN-λ
+Peptides were Conjugated to Ovalbumin

Example 4

Evaluation of the Ability of Anti-Human IL-21 Antibodies to Cross-React and Bind the Human γc-Family Cytokines IL-2, IL-4, IL-7, IL-9, IL-15

Another important characteristic of a specific antibody is the ability of the antibody to bind to and antagonize the target protein(s) but to not bind related proteins (non-target) to a significant degree. The ability of anti-human IL-21 antibodies to bind to related cytokines was tested in the Western blot format. Samples of all members of the γc-cytokine family were obtained and run on SDS-PAGE and transferred to nitrocellulose membranes for blotting. Recombinant human IL-2 (202-IL/CF), human IL-4 (204-IL/CF), human IL-7 (207-IL/CF), human IL-9 (209-IL/CF), human IL-15 (247-IL/CF) all obtained from R&D Systems, Minneapolis Minn.), human IL-21 (ZymoGenetics) and human IFN-λ (U.S. Pat. Nos. 6,927,040; 7,252,969) were used to evaluate the specificity of the antibodies. All of the antibodies tested showed no detectable binding above background to the γc-family cytokines except for human IL-21 where clear binding was observed, consistent with previous Western blots using these antibodies (see Example 3).

TABLE 5

Monoclonal Anti-Human IL-21 Antibody Reactivity to γc cytokines in Western Blot Analysis

| Clone | Hu IL-2 | Hu IL-4 | Hu IL-7 | Hu IL-9 | Hu IL-15 | Hu IL-21 | Hu IFNλ negative control |
|---|---|---|---|---|---|---|---|
| 362.597.3 | 0 | 0 | 0 | 0 | 0 | ++ | 0 |
| 362.75.1.1 | 0 | 0 | 0 | 0 | 0 | +++ | 0 |
| 362.78.1 | 0 | 0 | 0 | 0 | 0 | + | 0 |
| 362.564.1.4 | 0 | 0 | 0 | 0 | 0 | ++ | 0 |
| 366.328.10.63 | 0 | 0 | 0 | 0 | 0 | ++ | 0 |
| 366.552.11.31 | 0 | 0 | 0 | 0 | 0 | +++ | 0 |
| 366.617.7 | 0 | 0 | 0 | 0 | 0 | +++ | 0 |

Reactivity:
None (0)
Weak (+)
Moderate (++)
Strong (+++)

TABLE 6

Monoclonal Mouse and Rat Anti-Human L-21 Antibody Reactivity in Western Blot Analysis

| Clone* | Hu IL-21 | Cyno IL-21 | Mu IL-21 | +Hu IL-21 Peptide A1744 | +Hu IL-21 Peptide A1750 | +Hu IL-21 Peptide A1751 | +Hu IL-21 Peptide A1752 |
|---|---|---|---|---|---|---|---|
| Mouse Clones | | | | | | | |
| 338.5.4 | 0 | 0 | 0 | 0 | 0 | 0 | 0 |
| 338.11.5 | +++ | +++ | +/− | 0 | +++ | 0 | 0 |
| 338.14.3 | + | + | 0 | 0 | 0 | 0 | 0 |
| 338.15.5 | +++ | +++ | ++ | 0 | 0 | 0 | +++ |
| 338.17.3 | +++ | ++ | + | 0 | 0 | ++ | 0 |
| 338.24.5 | +++ | + | 0 | 0 | 0 | ++ | 0 |
| 338.25.6 | +++ | +++ | +++ | 0 | 0 | 0 | 0 |
| 338.28.6 | +/− | 0 | 0 | 0 | 0 | 0 | 0 |
| 338.29.2 | +++ | +++ | 0 | +++ | 0 | 0 | 0 |
| 338.39.5 | +++ | +++ | 0 | 0 | 0 | 0 | 0 |
| Rat Clones | | | | | | | |
| 272.19.1.1.4.2 | +++ | +++ | +++ | ++ | 0 | 0 | 0 |
| 272.21.1.3.4.2 | +++ | +++ | + | 0 | 0 | 0 | 0 |

Reactivity:
None (0)
Weak (+)
Moderate (++)
Strong (+++)
*No Signals Observed with IFN-λ
+Peptides were Conjugated to Ovalbumin

Example 5

Competitive Epitope Binning Studies

Epitope binning experiments were performed to determine which anti-IL-21 monoclonal antibodies are capable of binding simultaneously to human IL-21. Both human and mouse antibodies were represented. Anti-IL-21 monoclonal antibodies that compete for the same, or an overlapping, binding site (epitope) on the antigen are not able to bind simultaneously and are functionally grouped into a single family or "epitope bin". Anti-IL-21 monoclonal antibodies that do not compete for the same binding site on the antigen are able to bind simultaneously and are grouped into separate families or "epitope bins". Experiments were performed using a BIACORE T100™ instrument. Epitope binning experiments were performed with soluble, (ZymoGenetics) human IL-21 as the antigen.

Epitope binning studies were performed on a BIACORE T100™ system (GE Healthcare, Piscataway, N.J.). Methods were programmed using BIACORE T100™ Control Software, v 1.1.1. Individual anti-IL-21 monoclonal antibodies were covalently immobilized to separate flow cells of a BIACORE CM4 sensor chip. Subsequently, the IL-21 antigen was injected and allowed to specifically bind to the monoclonal antibody immobilized on the sensor chip. The BIACORE instrument measures the mass of protein bound to the sensor chip surface, and thus, immobilization of the primary antibody of a test pair and specific binding of the IL-21 antigen to the primary antibody were verified for each test cycle. Following the binding of the IL-21 antigen, a secondary anti-IL-21 monoclonal antibody was injected and allowed to bind. If the secondary anti-IL-21 monoclonal antibody was capable of binding the antigen simultaneously with the primary monoclonal antibody, an increase in mass on the surface of the chip, or binding, was detected. If, however, the secondary anti-IL-21 monoclonal antibody was not capable of binding the antigen simultaneously with the primary monoclonal antibody, no additional mass, or binding, was detected. Each anti-IL-21 monoclonal antibody tested against itself was used as the negative control to establish the level of the background (no-binding) signal.

A series of experiments was completed to test the binding properties of purified anti-IL-21 monoclonal antibodies obtained from hydridoma fusions of the spleens of mice immune to human IL-21. The first anti-IL-21 monoclonal antibody of a test pair was covalently immobilized using EDC:NHS to a density of approximately 1000 RU. The IL-21 antigen was diluted to 100 nM and allowed to flow over the surface of the immobilized antibody. Subsequently, the secondary antibody of a test pair was diluted to 5 µg/mL (approximately 32.2 nM) and allowed to bind to the captured IL-21 antigen. A subset of the anti-IL-21 monoclonal antibodies was tested as the primary antibody in combination with the full panel of secondary anti-IL-21 monoclonal antibodies. Binding experiments were performed with a flow rate of 30 µL/min at 25° C. The buffer for these studies consisted of 10 mM Hepes, 0.3 M NaCl, 0.05% surfactant P20, 5 mM $CaCl_2$, 1 mg/mL bovine serum albumin, pH 8.0. Between cycles, the antibody on the chip was regenerated with 20 mM hydrochloric acid. Data was compiled using BIACORE T100™ Evaluation software (version 1.1.1), then loaded into EXCEL™ for additional data processing.

Purified anti-IL-21 monoclonal antibodies were characterized and assigned into epitope bins. The signal (RU, response units) reported by the BIACORE is directly correlated to the mass on the sensor chip surface. Once the level of background signal (RU) associated with the negative controls was established (the same anti-IL-21 monoclonal antibody used as both the primary and secondary antibody), the binning results were reported as either positive or negative binding. Positive binding indicates that two different anti-IL-21 monoclonal antibodies are capable of binding the antigen simultaneously. Negative binding indicates that two different anti-IL-21 monoclonal antibodies are not capable of binding the antigen simultaneously. The differential between positive and negative response values in this experiment was significant and allowed for an unambiguous assignment of the anti-IL-21 monoclonal antibodies into six distinct families, or epitope bins. The first epitope bin was represented by anti-IL-21 monoclonal antibodies from, for example, clones 338.5.4; 362.78.1; and 362.597.3. The second bin was represented by anti-IL-21 monoclonal antibodies from, for example, clones 338.14.3; 362.75.1.1; and 366.328.10. An additional third bin was found to overlap the binding epitopes of the bin #1 and bin #2 antibodies. It was represented by monoclonal antibody from, for example, clone 366.552.11. Antibodies that neutralize IL-21 are found in each of these three bins.

Three additional epitope bins were identified. Each of these bins was represented by monoclonal antibody from, for example, hybridoma clones 366.345.6.11 (bin#4), 338.28.6 (bin#5), and 338.39.5 (bin#6). The antibodies identified in these three bins do not neutralize human IL-21 bioactivity.

Example 6

Soluble Receptor Competition Studies

Competition experiments were performed to determine which anti-human IL-21 monoclonal antibodies are capable of binding IL-21 simultaneously with the IL-21 soluble receptor. Anti-human IL-21 monoclonal antibodies that compete with the soluble receptor for the same, or an overlapping, binding site (epitope) on the antigen are not able to bind simultaneously. Anti-IL-21 monoclonal antibodies that do not compete with the soluble receptor for the same binding site on the antigen are able to bind simultaneously. Competition experiments were performed with soluble, recombinant human IL-21 as the antigen. The IL-21 antigen was allowed to bind the monoclonal antibody prior to competition with the IL-21 soluble receptor. Two versions of the IL-21 soluble receptor (both produced by ZymoGenetics) were utilized for monoclonal antibody analysis in these studies: One version of the receptor consists of a homodimeric receptor (IL-21R-Fc) composed of the extracellular domain of the IL-21 receptor fused to an Fc molecule derived from human immunoglobulin. The second soluble receptor form was a heterodimeric receptor (IL-21R/γc-Fc) composed of one subunit comprising the extracellular domain of the IL-21 receptor fused to an Fc molecule derived from human immunoglobulin and a second subunit comprising the extracellular domain of the common γcommon-chain fused to an Fc molecule derived from human immunoglobulin, as described in co-owned U.S. Pat. No. 6,777,539 incorporated by reference herein in its entirety.

Competition studies were performed on a BIACORE T100™ system (GE Healthcare, Piscataway, N.J.). Methods were programmed using BIACORE T100™ Control Software, v 1.1.1. Individual anti-IL-21 monoclonal antibodies were covalently immobilized to separate flow cells of a BIACORE CM4 sensor chip. Subsequently, the IL-21 antigen (SEQ ID NO: 2) was injected and allowed to specifically bind to the monoclonal antibody immobilized on the sensor chip. The Biacore instrument measures the mass of protein bound to the sensor chip surface, and thus, immobilization of the primary antibody and specific binding of the IL-21 antigen to the primary antibody were verified for each test cycle. Following the binding of the IL-21 antigen, the soluble receptor was injected and allowed to bind. If the soluble receptor was capable of binding the antigen simultaneously with the primary monoclonal antibody, an increase in mass on the surface of the chip, or binding, was detected. If, however, the soluble receptor was not capable of binding the antigen simultaneously with the primary monoclonal antibody, no additional mass, or binding, was detected. Each anti-IL-21 monoclonal antibody tested against itself was used as the negative control to establish the level of the background (no-binding) signal. As a positive control, each anti-IL-21 monoclonal antibody was tested against an anti-IL-21 antibody from a different epitope bin to determine the level of positive (binding) signal.

A series of experiments were completed to test the binding properties of 5 purified anti-IL-21 monoclonal antibodies (from hybridoma clones 362.78.1, 366.75.1.1, 366.328.10, 366.552.11.31, and 366.345.6.11) that bind human IL-21. The first anti-IL-21 monoclonal antibody of a test pair was covalently immobilized using a mixture of 0.4 M EDC [N-ethyl-N'-(3-diethylamino-propyl) carbodiimide] and 0.1 M NHS(N-hydroxysuccinimide) to a density of approximately 1000 RU. After immobilization of the antibody, the active sites on the flow cell were blocked with 1M ethanolamine. The IL-21 antigen was diluted to 100 nM and allowed to flow over the surface of the immobilized antibody. Subsequently, the soluble receptor was diluted to 10 µg/mL and allowed to bind to the captured IL-21 antigen. Binding experiments were performed with a flow rate of 30 µL/min at 25° C. The buffer for these studies consisted of 10 mM Hepes, 0.3 M NaCl, 0.05% surfactant P20, 5 mM $CaCl_2$, 1 mg/mL bovine serum albumin, pH 8.0. Between cycles, the flow cell was washed with 20 mM hydrochloric acid to regenerate the surface. This wash step removed the IL-21 antigen and any bound soluble receptor from the immobilized antibody surface, and allowed for the subsequent binding of the next test sample. Data was compiled using BIACORE T100™ Evaluation software (version 1.1.1).

Purified anti-IL-21 monoclonal antibodies were characterized for their ability to compete with the human IL-21 soluble receptor for binding to the IL-21 antigen. The signal (RU, response units) reported by the BIACORE is directly correlated to the mass on the sensor chip surface. Once the level of background signal (RU) associated with the negative controls was established (the same anti-IL-21 monoclonal antibody used as both the primary and secondary antibody), the competition results were reported as either positive or negative binding. Positive binding indicates that the anti-IL-21 monoclonal antibody and IL-21 soluble receptor are capable of binding the antigen simultaneously. Negative binding indicates that the anti-IL-21 monoclonal antibody and the IL-21 soluble receptor are not capable of binding the antigen simultaneously. The differential between positive and negative response values in this experiment was significant and allowed for an unambiguous determination of competition between the anti-IL-21 monoclonal antibodies and IL-21 soluble receptor.

Monoclonal antibodies from hybridoma clones 362.78.1 and 366.552.11.31 competed with both versions of the IL-21 soluble receptor (homodimeric IL-21R-Fc and heterodimeric IL-21R/γc-Fc) for binding to the human IL-21 antigen. Monoclonal antibodies from hybridoma clones 366.328.10 and 366.345.6.11 did not compete with either version of the soluble receptor for binding to the antigen. The monoclonal antibody from hybridoma clone 362.75.1.1 showed partial competition for binding with both forms of the soluble receptor. These studies were performed with the IL-21 antigen pre-bound to the monoclonal antibody. Three of these antibodies (362.78.1, 366.328.10, 366.552.11.31) have been shown to neutralize human IL-21 while the monoclonal antibody antibodies from hybridoma clones 362.75.1.1 and 366.345.6.11 are, depending on the assay, very weak, or non-neutralizers of human IL-21 bioactivity.

Example 7

IL-21 Baf3/huIL-21R STAT3 Bioactivity Assay

The following phosphorylated-STAT3 bioassay was used as a primary screen to measure neutralizing anti-IL-21 titers in murine serum as well as relative levels of IL-21 neutralization by hybridoma supernatants and purified anti-IL-21 antibodies. IL-21 activity was determined by measuring the level of STAT3-phosphorylation following ligand-receptor interaction in Baf3/KZ134/huIL-21R cells (see Spolski and Leonard, *Annu Rev Immunol*. Nov. 8; 2007). Relative neutralization activity was determined based on the decrease in phosphorylated-STAT3 levels using an $EC_{50}$ concentration of IL-21 and a titration of antagonist.

Baf3/KZ134/huIL-21R cells were washed two times with assay media (RPMI 1640 with 5% fetal bovine serum, 1× Glutamax, 1% Sodium Pyruvate, and 2 µM β-Mercaptoethanol; all from Invitrogen, Carlsbad, Calif.) before being plated out at 40,000 cells/well in 96-well, round-bottom tissue culture plates (Becton Dickinson, Franklin Lakes, N.J.). Cells were placed in a 37° C. tissue culture incubator while the test solutions were prepared. To determine $EC_{50}$ and $EC_{90}$ concentrations of IL-21 in this assay, serial dilutions of recombinant human IL-21 were prepared in assay media and plated in a separate 96-well U-bottom plate. Alternatively, to test for IL-21 neutralization, an $EC_{50}$ concentration of IL-21 (determined to be 33 µM) was preincubated with serial dilutions of IL-21-immunized mouse serum, spent hybridoma media, purified soluble human IL-21R/γc-Fc or purified monoclonal anti-IL-21 antibodies. Both the cell plate and the solution plate were then incubated in a humidified tissue culture chamber to equilibrate for 30 minutes at 37° C. and 5% $CO_2$. After 30 minutes, the reaction was initiated by transferring the IL-21 solutions to the cell plate and incubating for 10 minutes at 37° C. and 5% $CO_2$.

Following the 10 minute incubation, reactions were stopped by placing the plate on ice and adding 125 µL of ice-cold Cell Wash Buffer (BIO-PLEX Cell Lysis Kit, BIO-RAD Laboratories, Hercules, Calif.) to each well. Cells were then spun down at 1500 rpm at 4° C. for 5 minutes and the media aspirated. To lyse the cells, 50 µL/well Lysis Buffer (prepared according to the manufacturer's instructions, BIO-RAD Labs) was added to each well. The cell lysates were then pipetted up and down five times while on ice, and agitated on a microplate platform shaker for 20 minutes at 600 rpm at 4° C. Plates were then centrifuged at 3000 rpm at 4° C. for 20 minutes. Supernatants were collected and transferred to a new micro titer plate and mixed 1:1 with Assay Buffer (BIO-RAD) for storage at −20° C.

Capture beads (BIO-PLEX Phospho-STAT3 Assay, BIO-RAD Laboratories) were diluted and plated in a 96-well filter plate (Millipore Corporation, Ireland) according to manufacturer's instructions. Plates were washed two times with Wash Buffer (BIO-RAD) and 50 µL of cell lysate mix was transferred to each well. Each plate was then wrapped in aluminum foil and shaken overnight at room temperature and 300 rpm. The following day, the plate was transferred to a microtiter vacuum apparatus and washed two times with Wash Buffer. After addition of 25 µL/well detection antibody (BIO-RAD), the foil-covered plate was incubated at room temperature for 30 minutes with shaking at 300 rpm. The plate was filtered and washed two times with wash buffer. Streptavidin-PE (BIO-RAD; 50 µL/well) was added, and the foil-covered plate was incubated at room temperature for 15 minutes with shaking at 300 rpm. The plate was filtered and washed two times and resuspended in 125 µL/well Bead Resuspension Buffer (BIO-RAD). The level of phosphorylated-STAT3 was then assessed using an array reader (BIO-PLEX, BIO-RAD Laboratories) according to the manufacturer's instructions. Data were analyzed using analytical software (BIO-PLEX MANAGER 3.0, BIO-RAD Laboratories). Increases in the level of the phosphorylated STAT3 transcription factor present in the lysates were indicative of an IL-21 receptor-ligand interaction. For the neutralization assay, decreases in the level of the phosphorylated STAT3 transcription factor present in the lysates were indicative of neutralization of the IL-21 receptor-ligand interaction. $IC_{50}$ (concentration of antagonist that yields 50 percent inhibition of ligand activity) values were calculated using GraphPad Prism®4 software (GraphPad Software, Inc., San Diego Calif.) and expressed as molar concentrations for each reagent in the neutralization assay.

Human IL-21 induced STAT3 phosphorylation in a dose dependent manner with an $EC_{50}$ concentration determined to be approximately 33 pM. Table 7 summarizes the $IC_{50}$ values for the positive control (soluble human IL-21R/γc-Fc fusion protein) and the IL-21 neutralizing entities described herein. These data indicate that the IL-21 neutralizing antibodies were active and were equal to or better than the positive control at reducing IL-21-induced STAT3 phosphorylation.

TABLE 7

$IC_{50}$ Values in STAT3-Phosphorylation Assay

| | $IC_{50}$ (pM) Expt #1 | $IC_{50}$ (pM) Expt #2 | $IC_{50}$ (pM) Expt #3* |
|---|---|---|---|
| soluble hIL-21R/γc-Fc | 25 | 102 | 140.2 |
| IL-21 mAb Clone # | | | |
| 362.75.1 | No Neut. | | |
| 362.78.1 | 14 | 60 | |
| 362.78.1.44 | | 41 | 66.7 |
| 362.78-CHO (A2162F) | | | 42.0 |
| 366.328.10.63 | 210 | | |
| 366.552.11.31 | 59 | | |
| 366.617.7 | 69 | | |
| 366.345.6.11 | Weak | | |

*Expt 3 conducted using 96 pM IL-21

Example 8

IL-21 Baf3/huIL-21R STAT-Luciferase Bioactivity Assay

This 24-hour assay measures IL-21-induced STAT-Luciferase activity in Baf3/KZ134/huIL-21R transfected cells. Baf3/KZ134/huIL-21R transfected cells were washed two times with assay media (phenol red-free RPMI 1640 with 5% fetal bovine serum, 1× Glutamax, 1% Sodium Pyruvate, and 2 μM β-Mercaptoethanol; all from Invitrogen, Carlsbad, Calif.) before being plated out at 40,000 cells/well in a 96-well, flat-bottom opaque white culture plates (Corning/Costar, Lowell, Mass.). Cells were then placed in a tissue culture incubator while the test solutions were prepared. In a separate plate, human IL-21 was mixed with either media or a range of IL-21 antagonists (either monoclonal antibodies or the soluble human IL-21 receptor/γc-Fc). Once mixed, this plate was also transferred to a humidified 37° C. tissue culture incubator. After 30 minutes the test solutions were transferred to the cell plate and mixed. This plate was then placed back in the incubator for 24 hours. After 24 hours, the cells were removed from the incubator and allowed to cool to room temperature. Each well was then diluted 1:1 with a 100 μL volume of Steady-Glo Luciferase reagent (Promega, Madison, Wis.) and mixed thoroughly. The plate was covered and shaken at room temperature for 10 minutes and Relative Luciferase Units (RLU) were measured on a luminometer.

To determine $EC_{50}$ and $EC_{90}$ concentrations of IL-21 in this assay, serial dilutions of recombinant human IL-21 ranging from 0 to 100 ng/mL were tested. The $EC_{90}$ concentration of IL-21, ~15 ng/mL (961 pM), was used in subsequent neutralization experiments. In these experiments, clones 362.78.1 (and its subclone 362.78.1.44 and CHO-expressed counterpart, 362.78-CHO; see Example 1) and 362.328.10.63 demonstrated the most potent anti-IL-21 activity, with $IC_{50}$ concentrations in the range of 300-850 pM, while the $IC_{50}$ values for the soluble human IL-21 receptor/γc-Fc control ranged from 650-1830 pM. The relative activities of the neutralizing entities described herein are summarized in Table 8.

TABLE 8

$IC_{50}$ Values in 24 hr STAT-Luciferase Assay

|  | $IC_{50}$ (pM) Expt #1 | $IC_{50}$ (pM) Expt #2 | $IC_{50}$ (pM) Expt #3 |
|---|---|---|---|
| Soluble hIL-21R/γc-Fc | 650-850 | 1830 |  |
| IL-21 mAb Clone# |  |  |  |
| 362.75.1 | No Neut. |  |  |
| 362.78.1 | 400 | 775 | 760 |
| 362.78.1.44 |  | 850 |  |
| 362.78CHO (A2162F) |  |  | 533 |
| 366.328.10.63 | 300-500 |  |  |
| 366.552.11 | 2400 |  |  |
| 366.617.7 | 6360 |  |  |
| 366.345.6.11 | 3184 |  |  |

Example 9

Cross-Reaction to Cynomolgus Monkey, Murine or Rat IL-21 Activity

Species cross-reaction studies (especially for non-human primate cross-reactivity) are important to complete prior to pre-clinical pharmacology/toxicology studies when developing a therapeutic antagonist. In order to determine whether the anti-human IL-21 neutralizing entities described herein might cross-react and neutralize the activity induced by cynomolgus IL-21, murine IL-21 or rat IL-21(and therefore, justify either cynomolgus monkeys, mice and/or rats as viable test species), it was first necessary to demonstrate recombinant cynomolgus, murine and rat IL-21 bioactivity. The methods for IL-21 STAT-Luciferase activity assays described in Example 8 were used to determine $EC_{50}$ and $EC_{90}$ values for recombinant human IL-21, cynomolgus IL-21, murine IL-21, and rat IL-21 (all produced at ZymoGenetics). Results indicate that the levels of STAT-Luciferase activity induced by the human, cynomolgus and murine IL-21 in this assay differ widely. $EC_{90}$ values used in subsequent experiments were determined to be as follows: 961 pM for human IL-21; 102 pM for cynomolgus monkey IL-21; 6.41 nM for mouse IL-21, and 1.08 nM for rat IL-21. IL-21 soluble receptor (hIL-21R/γc-Fc) neutralized the effects of cynomolgus, murine and rat.

IL-21. Addition of the purified anti-IL-21 monoclonal antibodies shown in Table 9 neutralized cynomolgus IL-21 to varying degrees but did not neutralize murine or rat IL-21 (note that only 362.78-CHO and 366.552.11 were tested against rat IL-21). The $IC_{50}$ values for neutralization of cynomolgus IL-21 by the neutralizing entities described herein ranged from ~100 pM to 431 pM and are summarized in Table 9. It should be noted that the best human IL-21 neutralizing antibodies were all able to effectively neutralize cynomolgus IL-21 but not murine IL-21 or rat IL-21. Additionally, the CHO-cell produced IL-21 mAb (362.78-CHO) was tested in a separate experiment using an 800 pM concentration of cynomolgus monkey IL-21.

TABLE 9

Cross-reaction of hIL-21 antagonists to cynomolgus monkey, murine and rat IL-21 in the STAT-Luciferase assay.

|  | Cyno IL-21 $IC_{50}$ ([cIL-21] = 100 pM) | | Murine IL-21 IC50 ([mIL-21] = 6.41 nM) | | Rat IL-21 $IC_{50}$ ([rIL-21] = 1.08 nM) | |
|---|---|---|---|---|---|---|
|  | ng/mL | Molar conc. | ng/mL | Molar conc. | ng/mL | Molar conc. |
| soluble hIL-21R/γc-Fc | 20 | 385 pM | 425.8 | 8.06 nM | 707.5 | 13.4 nM |
| IL-21 mAb Clone: |  |  |  |  |  |  |
| 362.75.1 | weak | — | none | none | N/T | N/T |
| 362.78.1 | 60 | 400 pM | none | none | N/T | N/T |
| 362.78-CHO (A2162F)* | 255 | 1.7 nM | none | none | none | none |

TABLE 9-continued

Cross-reaction of hIL-21 antagonists to cynomolgus monkey, murine and rat IL-21 in the STAT-Luciferase assay.

| | Cyno IL-21 $IC_{50}$ ([cIL-21] = 100 pM) | | Murine IL-21 IC50 ([mIL-21] = 6.41 nM) | | Rat IL-21 $IC_{50}$ ([rIL-21] = 1.08 nM) | |
|---|---|---|---|---|---|---|
| | ng/mL | Molar conc. | ng/mL | Molar conc. | ng/mL | Molar conc. |
| 366.328.10 | 15 | 100 pM | none | none | N/T | N/T |
| 366.552.11 | 23 | 156 pM | none | none | none | none |
| 366.617.7 | 65 | 431 pM | none | none | N/T | N/T |

*Note: Clone 362.78-CHO (Example 1b) was tested using an 800 pM concentration of cIL-21 instead of 100 pM as was used in other experiments.
N/T = not tested.

Example 10

Evaluation of Potential Cross-Reaction to IL-4 in a Cell-Based Assay

When developing a therapeutic cytokine antagonist, it is important to know if it will cross-react with and neutralize structurally related cytokines. This primary B cell proliferation assay was designed to test the IL-21 neutralizing entities described herein for cross-reaction to and neutralization of human IL-4.

Isolation of primary B cells: To obtain primary B cells, 200 mL peripheral blood was collected from healthy human volunteers (ZymoGenetics). Blood was diluted to 400 ml with room temperature PBS and 35 mL aliquots were made in 50 ml conical tubes. Fourteen mL of room temperature Ficoll/Hypaque (Pharmacia, Uppsala, Sweden) was underlaid and the tubes were spun for 20 minutes at 2000 rpm. The PBMC interface layer was aspirated and washed two times with MACS buffer (PBS, HEPES 20 mM, and 1% BSA; Invitrogen, Carlsbad, Calif.). Cells were counted and B cells were negatively selected using the B Cell Isolation Kit from Miltenyi Biotec (Auburn, Calif.) following the protocol outlined by the manufacturer. A small sample of the purified B cells were tested for purity by FACS analysis and found to be >97% pure $CD19^+$ B cells in all experiments.

Proliferation assay: B cells proliferate in response to IL-4 co-culture with immobilized anti-IgM. To determine potential cross-reaction to and neutralization of IL-4 by anti-IL-21 mAbs, previously isolated B cells were first plated at 40,000-50,000 cells/well in a 96-well U-bottom tissue culture plate (Becton Dickinson, Franklin Lakes, N.J.) that had been pre-coated with 1.0 μg/mL anti-IgM (Southern Biotech, Birmingham, Ala.). The cells were then treated with 10 ng/mL recombinant human IL-4 (R&D Systems; Minneapolis, Minn.) and a titration series of an IL-21 antagonist (test antibodies or controls). The cells were then incubated for 3 days at 37° C. and 5% $CO_2$ in a humidified tissue culture incubator. After three days, the cells were pulsed with 1 μCi/well of [$^3$H]-Thymidine (Amersham Biosciences, Piscataway, N.J.). After 16 hours, the cells were harvested onto glass-fiber filters and the amount of [$^3$H]-incorporation was quantitated using a beta counter (Topcount NXT, Packard). None of the three anti-IL-21 monoclonal antibodies tested (362.78.1, 366.328.10.6 and 366.552.11.31) showed any neutralization of IL-4-induced proliferation at up to a 250-fold molar excess.

Example 11

11A. Evaluation of Potential Cross-Reaction to IL-2 and IL-15 in a Cell-Based Assay When developing a therapeutic cytokine antagonist, it is important to determine if it will cross-react with and neutralize structurally related cytokines. The murine T cell line, CTLL-2, can be induced to proliferate in response to human IL-2 or IL-15. Therefore, this assay was chosen to test the IL-21 neutralizing entities described herein for cross-reaction to and neutralization of human IL-2 and IL-15.

CTLL-2 cells were washed three times in proliferation bioassay media (RPMI 1640, 2× Glutamax, 10% FBS, 2× NaPyr, 1× B-mercaptoethanol and 20 mM Hepes; Invitrogen, Carlsbad, Calif.), and plated at 50000 cells per well in 96-well round bottom tissue culture plates (Becton Dickinson, Franklin Falls, N.J.). To these cells, a predetermined $EC_{90}$ dose of either IL-2 (3.0 ng/mL) or IL-15 (0.5 ng/mL) in combination with a serial dilution of the IL-21 neutralizing entities was added. The ratio of cytokine to antibody ranged from a 250-fold molar excess to a 1:1 ratio. Anti-IL-2 or anti-IL-15 neutralizing antibodies (both from R&D Systems, Minneapolis, Minn.) were used as positive controls. The cells were then incubated for 24 hours at 37° C. and 5% $CO_2$ in a humidified tissue culture incubator. After 24 hours, the cells were pulsed with 1 μCi/well of [$^3$H]-Thymidine (Amersham Biosciences, Piscataway, N.J.). Sixteen hours later, the cells were harvested onto glass-fiber filters and the amount of [$^3$H]-incorporation was quantitated using a beta counter (Topcount NXT, Packard).

Results: None of the three anti-IL-21 monoclonal antibodies tested (362.78.1, 366.328.10.6 and 366.552.11.31) showed any neutralization of IL-2 or IL-15-induced proliferation.

11B. —Confirmation Using Surface Plasmon Resonance (Biacore) that IL-21 mAB 362.78-CHO does not Bind IL-21-Related Human Cytokines IL-2, IL-4, IL-7, IL-9 or IL-15

The anti-IL-21 mAb 362.78-CHO was evaluated via surface plasmon resonance for potential cross reactivity to human IL-2, human IL-4, human IL-7, human IL-9, and human IL-15.

Materials and Methods: Experiments were completed to test the cross reactivity of the anti-IL-21 monoclonal antibody 362.78-CHO for human IL-2, human IL-4, human IL-7, human IL-9, and human IL-15. Binding studies were performed on a BIACORE T100™ (GE Healthcare, Piscataway, N.J.). Methods were programmed using BIACORE T100™ Control Software, v 2.0. Goat anti-human IgG Fc-gamma specific antibody (Jackson ImmunoResearch, West Grove, Pa.) was covalently immobilized to flow cells 1 and 2 of a CM4 sensor chip using amine coupling chemistry (EDC: NHS). The purified anti-IL-21 monoclonal antibody 362.78-CHO was subsequently captured onto flow cell 2 of the sensor chip at a density of approximately 240 RU. Flow cell 1 was used as the reference surface.

IL-2, IL-4, IL-7, IL-9, and IL-15 (all purchased from R&D Systems, Minneapolis, Minn.) were injected over the captured antibody surface (flow cell 2) and the reference flow cell (flow cell 1) at concentrations of 100, 20, and 4 nM. As a positive control for this set of experiments, IL-21 (produced at ZymoGenetics) was also injected at identical concentrations. Binding studies were performed with a flow rate of 25 µL/min, an association time of 2 minutes, and a dissociation time of 3 minutes. All binding experiments were performed at 25° C. in a buffer of 10 mM HEPES, 300 mM NaCl, 5 mM $CaCl_2$, 0.05% Surfactant P20 (Biacore), 1 mg/mL bovine serum albumin, pH 8.0. Between cycles, the flow cell was washed with 20 mM hydrochloric acid to regenerate the surface. This wash step removed both the captured 362.78-CHO antibody and any bound antigen from the chip surface. Data was compiled using BIACORE T100™ Evaluation software (version 2.0). Data was processed by subtracting reference flow cell and blank injections. Baseline stability was assessed to ensure that the regeneration step provided a consistent binding surface throughout the sequence of injections.

Results: No binding of IL-2, IL-4, IL-7, IL-9, or IL-15 to the 362.78-CHO antibody was observed. In contrast, the IL-21 positive control demonstrated a dose dependent binding that was consistent with previous studies.

This lack of cross-reactivity was subsequently explained by epitope mapping studies of clone 362.78 (see Example 17). The amino acids located in and near the D-helix of IL-21 shown to be bound by clone 362.78 (EKKPPKEFLERFK-SLL; SEQ ID NO: 2 from residue 129 to 144)) are not well-conserved among the related human gamma-chain cytokines, nor within mouse IL-21, as shown below in Table 10.

human volunteers (ZymoGenetics). Blood was diluted with 200 mL of room temperature PBS and 35 mL aliquots were made in 50 mL conical tubes. Fourteen mL of room temperature Ficoll/Hypaque (Pharmacia, Uppsala, Sweden) was underlaid and the tubes were spun for 20 minutes at 2000 rpm. The PBMC interface layer was aspirated and washed two times with MACS buffer (PBS, HEPES 20 mM, and 1% BSA; Invitrogen, Carlsbad, Calif.). Cells were counted and B cells were negatively selected using the B Cell Isolation Kit from Miltenyi Biotec (Auburn, Calif.) following the protocol outlined by the manufacturer. A small sample of the purified B cells were tested for purity by FACS analysis and found to be >97% pure in all experiments.

Proliferation assay: B cells proliferate in response to co-culture with anti-CD40 and IL-21. To determine the neutralization activity of the anti-IL-21 mAbs, B cells were plated at 40000-50000 cells/well in a 96-well U-bottom tissue culture treated plate (Becton Dickinson, Franklin Lakes, N.J.). The cells were then treated with 0.1 µg/mL anti-CD40 (goat anti-human CD40 polyclonal; R&D Systems, Minneapolis, Minn.), 50 ng/mL (3.21 nM) recombinant IL-21 (ZymoGenetics, A1207F) and a titration of an IL-21 antagonist (test mAbs or controls). The plate of cells was then incubated for 3 days at 37° C. and 5% $CO_2$ in a humidified incubator. After three days, the cells were pulsed with 1 µCi/well of [$^3$H]-Thymidine (Amersham Biosciences, Piscataway, N.J.). After 16 hours, the cells were then harvested onto glass-fiber filters and the amount of [$^3$H]-incorporation was quantitated using a beta counter (Topcount NXT, Packard). $IC_{50}$ curves measuring the effective neutralization of IL-21-induced proliferation were calculated and expressed as a molar concentration. The

TABLE 10

```
IL21_HUMAN    ------TCPSCDSYEKK--PPKEFLERFKSLLQKMIHQHLSSTHGSEDS

IL21_MOUSE    ------KCPSCDSYEKR--TPKEFLERLKWLLQKMIHQHLS

IL15_HUMAN    -------CKECEELEEK--NIKEFLQSFVHIVQMFINTS

IL2_HUMAN     ------TTFMCEYADET-ATIVEFLNRWITFCQSIISTLT

IL4_HUMAN     ---GLAGLNSCPVKEANQSTLENFLERLKTIMREKYSKCSS

IL7_HUMAN     ----SLEENKSLKEQKK-LNDLCFLKRLLQEIKTCWNKILMGTKEH

IL9_HUMAN     ------CEQPCNQTTAG--NALTFLKSLLEIFQKEKMRGMRGKI
```

IL-21 human is shown as SEQ ID NO:2; IL-21 mouse is shown as SEQ ID NO:11; IL-15 human is shown as SEQ ID NO:92; IL-2 human is shown as SEQ ID NO:93; IL-4 human is shown as SEQ ID NO:94; IL-7 human is shown as SEQ ID NO:95; IL-9 human is shown as SEQ ID NO:96.

Example 12

B Cell Proliferation Assays

Primary B Cell Assays

To further test the activity of the IL-21 neutralizing entities, two primary B cell assays were developed. The B cell proliferation assay was used to demonstrate neutralization of IL-21 induced proliferation over 4 days and the B cell differentiation assay demonstrated the neutralization of IL-21 induced plasma cell differentiation over 8 days. These experiments demonstrated neutralization of IL-21 in long-term biologically relevant assays.

Isolation of primary human B cells: To obtain primary B cells, 200 mL peripheral blood was collected from healthy $IC_{50}$ values for the top neutralizing mAbs described herein ranged from 0.71 nM to 6.55 nM and are summarized in Table 11:

TABLE 11

| Neutralization of IL-21 in B Cell Proliferation Assay | |
|---|---|
| IL-21 Antagonist | IC50 (nM) |
| soluble hIL-21R/γc-Fc | 3.5 |
| 362.75.1 | No Neutralization |
| 362.78.1 | 1.17 |
| 366.328.10 | 0.71 |
| 366.552.11 | 4.75 |
| 366.617.7 | 6.55 |

B Cell Differentiation Assay: The differentiation of naïve B cells into antibody-producing plasma cells is greatly facilitated in vitro when IL-21 is combined with anti-CD40 and IL-4 (Ettinger et al., *J Immunol*. 175:7867-79, 2005; Ettinger et al, *J Immunol*. 178:2872-82, 2007; Kuchen et al. *J Immunol*. 179:5886-96, 2007). To demonstrate activity in a longer term assay than the two Baf3-based screening assays described in Examples 7 and 8, the neutralizing entities described herein were used to neutralize IL-21 and inhibit human plasma cell differentiation. To accomplish this, primary human B cells were plated at 150,000 cells/well in a 96-well flat bottom tissue culture treated plate (Becton Dickinson, Franklin Lakes, N.J.). The cells were then treated with 0.1 μg/mL anti-CD40 (goat anti-human CD40 polyclonal; R&D Systems, Minneapolis, Minn.), 10 ng/mL recombinant human IL-4 (R&D Systems) and 25 ng/mL (1.6 nM) recombinant human IL-21 (ZymoGenetics). IL-21 antagonists (test mAbs or controls) were then added and the cells incubated at 37° C. and 5% $CO_2$ for eight days in a humidified incubator. At the end of eight days, conditioned medias were collected (for antibody titers) and cells pelleted for subsequent flow cytometry analysis.

B cell analysis using flow cytometry: Cells were resuspended in human FACS buffer (HBSS, 20 mM HEPES, 1% BSA (all from Invitrogen) and 2% Human Ab Serum (Gemini Bio-Products, Woodland, Calif.)) for five minutes to block Fc receptors. Cells were then centrifuged (5 minutes at 1200 rpm) and aspirated. Stains were prepared by diluting antibodies 1:100 in human FACS buffer and dispensing 100 μL per sample. Single stains (to adjust cytomer compensation settings) and a multi-stain mixture were prepared using the following antibodies: anti-CD138-FITC, anti-IgD-PE, anti-CD38-PE-Cy5.5 and anti-CD19-APC. Plasma cells were defined as large (assessed by forward light scatter) $CD19^+$, $IgD^{lo}$, $CD38^+$ and $CD138^+$ cells. The percentage of plasma cells relative to total B cells was used to determine effectiveness of the neutralizing entities described herein.

Results: When IL-21 was combined with IL-4 and anti-CD40, approximately 50% of the live, large B cells on day 8 were $IgD^{low}$, $CD138^+$ plasma cells. Without IL-21, the proportion of plasma cells was ~8% of the large B cells. The addition of the various IL-21 antagonists to the IL-21-containing cultures decreased the proportion of plasma cells in a dose-dependent manner. Clone 362.78.1 was the most effective neutralizer, and almost completely neutralized IL-21 activity at the 10:1 and 2.5:1 antagonist:ligand ratios. The other antibodies tested, clones 366.328.10.63 and 366.552.11.31 were nearly as effective at neutralizing the IL-21 driven differentiation. This data is summarized in Table 12.

TABLE 12

Inhibition of human plasma cell differentiation by neutralizing anti-hIL-21 mAbs

| IL-21 Antagonist | Antagonist:Ligand Ratio | | | |
|---|---|---|---|---|
| | 10:1 | 2.5:1 | 0.6:1 | 0.16:1 |
| | % IgD-low, CD138+ Plasma Cells | | | |
| 362.78.1 | 13.7 | 15.5 | 34.1 | 42.8 |
| 366.328.10.63 | 15.4 | 20.2 | 41.4 | 52.1 |
| 366.552.11.31* | 15.4 | 26.4 | 44.8 | 50.3 |
| IL-21 Receptor | 23.4 | 41.7 | 54.2 | 66.7 |

*Note that actual antagonist:ligand ratios for clone 366.552.11.31 were 14.4, 3.6, 0.9, and 0.22:1

Example 13

DTH Mouse Model

DTH responses are classic immune responses that are initiated by CD4+ T cells and mediated by T cells, neutrophils and macrophages. A DTH response is a good indicator of a CD4+ T cell mediated response. Mice are immunized subcutaneously with chicken ovalbumin protein (OVA) in either of 2 adjuvants, Complete Freunds Adjuvant (CFA; Sigma) or Ribi (Sigma; aka MPL+TDM+CWS adjuvant). This phase is called the sensitization phase (days 0-6). Ear measurements are taken seven days later. Mice are then injected in the ear with control PBS (left ear) or OVA (right ear). This phase is called the challenge phase (days 7-8) Immune responses generated to OVA induce inflammation in the ear resulting an increase in ear thickness in 24 hours in the OVA-treated, but not in the PBS-treated ear. This is measured using calipers.

C57BL/6 mice (n=8/group) are immunized in the back with 100 μg chicken ovalbumin (OVA) emulsified in CFA in a total volume of 200 μl. If Ribi is used instead of CFA, 0.5 mg/ml of ovalbumin is added to a single vial of RIBI and vortexed vigorously for 2 minutes to form an emulsion that is used to inject mice. Seven days after the immunization, mice are injected with 10 μl PBS in the left ear (control) and with 10 μg OVA in PBS in the right ear in a volume of 10 μl. Ear thickness of all mice is measured before injecting mice in the ear (0 measurement). Ear thickness is measured 24 hours after challenge. The difference in ear thickness between the 0 measurement and the 24 hour measurement is calculated and is reflective of the inflammation in the ear. Groups of mice are injected with PBS or different concentration of anti-IL-21 antibody intra-peritoneally from either days 0-6 (sensitization phase) or from days 7-8 (challenge phase). The injection on day 7 and 8 is given 2 hours before measuring ear thickness at the 0 and 24 hour time points. At the end of the 24 hour period, once ear thickness was measured, the ears were cut and placed in formalin for histological analysis.

Example 14

Mouse Model for Multiple Sclerosis

To test if anti-IL-21 has any effects on multiple sclerosis, the ability of anti-IL-21 antibodies to inhibit experimental autoimmune encephalomyelitis (EAE-MS), a mouse model for MS is tested. The well characterized T cell-dependent myelin oligodendrocyte glycoprotein (MOG) 35-55 peptide immunization model in C57BL/6 mice is used. The experiment is run to determine that anti-IL-21 antibody could delay and/or inhibit disease scores in EAE either by inhibiting DC mediated antigen presentation or by enhancing CD8 T cell responses. Absence of efficient CD8 T cell responses in this model exacerbates EAE (Malipiero et. al., *Eur. J. Immunol.*, 27:3151-3160, 1997). Delayed onset of disease in the EAE model in a dose dependent manner suggests that use of anti-IL-21 antibody may be beneficial in MS.

EAE is a mouse model for MS. In one such model, C57BL/6 mice are immunized with 100 μg MOG peptide (MOG35-55) or 100 μg recombinant MOG protein emulsified in CFA adjuvant. Two milliliters of a 0.5 mg/ml preparation of the MOG35-55 in PBS is added to a vial of CFA and vortexed vigorously to emulsify the solution or a 1:1 ratio of recombinant MOG in CFA is prepared. The backs of mice are shaved and 100 μg MOG/CFA is injected s.c in the backs of mice. Weights of mice are taken 2 days before and every day after the immunization. Mice are then injected on day 2 i.v. with 200 μl pertussis toxin (PT), a final concentration of 200 ng/mouse. Mice are monitored daily for clinical scores. Groups of mice are injected i.p. with 200 μl PBS, 100 μg BSA, 10 μg –200 μg anti-IL-21 antibody in a 200 μl volume from days 0-20, or 3× a week for 3 weeks. The weights of mice, clinical scores and incidence are evaluated and plotted for analysis.

Example 15

Anti-mIL-21 Antibody Decreases Disease Incidence and Progression in a Mouse Model of T-Cell Adoptive Transfer Colitis and Psoriasis Adoptive transfer of naive T cells into minor histocompatibility mismatched or syngeneic immunocompromised mice leads to development of colitis (Leach M W et al 1996, Powrie F et al, 1997) as well as skin lesions resembling psoriasis (Schon M P et al., Nat Med. 2:183-8, 1997; Davenport C M et al., Int Immunopharmacol. 5:653-72, 2002). Transplantation of as few as 0.2 million CD4+CD25− T cells from BALB/C or B10.D2 mice into immunocompromised C.B-17 SCID mice results in weight loss, hemoccult positive stool and development of skin lesions. The symptoms in these mice vary from colony to colony.

This model of colitis/psoriasis has some similarities to human Crohn's disease and psoriasis, and has been used extensively to test efficacy of therapeutics for these diseases in humans. For this experiment, mice (8 B10.D2 female mice donors; 50 C.B-17 SCID female recipients) were obtained from Jackson Laboratories or Charles River Laboratories, respectively. Spleens from 8 B10.D2 mice were collected. CD4+ CD25− T-cell were isolated from pooled spleens using standard methodology known in the art. Purity of the T-cell population was evaluated by flow cytometry.

Naïve C.B-17 SCID mice received $5 \times 10^5$ CD4+ CD25− T-cells (isolated from spleens of B10.D2 mice) via intravenous injection on day 0. All mice were weighed at least five times per week and carefully observed for weight loss, which can be associated with colitis. In addition, a clinical colitis score [stool consistency and blood in stool] was taken at least one day per week. Mice were also carefully monitored at least five days per week and assigned a score for signs of psoriatic symptoms (hair loss, scratching, alopecia, etc).

A rat anti-mouse IL-21 (mIL-21) antibody, a rat isotype control antibody, or vehicle (PBS) was administered to groups of mice beginning on day 0. The treatments were delivered as intraperitoneal injections, twice a week, with the antibodies being administered at 0.2 or 0.8 mg per mouse per dose. They could also be delivered using a similar dosing regimen or other route of administration. There were 9-10 mice per group in the anti-IL21 antibody groups, 6-7 mice per group in the isotype control antibody groups, and 10 mice per group in the PBS group. This dosing regimen is referred to as "prophylactic dosing".

In a separate experiment, groups of mice dosed with the same antibodies and doses described above (10 mice per group) started their treatments on day 12 following cell transfer, which is approximately the day that the mice began showing signs of psoriasis and/or colitis. This dosing regimen is referred to as "therapeutic dosing".

At the end of the study (day 45), colonic tissue was submitted for histological evidence of colitis and serum for analysis of cytokine and chemokine levels.

Results of Prophylactic Dosing: Mice receiving the anti-mIL-21 antibody at both the 0.2 and 0.8 mg doses were characterized by significant (at least $p<0.05$ or better) reductions in body weight loss and significant reductions in psoriatic skin and colitis symptom throughout the experimental period compared to mice administered PBS or 0.2 mg isotype control monoclonal antibody. At the end of the study (day 45), mice treated with either dose of the mIL-21 antibody were at approximately 100% of their starting body weight, whereas PBS-treated mice had lost an average of 16% of their starting body weight and mice treated with an isotype control antibody had lost 10-15% of their starting body weight. At day 45, mice treated with either dose of the mIL-21 antibody had approximately 6.5-7-fold lower average colitis clinical scores and approximately 5-7 fold lower average psoriatic skin scores. Only 20% of mice treated with 0.2 mg anti-mIL-21 antibody developed psoriasis, which was mild, whereas none of the mice treated with the 0.8 mg dose developed any psoriatic skin symptoms. On the other hand, 100% of the PBS-treated mice developed psoriasis, with approximately 50% of these mice developing severe symptoms. At the end of the study, there was also a significant reduction in histologic indices of colitis (scored for intestinal inflammation, lesions, and architecture) in the anti-mIL-21 antibody treated mice compared to PBS- and 0.2 mg isotype-control treated mice.

Mice treated with anti-mIL-21 antibody had significantly lower serum IL-6, RANTES, TNF-α, and MIP-1β levels compared to PBS-treated mice, further supporting an anti-inflammatory role for anti-mIL-21 antibody.

Results of Therapeutic Dosing: Mice receiving the anti-mIL-21 antibody at both the 0.2 and 0.8 mg doses, beginning from day 12 following T cell transfers, were characterized by reductions in body weight loss and significant reductions in colitis symptoms throughout the experimental period compared to mice administered the isotype control monoclonal antibody. At day 45, mice treated with either dose of the anti-mIL-21 antibody had approximately 3.5-4-fold lower average colitis clinical scores compared to isotype control antibody-treated mice. Mice treated with the 0.8 mg dose of anti-mIL-21 antibody had lower psoriasis scores than isotype control antibody- or PBS-treated mice.

Summary: Taken together, these results indicate that in vivo administration of an anti-mIL-21 antibody was efficacious in reducing colitis and psoriasis onset and severity in a murine T cell transfer model, and suggest that anti-IL-21 antibodies may be efficacious in treating human inflammatory bowel disease and/or psoriasis.

Example 16

Contact Hypersensitivity Mouse Model

Contact hypersensitivity can be induced in mice using a variety of contact allergens including dinitrofluorobenzene (DNFB) and oxazolone. Mice are sensitized topically with the allergen in a vehicle of acetone and olive oil and then challenged in the ear with the allergen in olive oil alone. Change in ear thickness is a measure of the immune response against the allergen. Anti-IL-21 antibodies are administered either at the sensitization phase (days 0-5) or during the challenge phase (days 5-6) Inhibition of ear thickness by antagonizing IL-21 indicates a role for IL-21 in inducing contact hypersensitivity.

C57B1/6 mice are painted on the back with 0.5% DNFB in acetone:olive oil (4:1) or acetone:olive oil alone on day 0. On day 5, ear thickness of mice is measured using calipers and mice are challenged in the ears with olive oil alone (control) or 0.25% DNFB in olive oil by dropping a 25 µl solution onto the ear. Change in ear thickness is measured on day 6 and the inflammation calculated as a difference in ear thickness between day 5 and day 6. Groups of mice are injected i.p. with PBS or 10-100 µg anti-IL-21 antibodies on either days 0-5 or days 5-6.

Inhibition of ear thickness by anti-IL-21 antibodies demonstrates that anti-IL-21 antibodies can be useful in inhibiting contact hypersensitivity.

Example 17

Epitope Mapping

A. Hydrogen-Deuterium Exchange (HDx) Experiment

In an effort to identify the epitope regions of IL-21 recognized by neutralizing anti-IL-21 mAbs 362.78.1.44, 362.597.3, 366.328.10, 366.552.11 and the soluble hIL-21R/γc-Fc an immunoaffinity-based hydrogen deuterium exchange (HDx) method was applied followed by mass spectrometry analysis. Specifically, the purified mAbs were immobilized on CNBr-activated sepharose beads and exchanged into deuterium buffer. Deuterated IL-21 was bound to the immunoaffinity beads by incubation and the beads were washed with deuterated buffer to remove unbound proteins. The antigen-antibody complex was then subjected to PBS solution to initiate back-exchange to amide hydrogen on the unbound regions of IL-21. Deuterium hydrogen exchange was then quenched and IL-21 was eluted in low pH buffer, which was then subjected to proteolytic digestion by immobilized pepsin. Peptide mass maps were then generated by MALDI-TOF mass spectrometry and compared with that of the control sample, generated from the free state of IL-21, which was exchanged back to amide hydrogen from the deuterated IL-21 by dilution with PBS solution. FIG. 3 shows expanded mass spectra of pepsin-digested peptides of both the free-state of IL-21 (FIGS. 3A and 3C) and the antibody-bound IL-21 (FIGS. 3B and 3D). As indicated in FIG. 3A, overlapping peptide isotope were assigned to corresponding peptides EKKPPKEF (SEQ ID NO: 2 from residue 129 to 136) (m/z, 1002.5619 Da) and LERFKSLL (SEQ ID NO: 2 from residue 137 to 144) (m/z, 1005.6091 Da) of the free-state of IL-21 with theoretical peptide masses within 10 ppm mass accuracy. A small amount of residual deuterated peptide was observed around m/z, 1002.5619 Da, due to incomplete amide hydrogen exchange.

FIG. 3B is a spectrum of the same mass range of FIG. 3A showing the two overlapping peptide isotope envelopes having monoisotope ions at 1014.49 m/z and 1015.00 m/z. Because two peptide ions were clustered around the same mass range, it was difficult to assign each peptide identity between the two ions. However, tandem mass spectrometry data of the peptide ions of FIGS. 3A and B showed that they had identical peptide fragmentation patterns (data not shown). Although there was a small percentage of non-deuterated peptide detected from the sample obtained from the antigen-antibody complex, the majority of the peptide ions retained deuterium and shifted to the higher mass region by virtue of limited solvent accessibility to the antibody/antigen binding regions, indicating that the mAb binding site likely contains the region EKKPPKEFLERFKSLL (SEQ ID NO: 2 from residue 129 to 144).

Another pepsin-digested peptide from both the free-state of IL-21 and the antigen-antibody complex was observed as shown in FIGS. 3C and D and it was identified as KSLLQK-MIHQHLSSRTHGSEDS (SEQ ID NO: 2 from residue 141 to 162) (m/z, 2519.2451) based on the theoretical mass of pepsin-digested peptide fragment of IL-21. As shown in FIG. 3D, comparing the mass shift of this 22-amino acid residue peptide (Δmass=9.0 Da) with the mass shift of those two upstream residues (FIG. 2B, EKKPPKEF (SEQ ID NO: 2 from residue 129 to 136) and LERFKSLL (SEQ ID NO: 2 from residue 137-144), this region was only marginally protected upon binding of the mAb, indicating that only a portion of this peptide may be involved in binding to the mAb. In fact this peptide sequence is the C-terminal tail and it contains four overlapping amino acid residues with the peptide (LERFKSLL (SEQ ID NO: 2 from residue 137 to 144), which appeared to be significantly protected by the mAb. Based on these mass spectrometric measurements of deuterium retention, we estimated that the IL-21 epitope for binding of the mAb EKKPPKEFLERFKSLL (SEQ ID NO: 2 from residue 129 to 144) and the upstream sequence of KSLLQKMI-HQHLSSRTHGSEDS (SEQ ID NO: 2 from residue 141 to 162).

B. Lysine Labeling Protection Experiment

Using the HDx assay, the IL-21 mAb binding epitope region was estimated and it was observed that five lysine residues (from a total of 12 lysine residues in IL-21) reside in the estimated binding epitope region. Since lysine residues are most likely to be present at solvent accessible regions of proteins due to their charged characteristic, lysine appears to be an ideal choice for selective chemical modification for a parallel determination of the antigen epitope region. The concept behind the chemical modification strategy is that the protection of lysine modification in an antigen in the presence and absence of antibody correlates to its binding epitope (Scholten et al., *J. Amer. Soc. Mass Spectr.* 17: 983-994, 2006). Therefore, for further characterization of the epitope region and for the determination of those lysine residues involved in the binding of the mAb, selective acetylation on lysine residues was performed in both the affinity-bound and free states of IL-21. The site of lysine modification/protection was determined by whole mass and peptide mapping analyses using MALDI-TOF and electrospray ionization (ESI) mass spectrometry.

Scholten et al., (Scholten et al., *J. Amer. Soc. Mass Spectr.* 17: 983-994, 2006) investigated the molar ratio between the acetylation reagent (NHS-acetate) and an antigen for the full acetylation of solvent accessible lysine residues and found that the labeling was effective at 250-fold molar excess of the reagent in 3 min reaction. To determine the binding epitope, the same labeling reaction condition was employed for both the free state IL-21 and the affinity bound IL-21 with several neutralizing IL-21 mAbs, as well as the IL-21 heterodimeric receptor protein (IL-21R/γc-Fc). With the given labeling reaction condition, different solvent accessibility of lysine residues of the IL-21 alone and the affinity-bound IL-21 gave rise to the distribution of lysine acetylation (acetyl occupancy) on the IL-21 molecule. The number of protected lysine residues on the affinity-bound IL-21 was compared to the IL-21 alone by the most intense ion. Spectral alignment based on the most intense ions clearly showed that the number of lysine acetylations on the antigens isolated from different immune complexes is varied. It was evident that the lysine labeling reagent was less accessible into the affinity-bound IL-21. Hence, the acetylation was reduced by the binding of the antigen to the antibody.

Figure 4:
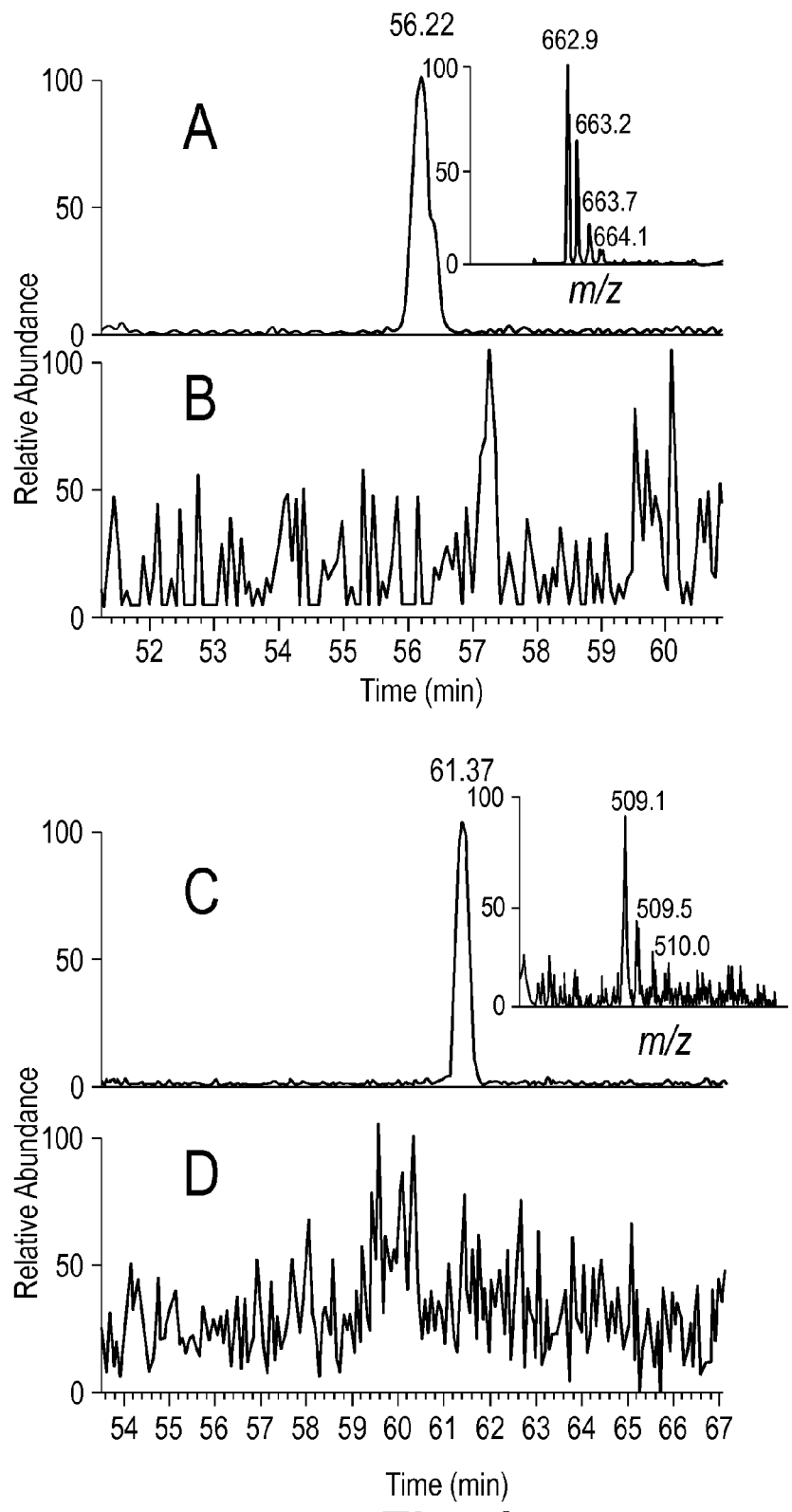
FIG. 4 illustrates selected ion chromatograms of acetylated and non-acetylated peptides. Selected single ion chromatogram of acetylated TCPSCDSYEKKPPKEF (SEQ ID NO: 2 from residue 119 to 136) (m/z, 1986 Da) isolated from IL-21 alone (A) and the same chromatographic trace of the IL-21 immune complex (B). The embedded mass spectrum is triply charged state of the peptide mass (m/z, 662.9). The third trace shows the selected ion chromatogram of the peptide ion at m/z 1018 Da, which is acetylated KSLLQKMI (SEQ ID NO: 2 from residue 141 to 148) isolated from IL-21 alone (C) and the same chromatographic trace of the IL-21 immune complex (D). The embedded mass spectrum is doubly charged state of the peptide mass (m/z, 509.1)

The acetylation protected lysines, which may be involved in the binding of the mAb, were further probed by protease digestion, and followed by peptide mass mapping analysis using liquid chromatography mass spectrometry. Since covalently modified lysine residues are resistant to tryptic digestion, pepsin proteolytic enzyme was used to generate more mass spectrometry-detectable peptides to study the lysine modification in more detail. The modification of individual peptides using single peptide ion chromatography was investigated. As shown in FIG. 4, selected ion chromatograms were generated from both the control (IL-21 alone) and the test samples (affinity bound IL-21 molecules) to determine acetylated and non-acetylated lysine residues. FIG. 4A is a selected ion chromatogram of a proteolytic peptide eluting at 56.22 min in the given chromatographic condition and the monoisotope peptide ion mass was at 662.9 Da, which appeared to be in a triply charged state ($\Delta m=0.3$ Da) as indicated in the embedded mass spectrum. Identification of this peptide in a triply charged state as the lysine acetylated pepsin-digested peptide fragment, TCPSCDSYEKKPPKEF (SEQ ID NO: 2 from residue 119 to 136) (m/z, 1986 Da) was made, whereas the non-acetylated peptide mass is 1860 Da (m/z). The mass difference (acetylated peptide/non-acetylated peptide) was 126 Da, indicating that all three lysine residues in this peptide were acetylated in the free-state of IL-21. However, a selected ion chromatogram of the affinity bound IL-21 showed no trace of the peptide (FIG. 4B) indicating that the three lysine residues were completely protected by the IL-21 antibody binding.

An additional pepsin-digested peptide (KSLLQKMI (SEQ ID NO: 2 from residue 141 to 148) was found to be protected upon binding of IL-21 mAb (FIGS. 4C and 4D). Its monoisotopic ion was at 509 Da (m/z) as a doubly charged ion ($\Delta m=0.5$ Da) and the mass difference (acetylated peptide/non-acetylated peptide) was 42 Da, indicating that only one of the two lysine residues in this peptide was protected. Earlier H/D exchange experiments indicated that the lysine upstream of the C-terminal tail of the peptide sequence, KSLLQKMIHQHLSSRTHGSEDS (SEQ ID NO: 2 from residue 141 to 162), was most likely protected by the antibody binding. Thus it is most likely that K113 instead of K119 is involved in the antibody binding.

Four lysine residues (K102, K103, K106 and K113) were protected from acetylation by clones 362.78.1.44 and 362.597.3 binding and they were located within the estimated IL-21 mAb binding epitope region as determined from the HDx assay. Collectively, the acetylation protection assay provided the involvement of specific lysine residues in the antigen-antibody interaction and further confirmed the epitope sequence estimated from the HDx assay.

17C.—Comparison of IL-21 Amino Acid Sequences from Various Species

To better understand the species cross-reactivity results in Examples 3 and 9, in light of the defined epitopes on IL-21 bound by the IL-21 mAbs (Example 17A and B), amino acid sequences were obtained and compared for IL-21 across multiple species (Table 13). The overall human sequence was more than 96% identical to cynomolgus and rhesus monkey sequences, while only 61-65% identical to the rodent IL-21 sequences. Notably, the discontinuous epitope bound by clones 362.78.1.44 and 362.597.3 as described in Example 17 (underlined in Table 13) is identical in human, cynomolgus and rhesus monkey IL-21, while the rat IL-21 sequence differs from human IL-21 in 6 residues in these regions, and the mouse IL-21 sequence differs by 7 residues.

TABLE 13

IL-21 amino acid sequence alignment for human, cynomolgus monkey, rhesus monkey, rat and mouse IL-21.

| | |
|---|---|
| Hu IL-21 | MRSSPGNMERIVICLMVIFLGTLVHKSSS QGQDRHMIRMRQLID<u>IVDQLKNYVNDLV</u> |
| CynoIL-21 | MRSSPGNMERIVICLMVIFLGTLVHKSSS QGQDRHMIRMRQLIDIVDQLKNYVNDLD |
| RhesusIL-21 | MRSSPGNMERIVICLMVIFLGTLVHKSSS QGQDRHMIRMRQLIDIVDQLKNYVNDLD |
| Rat IL-21 | MERTLVCLILIFLGTVAHKSSP QRPDHLLIRLRHLMDIVEQLKIYENDLD |
| MuIL-21 | MERTLVCLVVIFLGTVAHKSSP QGPDRLLIRLRHLIDIVEQLKIYENDLD |
| Hu | PEFLPAPEDVETNCEWSAFSCFQKAQLKSANTGNNERIINVSIKKLKRKPP |
| Cyno | PEFLPAPEDVETNCEWSAISCFQKAQLKSANTGNNERIINLSIKKLKRKSP |
| Rh | PEFLPAPEDVETNCEWSAISCFQKAQLKSANTGNNERIINLSIKKLKRKSP |
| Rat | PELLTAPQDVKGQCEHEAFACFQKAKLKPSNTGNNKTFINDLLAQLRRRLP |
| Mu | PELLSAPQDVKGHCEHAAFACFQKAKLKPSNPGNNKTFIIDLVAQLRRRLP |
| Hu | STNAGRRQKHRLTCPSCDS<u>YEKKPPKEFLERFKSLLQKMI</u>HQHLSSRTHGSEDS |
| Cyno | STGAERRQKHRLTCPSCDSYEKKPPKEFLERFKSLLQKMIHQHLSSRTHGSEDS |
| Rh | STGAERRQKHRLTCPSCDSYEKKPPKEFLERFKSLLQKMIHQHLSSRTHGSEDS |
| Rat | AKRTGNKQRHMAKCPSCDLYEKKTPKEFLERLKWLLQKMIHQHLS |
| Mu | ARRGGKKQKHIAKCPSCDSYEKRTPKEFLERLKWLLQKMIHQHLS |

IL-21 human is shown as SEQ ID NO:2; IL-21; mouse is shown as SEQ ID NO:11; IL-21 cynomylous is shown as SEQ ID NO:9; IL-21 rhesus is shown as SEQ ID NO:9; IL-21 rat is shown as SEQ ID NO:97.

The discontinuous epitope determined for two highly related anti-hIL-21 mAbs 362.78.1 and 362.597.3 is underlined above.

Example 18

Anti-Idiotype Monoclonal Antibodies to 362.78-CHO for Use in Pre-Clinical and Clinical Immunoassays Anti-idiotype mAbs were generated specific for 362.78-CHO for application in pre-clinical and clinical immunoassays, such that potential anti-362.78-CHO antibody responses in individuals treated with this therapeutic anti-IL-21 mAb can be specifically measured.

To distinguish between the immunogen (362.78-CHO), which is itself an antibody, and the anti-idiotype antibodies in this Example, the immunogen will be designated as Ab1 and an anti-idiotype antibody will be designated as Ab2. An anti-idiotypic antibody should inhibit (neutralize) binding of the Ab1 to its antigen (IL-21). However, it should be noted that in the process, anti-Ab1 antibodies will be generated that are not anti-idiotypic. By definition, these will be anti-362.78-CHO binding, non-neutralizing antibodies and may also be of use in the pre-clinical and clinical immunoassays.

Methods: To immunize mice with 362.78-CHO, five 6 to 8 week old BALB/c mice (Charles River Laboratories, Wilmington, Mass.) were immunized with 362.78-CHO. The mice were initially immunized by subcutaneous injection with ~50 µg of purified, 362.78-CHO (Lot#A2125F) in combination with Emulsigen®-P adjuvant (MVP Laboratories INC, Omaha, Nebr.) as per the manufacturer's instructions. Following the initial immunization, each of the mice received an additional 50 µg of 362.78-CHO in Emulsigen®-P adjuvant via the subcutaneous route every two weeks over a six week period. Seven days after the third and fourth immunizations the mice were bled via the retro orbital plexus and the serum was separated from the blood for analysis of its ability to bind to 362.78-CHO.

Selection of Fusion Animal Using Both a Capture Assay and a Neutralization Assay:

Capture Assay: The ability of mouse anti-362.78-CHO (Ab2, anti-idiotype) antibodies in the antisera to bind to 362.78-CHO (Ab 1, produced in CHO cells, lot #E10569) was assessed using a capture style ELISA assay. In this assay, wells of 96-well polystyrene ELISA plates were first coated with 100 µL/well of goat anti-human IgG, Fc specific antibody (Jackson ImmunoResearch Laboratories, West Grove, Pa.) at a concentration of 1 µg/mL in Coating Buffer (0.1M $Na_2CO_3$, pH 9.6). Plates were incubated overnight at 4° C. after which unbound antibody was aspirated and the plates washed twice with 300 µL/well of Wash Buffer (PBS-Tween defined as 0.137M NaCl, 0.0022M KCl, 0.0067M $Na_2HPO_4$, 0.0020M $KH_2PO_4$, 0.05% v/w polysorbate 20, pH 7.2). Wells were blocked with 200 µL/well of Blocking Buffer (PBS-Tween plus 1% w/v bovine serum albumin (BSA) for 60 minutes at room temperature (RT), aspirated and the plates washed twice with 300 µL/well of PBS-Tween. Wells were incubated with 362.78-CHO (Ab1, ZGI produced in CHO cells, lot #E10569) at a concentration of 1 µg/ml (in 1% BSA in PBS-Tween). After 1 hour incubation at RT, wells were aspirated and the plates washed twice as described above. Serial 10-fold dilutions (in 1% BSA in PBS-Tween) of the antisera (Ab2) were prepared beginning with an initial dilution of 1:1000 and ranging to 1:1,000,000. Duplicate samples of each dilution were then transferred to the assay plate, 100 µL/well. Normal mouse sera served as a negative control. Following a 1 hour incubation at RT, the wells were aspirated and the plates washed twice as described above. Goat anti-mouse IgG, Fc specific, HRP conjugated antibody (Jackson ImmunoResearch Laboratories) at a dilution of 1:5000 was then added to the wells, 100 µL/well. Following a 1 hour incubation at RT, unbound detection antibody was aspirated from the wells and the plates washed twice. After the aspiration, 100 µL/well of tetramethyl benzidine (TMB) (BioFX Laboratories, Owings Mills, Md.) was added to each well and the plates incubated for 1 minutes at RT. Color development was stopped by the addition of 100 µL/well of Stop Reagent (BioFX Laboratories, Owings Mills, Md.) and the absorbance values of the wells read on a Molecular Devices Spectra MAX 340 instrument at 450 nm.

Neutralization Assay: The ability of mouse anti-362.78-CHO anti-idiotype antibodies (Ab2) in the antisera to inhibit (neutralize) the binding activity of 362.78-CHO (Ab1) was assessed using a plate based neutralization assay. In this assay, wells of 96-well polystyrene ELISA plates were first coated with 100 µL/well of human IL-21 ligand (lot #A1207F) at a concentration of 1 µg/mL in Coating Buffer (0.1M $Na_2CO_3$, pH 9.6). Plates were incubated overnight at 4° C., after which unbound ligand was aspirated and the plates washed twice with 300 µL/well of Wash Buffer (PBS-Tween defined as 0.137M NaCl, 0.0022M KCl, 0.0067M $Na_2HPO_4$, 0.0020M $KH_2PO_4$, 0.05% v/w polysorbate 20, pH 7.2). Wells were blocked with 200 µL/well of Blocking Buffer (PBS-Tween plus 1% w/v bovine serum albumin (BSA)) for 1 hour, after which the plates were washed twice with Wash Buffer. Serial 10-fold dilutions (in 1% BSA in PBS-Tween) of the antisera (Ab2) were prepared beginning with an initial dilution of 1:100 and ranging to 1:100,000. Normal mouse sera served as a negative control. Duplicate samples of each dilution were then transferred to a 96-well dilution plate, 100 µL/well. Ab1 was added as a 2× solution, 100 µL/well. Following a 45 minute incubation at RT, 100 µL/well was transferred to the assay plate after the Blocking Buffer was aspirated. Following a 1 hour incubation at RT, the wells were aspirated and the plates washed twice as described above. Horseradish peroxidase-labeled Goat anti Human IgG, Fc specific, HRP conjugated (Jackson ImmunoResearch Laboratories, West Grove, Pa.) at a dilution of 1:5000 was then added to each well, 100 µL/well, and the plates incubated at RT for 1 hour. After removal of unbound detection antibody, the plates were washed twice, 100 µL/well of tetra methyl benzidine (TMB) (BioFX Laboratories, Owings Mills, Md.) added to each well and the plates incubated for 2 minutes at RT. Color development was stopped by the addition of 100 µL/well of Stop Reagent (BioFX Laboratories, Owings Mills, Md.) and the absorbance values of the wells read on a Molecular Devices Spectra MAX 340 instrument at 450 nm.

Fusion: Two mice with the highest anti-362.78-CHO neutralization titers were immunized a final time with approximately 50 µg of 362.78-CHO (Ab1) in PBS without adjuvant via subcutaneous injection. Four days later, the spleen and lymph nodes of these mice were harvested. Electrofusion was performed using standard methods known in the art to fuse lymphocytes with mouse myeloma P3-X63-Ag8.653 cells (American Type Culture Collection, CRL 1580) at a 1:1 lymphocyte-myeloma ratio, using the Cyto-pulse CEEF-50 apparatus (Cyto Pulse Sciences Inc., Glen Burnie, Md.). The fusion mixture was distributed into 96-well flat-bottomed plates. Wells of the fusion plates were fed three times with a 70% replacement of hybridoma growth medium (IMDM with 1× L-glutamine (100×), 1× Penicillin-Streptomycin (100×), all from Gibco Invitrogen, Carlsbad, Calif., 10% Fetalclone1 serum, non-heat inactivated (HyClone, Logan, Utah), 10% Hybridoma Cloning Factor (BM Condimed H1 Roche Diagnostic, Indianapolis, Ind.), 1× HAT supplement (50×, Gibco Invitrogen). Wells were assayed ten days after plating of the fusion.

Selection of Master Wells: The 96-well fusion plates were screened for the presence of mouse anti-362.78-CHO idiotype antibodies using a capture style ELISA as described above except that hybridoma supernatants were tested undiluted from the culture plates. Hybridoma cells of positive wells were successfully expanded into culture in 24-well plates. When the density of the 24-well cultures was approximately 4-6×10$^5$ cells/mL, the supernatant (approximately 1.5 mL) was individually collected and stored for each well and the cells from each well cryopreserved. Freezing medium consisted of 90% Fetalclone 1 serum and 10% DMSO. Each of the 24-well supernatants was reanalyzed in both the capture ELISA and plate based neutralization ELISA assay described above. Results indicated that following expansion, all of the master well supernatants had retained their ability to recognize 362.78-CHO antibody (Ab1) in solution. Seven of the master well supernatants retained their ability to neutralize the binding of Ab1 to human IL-21 ligand.

Cloning: Cells from 5 master wells were chosen according to their neutralizing activity and cloned in hybridoma growth medium supplemented with 1×HT (100×, Gibco Invitrogen) in order to isolate a clonal hybridoma producing the neutralizing mAb of interest. Cells were cloned in 96-well microtiter cell culture plates using a standard low-density dilution (less than 1 cell per well) approach and monoclonality was assessed by microscopic examination of wells for a single foci of growth prior to assay. Six days post-plating, all plates were screened by the neutralization ELISA for anti-362.78-CHO anti-idiotype inhibiting antibodies. Hybridoma cells from positive wells were successfully expanded into 24-well plates.

Selection of First Round Clones: Supernatants from approximately 6 wells of each cloned hybridoma line that were positive for specific mAb and originated from wells with only a single colony of hybridoma growth were collected from each cloning set and rescreened at various dilutions in the neutralization ELISA to identify a best neutralizing mAb producing clone. When the density of a best clone of the 24-well cultures were approximately $4$-$6 \times 10^5$ cells/mL, the supernatant was individually collected and stored for each well and the cells from each well cryopreserved.

Summary: mouse monoclonal antibodies (Ab2) reactive against the recombinantly expressed 362.78-CHO antibody (Ab1) were generated and exhibit neutralizing activity capable of blocking the binding of 362.78-CHO antibody to human IL-21. These antibodies can be used as reagents in pre-clinical and clinical immunoassays.

Example 19

Binding of Native Intracellular Human and Cynomolgus Monkey IL-21 (but not Mouse or Rat IL-21) by IL-21 mAB 362.78.1.44

The neutralizing anti-IL-21 monoclonal antibodies described herein were generated from transgenic mice expressing human immunoglobulin genes and immunized with recombinant human IL-21 (see Example 1). It was important to confirm that the IL-21 mAb clone 362.78.1.44 can bind and neutralize native human IL-21 in addition to the recombinant form of the IL-21. Additionally, in order to support preclinical toxicology studies, it is helpful to understand the binding capacity of the IL-21 mAb clone 362.78.1.44 to native IL-21 in a variety of species. In order to test this, one approach is to label IL-21 mAb clone 362.78.1.44 with a fluorescent dye and use it to detect intracellular IL-21 in activated T cells by flow cytometry. In this study, freshly isolated human and cynomolgus monkey peripheral blood leukocytes as well as rat and mouse splenocytes were activated in vitro with PMA and ionomycin for 24 hours to induce IL-21 production. Cells were harvested, fixed, permeabilized and stained for expression of CD3 or CD4 (to define helper T cell populations) and IL-21 using the IL-21 mAb clone 362.78.1.44 labeled with ALEXA FLUOR-647 (AF-647), and compared to the staining intensity induced by an isotype-matched control antibody. A positive signal in this assay, above that observed for the isotype control mAb, demonstrates specific IL-21 mAb clone 362.78.1.44 binding to endogenous IL-21 in the test species, though it is not an indicator of IL-21 neutralizing activity. Further studies are required to demonstrate IL-21 neutralization in a species that tests positive for IL-21 binding with the anti-human IL-21 mAb clone 362.78.1.44 (see Example 20).

Isolation of human PBMC: 100 mL peripheral blood was collected from healthy human volunteers (ZymoGenetics) in green top heparin Vacutainer tubes (Becton Dickinson, San Jose, Calif.). Blood was diluted with 100 mL of room temperature PBS and 35 mL aliquots were distributed into 50 mL conical tubes. 14 mL of room temperature Ficoll/Paque PLUS (Pharmacia, Uppsala, Sweden) was underlaid and the tubes were spun for 20 minutes at 2000 rpm. The PBMC interface layer was removed and washed two times with assay media (RPMI 1640 with supplemental Penicillin/Streptomycin, 10% Fetal Bovine Serum, Sodium Pyruvate, 2 μM β-Mercaptoethanol, all from Invitrogen, Carlsbad, Calif.). Viable cells were counted in trypan blue using standard techniques.

Isolation of cynomolgus monkey PBMC: 40 mL peripheral blood was collected in green-top heparin Vacutainer blood collection tubes (BD Biosciences) from a cynomolgus monkey housed at the University of Washington in Seattle. Blood was diluted with 40 mL of room temperature PBS and 35 mL aliquots were distributed into 50 mL conical tubes. Fourteen mL of room temperature Ficoll/Paque PLUS (Pharmacia, Uppsala, Sweden) was underlaid and the tubes were spun for 25 minutes at 2000 rpm. The PBMC interface layer was removed and washed two times with assay media (RPMI 1640 with supplemental Penicillin/Streptomycin, 10% Fetal Bovine Serum, Sodium Pyruvate, 2 μM β-Mercaptoethanol). Viable cells were counted in trypan blue using standard techniques.

Isolation of murine and rat splenocytes: Both rat and mouse splenocytes were prepared according to the following protocol. A freshly collected spleen was gently disrupted to a single cell suspension using the ends of two frosted glass slides. Cells were then passed through a 70-μM nylon mesh filter to remove clumps. Red blood cells were lysed by resuspending the cell pellet in 2 mL ACK lysis buffer for 10 minutes at room temperature. This reaction was stopped by the addition of assay media, the cells were then centrifuged (1200 RPM for 5 minutes), resuspended and passed over another nylon mesh filter to remove debris. Viable cells were counted in trypan blue using standard techniques.

Overnight activation of cells with PMA and ionomycin: Cells from all species were resuspended at 2.0×10e6 cells per mL. One mL of cells was then plated with or without the addition of 20 ng/mL PMA and 200 ng/mL ionomycin into a 24-well plate and incubated at 37° C. for 20 hours in a humidified 5% $CO_2$ tissue culture incubator. After 20 hours, 1.0 μL of GolgiPlug (BD Pharmingen) was added to each well and the cells were incubated an additional four hours.

Cell harvest and surface stain: Following the 24 hour incubation described above, cells were harvested, washed with cold FACS buffer and plated at 2.0×105-5.0×10e5 cells per well in a 96-well tissue culture plate (Becton Dickinson and Co., Franklin Lakes, N.J.). Cells were then stained with 1 μg/mL of one or more of the following antibodies, as appropriate: anti-murine CD4-PE, anti-rat CD3-PE, anti-rat B220-PE, or anti-monkey CD4-PE, or anti-human CD4-PE for 20 minutes on ice. Cells were then washed two times in PBS in preparation for fixation.

Cell fixation and permeabilization: To fix cells, each cell pellet was resuspended in 200 μL of 2% paraformaldehyde and. incubated at room temperature for 5 minutes. Cells were then centrifuged (5 minutes at 1200 rpm) and the supernatants aspirated, and the cells were resuspended in a permeabilization buffer [PBS supplemented with 0.1% saponin (Calbiochem) and 0.5% BSA (Sigma)] for 10 minutes at room temperature.

Intracellular stain: Following fixation and permeabilization, cells were stained with ~1 μg/mL of one of the following labeled antibodies: anti-mouse IL-21-AF647, anti-human IL-21 clone 362.78.1.44-AF647 (both produced at ZymoGenetics) or a comparator anti-human IL-21-AF647 antibody from BD Pharmingen. Cells were then incubated at room temperature in the dark for 40 minutes. After 40 minutes, the cells were washed twice with FACS buffer (HBSS supplemented with 1% BSA, 2% Human AB serum and 0.05% HEPES)

Data acquisition and analysis: Upon completion of staining and washing, cells were resuspended in 400 μL FACS buffer and data were collected using a FACS Calibur (BD Pharmingen) running CellQuest software. Data were analyzed using FCS Express data analysis software (De Novo Software, Los Angeles, Calif.).

Results: Detection of human IL-21 in PMA+ionomycin stimulated human T cells: While only 0.015% of the CD3+ T 362.78.1.44 in other assays (see Example 9), does strongly suggest that this mAb probably does not bind rat IL-21.

Conclusion: The IL-21 mAb clone 362.78.1.44 described herein clearly binds to the native human and cynomolgus monkey forms of the IL-21 protein but not to murine or rat IL-21.

TABLE 14

| Species | Isotype control | Anti-human IL-21 mAb (clone 78) | Anti-IL-21 Positive control |
|---|---|---|---|
| Human | 0.015% of CD3+ T cells stained positive with an hIgG4-AF647 control | 9% of CD3+ T cells were IL-21+ | 10% of CD3+ T cells were IL-21+ (eBiosciences αIL-21 mAb*) |
| Cynomolgus Monkey | 0.1% of CD3+ T cells stained positive with an hIgG4-AF647 control | 3.6% of CD3+ T cells were IL-21+ | 0.2% of CD3+ T cells were IL-21+* |
| Mouse | No isotype control used | None detected | 13.5% of CD4+ T cells were IL-21+ |
| Rat | No isotype control used | None detected | Not available |

*(this mAb may not bind strongly to cyno IL-21)

cells stained positive using the isotype control, approximately 9% of the CD4+ T cells stained positive for IL-21 using the IL-21 mAb clone 362.78.1.44 labeled with AF-647. The same fraction of IL-21+ cells was detected using the commercially available IL-21 mAb from eBiosciences. This demonstrates that the IL-21 mAb can bind endogenously produced IL-21 in human CD4+ T cells.

Detection of cynomolgus monkey IL-21 in PMA+ionomycin stimulated peripheral blood mononuclear cells: Approximately 3.6% of the CD3+ cyno T cells stained positive for IL-21 using the IL-21 mAb clone 362.78.1.44 labeled with AF-647, compared to 0.1% positive using the isotype control. This number is higher than that detected using a commercially available anti-human IL-21 mAb from eBiosciences. This discrepancy may be due to a weaker binding affinity of the eBiosciences antibody for cynomolgus IL-21. These results demonstrate that the anti-human IL-21 mAb clone 362.78.1.44 can bind endogenously produced IL-21 in cynomolgus monkey CD3+ T cells.

Detection of murine IL-21 in PMA+ionomycin stimulated splenocytes: Using a rat anti-murine IL-21 monoclonal antibody generated at ZymoGenetics as a positive control, approximately 13.5% of the activated mouse CD4+ T cells were positive for IL-21. However, as predicted from western blots and neutralizing bioactivity assays showing that the anti-human IL-21 mAb clone 362.78.1.44 does not bind or neutralize mouse IL-21 (see Examples 3 and 9), the anti-human IL-21 mAb clone 362.78.1.44 labeled with AF647 did not detect any IL-21-positive cells. This further demonstrates that the anti-human IL-21 mAb clone 362.78.1.44 does not bind to murine IL-21.

Detection of rat IL-21 in PMA+ionomycin stimulated splenocytes: Rat splenocytes were stimulated overnight in the presence of PMA and ionomycin. These stimulation conditions were sufficient to produce IL-21 positive T cells in human, cynomolgus monkey and murine T cells. In this experiment, neither the anti-mouse IL-21 mAb nor the anti-human IL-21 mAb clone 362.78.1.44 detected any cells that were positive for IL-21. However, because there was no positive control in this experiment, this negative result does not conclusively eliminate the possibility that the anti-human IL-21 mAb clone 362.78.1.44 can bind to rat IL-21. However, these data, considered along with the lack of neutralization of rat IL-21 bioactivity by the anti-human IL-21 mAb clone Example 20

Binding and Neutralization of Native Human IL-21 Bioactivity by Clone 362.78.1.44

The neutralizing anti-IL-21 monoclonal antibodies (IL-21 mAb) described herein were generated from transgenic mice expressing human immunoglobulin genes and immunized with recombinant human IL-21 (see Example 1). It was important to confirm that the IL-21 mAb clone 362.78.1.44 can bind and neutralize native human IL-21 in addition to the recombinant form of IL-21. To demonstrate neutralization of native IL-21, the Baf3/IL-21R pSTAT cell-based assay previously described (see Example 7) was utilized and activated CD4+ T cell conditioned media samples were used as the source of native IL-21. In this experiment, T cell conditioned media samples were preincubated with varying amounts of IL-21 mAb clone 362.78.1.44 and the level of IL-21-induced STAT3 phosphorylation (pSTAT3) in the Baf3/hIL-21R transfectants was then measured. Neutralization of native IL-21 was demonstrated using activated T cell conditioned media samples from four separate healthy human donors.

Isolation of human PBMC and generation of T cell conditioned media samples: 100 mL of peripheral blood was collected from 4 healthy human volunteers (ZymoGenetics) in green top heparin Vacutainer tubes (Becton Dickinson, San Jose, Calif.). Blood was then diluted with 100 mL of room temperature PBS and 35 mL aliquots were distributed into 50 mL conical tubes. 14 mL of room temperature Ficoll/Paque PLUS (Pharmacia, Uppsala, Sweden) was underlaid and the tubes were spun for 20 minutes at 2000 rpm. The PBMC interface layer was removed and washed two times with assay media (RPMI 1640 with supplemental Penicillin/Streptomycin, 10% Fetal Bovine Serum, Sodium Pyruvate, 2 μM β-Mercaptoethanol, all from Invitrogen, Carlsbad, Calif.) Viable cells were counted in trypan blue using standard techniques. T cells were negatively selected using a Human CD4+ T Cell Selection Kit from Miltenyi Biotec (Auburn, Calif.) following the protocol outlined by the manufacturer. Using standard immunophenotyping techniques, the CD4+ T cells were subsequently determined to be >95% pure by flow cytometry. T cells were then incubated for three days at 5×10e5 cells per well in a 24-well plate pre-coated with 5.0 μg/mL anti-CD3 antibody in Th1 skewing media containing 5.0 μg/mL anti-IFNγ, 1.0 μg/mL anti-CD28 (all from Becton Dickinson) and 10 ng/mL recombinant IL-12 (R&D Systems, Minneapolis, Minn.). After three days, cells were washed, re-plated in media containing 25 ng/mL PMA and 500 ng/mL ionomycin and incubated for five hours at 37° C. After five hours, conditioned media samples were harvested and frozen and stored at −80° C. until day of experiment.

To estimate the approximate IL-21 concentration in the T cell conditioned media samples, 1:4 serial dilutions were prepared and tested for induction of STAT3 phosphorylation in the Baf3/hIL-21R transfectants. Following the 10 minute pSTAT3 bioassay protocol outlined in Example 7, the relative concentration of IL-21 in each conditioned media sample was estimated by comparing the level of pSTAT3 to that generated using a titration of recombinant IL-21. Using these data, the concentration of IL-21 in each of the four conditioned media samples was determined to be between 5.0 and 10.0 ng/mL.

To demonstrate neutralization of native IL-21-induced STAT3 phosphorylation, 1:10 dilutions (final IL-21 concentrations between 0.5 and 1.0 ng/mL) of the four T cell conditioned media samples were preincubated for 30 minutes at 37° C. with a 1:4 serial dilution of IL-21 mAb clone 362.78.1.44. The concentration of clone 362.78.1.44 ranged from 0.4 to 400 ng/mL. After 30 minutes, the conditioned media +IL-21 mAb samples were transferred to the Baf3/hIL-21R cell plate and incubated for an additional 10 minutes at 37° C. After 10 minutes, the reactions were stopped with cold wash buffer, cells lysed and amount of pSTAT3 measured using the method described in Example 7.

In all four conditioned media samples, the clone 362.78.1.44 IL-21 mAb effectively neutralized IL-21 activity (data summarized in Table 15). These data clearly demonstrate effective binding to and neutralization of native human IL-21 by clone 362.78.1.44.

TABLE 15

Neutralization of native IL-21 by IL-21 mAb clone 362.78.1.44

| IL-21 mAb Conc. | pSTAT3 induction (fold over background) | | | |
|---|---|---|---|---|
| (ng/mL) | Donor 1 | Donor 2 | Donor 3 | Donor 4 |
| 0.4 | 69.49 | 56.32 | 61.11 | 62.73 |
| 1.6 | 70.84 | 61.73 | 68.24 | 65.41 |
| 6.25 | 70.76 | 10.46 | 7.51 | 60.65 |
| 25 | 2.16 | 1.62 | 1.70 | 2.49 |
| 100 | 168 | 1.43 | 1.51 | 1.49 |
| 400 | 1.59 | 1.30 | 1.14 | 1.51 |

Example 21

21A. Pilot Toxicity Study with IL-21 mAb 362.78-CHO in Cynomolgus Monkeys

The epitope specificity of IL-21 mAb 362.78-CHO is shared by humans, rhesus and cynomolgus macaques (see Examples 17 and 17b), therefore tolerability and toxicity of IL-21 mAb was tested in cynomolgus monkeys, a relevant species for safety assessment.

Cynomolgus monkeys were treated with a single injection of IL-21 mAb 362.78-CHO and monitored for clinical signs for 4 to 8 weeks following treatment. The IL-21 mAb was delivered by subcutaneous or intravenous injection at doses of 5 or 100 mg/kg. No clinical signs were observed. No meaningful changes in body weight or coagulation were observed. No changes in serum chemistry or hematology attributable to drug toxicity were observed. The single treatment with IL-21 mAb 362.78-CHO at 5 or 100 mg/kg was well tolerated by all of the animals.

Necropsy was performed on the high-dose (100 mg/kg) animals. No gross anatomic changes were observed. Histopathology analysis of the high-dose animals showed minimal lymphoid hyperplasia in lymphoid tissues. Immunohistochemistry analysis of lymphoid tissues showed a moderate increase in follicle size and in follicle-associated cell types. These changes could relate to the pharmacological activity of IL-21 mAb 362.78-CHO, since IL-21 is known to directly affect the development and egress of B cells from lymphoid follicles and to support class switch, affinity maturation and plasma cell development.

Pharmacokinetic behavior and bioavailability of IL-21 mAb 362.78-CHO was monitored in a single dose study in cynomolgus monkeys. Eight male cynomolgus monkeys were treated with IL-21 mAb 362.78-CHO. Three were treated by subcutaneous injection of 5 mg/kg and three were treated by intravenous injection of 5 mg/kg. Two were treated by intravenous injection of 100 mg/kg. Serum samples were taken for analysis of IL-21 mAb 362.78-CHO levels during four weeks following treatment for the 100 mg/kg group and during eight weeks following treatment for the two 5 mg/kg groups. Noncompartmental analysis of pharmacokinetic profiles showed that exposure increased in a dose-proportional manner with intravenous administration of 5 or 100 mg/kg IL-21 mAb. Bioavailability of IL-21 mAb 362.78-CHO was approximately 50% following subcutaneous administration. The estimated terminal half-life for IL-21 mAb was 10-14 days. The estimated terminal half-life of IL-21 mAb*insert: 362.78-CHO in cynomolgus monkeys was 10-14 days.

21B. Pilot Pharmacology Study with 362.78-CHO in Cynomolgus Monkeys

The epitope specificity of IL-21 mAb 362.78-CHO is shared by humans, rhesus and cynomolgus macaques (see Examples 17 and 17b), therefore in vivo pharmacology of IL-21 mAb was tested in cynomolgus monkeys, a relevant species for pharmacodynamic assessment.

Cynomolgus monkeys were treated with a single injection of IL-21 mAb 362.78-CHO and monitored for clinical signs for 4 to 8 weeks following treatment. The IL-21 mAb 362.78-CHO was delivered by subcutaneous or intravenous injection at doses of 5 or 100 mg/kg. All animals were monitored for changes in peripheral blood leukocyte composition by flow cytometry. No treatment-related changes in monocyte or B cell concentration, and no changes in T cell CD4 and CD8 subsets, nor in the ratio of CD4 to CD8 cells, were observed. A reduction in the NK cell concentration was observed following IL-21 mAb 362.78-CHO administration. In all treatment groups, peripheral blood NK cells were decreased at 24 h post-treatment, relative to the baseline values. In five of the eight animals, NK levels remained below 60% of the baseline value for at least two weeks. A confirmatory study with adequate controls for handling stress and other sources of variability in peripheral blood NK cell concentration will be required to confirm this observation.

Example 22

Anti-mIL-21 Antibody Decreases Disease Incidence and Progression in Mouse Collagen Induced Arthritis (CIA) Model Mouse Collagen Induced Arthritis (CIA) Model:

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, Curr. Opin. Rheum. 3:407-20, 1999; Williams et al., Immunol. 89:9784-788, 1992; Myers et al., Life Sci. 61:1861-78, 1997; and Wang et al., Immunol. 92:8955-959, 1995). The potential efficacy of a rat anti-mouse IL-21 mAb produced at ZymoGenetics was tested in the CIA model, as described below.

Ten-week old male DBA/1J mice (Jackson Labs) were used for therapeutic dosing (i.e. as mice get established disease). On day −21, all animals were given an intradermal tail injection of 100 microliters of 1 mg/mL chick Type II collagen formulated in Complete Freund's Adjuvant (prepared by Chondrex, Redmond, Wash.), and three weeks later on Day 0 they were given the same injection except prepared in Incomplete Freund's Adjuvant. An anti-IL-21 antibody or vehicle (PBS) was administered as an intraperitoneal injection every other day for a total of 6 doses as soon as a mouse developed established disease. Mice (n=7 per treatment) received either 0.15 mg of an anti-IL-21 antibody per animal per dose, or the vehicle control, PBS (Life Technologies, Rockville, Md.). Animals began to show symptoms of arthritis following the second collagen injection, with most animals developing inflammation within 1-2 weeks. The extent of disease was evaluated in each paw by using a caliper to measure paw thickness, and by assigning a clinical score (0-3) to each paw (see below).

Monitoring Disease:

Animals can begin to show signs of paw inflammation soon after the second collagen injection, and some animals may even begin to have signs of toe inflammation prior to the second collagen injection. Most animals develop arthritis within 1-2 weeks of the boost injection, but some may require a longer period of time. Incidence of disease in this model is typically 90-100%, and 0-5 non-responders (determined after 6 weeks of observation) are typically seen in a study using 60 animals. Since this study only included mice with established disease, mice that did not develop arthritis were not used. Note that as inflammation begins, a common transient occurrence of variable low-grade paw or toe inflammation can occur. For this reason, an animal was not considered to have established disease until marked, persistent paw swelling had developed.

All animals were observed daily to assess the status of the disease in their paws, which was done by assigning a qualitative clinical score to each of the paws. Every day, each animal had its 4 paws scored according to its state of clinical disease. To determine the clinical score, the paw can be thought of as having 3 zones, the toes, the paw itself (manus or pes), and the wrist or ankle joint. The extent and severity of the inflammation relative to these zones was taken into account including: observation of each toe for swelling; torn nails or redness of toes; notation of any evidence of edema or redness in any of the paws; notation of any loss of fine anatomic demarcation of tendons or bones; evaluation of the wrist or ankle for any edema or redness; and notation if the inflammation extends proximally up the leg. A paw score of 1, 2, or 3 was based first on the overall impression of severity, and second on how many zones were involved. The scale used for clinical scoring is shown below.

Clinical Score:

0=Normal 0.5=One or more toes involved, but only the toes are inflamed

1=mild inflammation involving the paw (1 zone), and may include a toe or toes

2=moderate inflammation in the paw and may include some of the toes and/or the wrist/ankle (2 zones)

3=severe inflammation in the paw, wrist/ankle, and some or all of the toes (3 zones)

Established disease was defined as a qualitative score of paw inflammation ranking 1 or more, that persisted for two days in a row. Once established disease was present, the date was recorded and designated as that animal's first day with "established disease".

Mice receiving an anti-mIL-21 antibody were characterized by a reductions in paw swelling over the course of the experiment and had an approximately 25% lower average arthritis score compared to mice receiving PBS. These results indicate that an anti-mIL-21 antibody reduced paw swelling and disease progression associated with this model of arthritis and suggest that an anti-IL-21 antibody may be efficacious in the treatment of human arthritis.

Example 23

Expression of IL-21R in Human Psoriatic Skin Samples

Expression of IL-21R is generally limited to cells of hematopoietic origin. However, in settings of inflammatory disease, IL-21R expression on non-hematopoietic cells may provide a direct stimulus to cell types that mediate the functional changes in the affected tissues. In psoriasis, keratinocyte growth is dysregulated, with psoriaform epidermal hyperplasia, aberrant terminal differentiation, and incomplete development of the stratum corneum. The IL-21 produced by infiltrating Th1 and Th17 cells in psoriatic skin could promote functional changes in keratinocytes, including cell proliferation, production of chemokines, and altered differentiation. The presence of IL-21R on keratinocytes in psoriatic skin lesions was therefore investigated.

Methods: Immunohistochemistry analysis of 18 skin biopsy samples from 4 normal human donors and 9 patients with psoriasis was performed, using a mouse IgG1 antibody against human IL-21R produced at ZymoGenetics. For the psoriasis patients, a subset (5) provided samples from both lesional and non-lesional skin. A high degree of epidermal hyperplasia was noted in histopathology examination of the lesional skin from all donors. Immunoreactivity (staining) of IL-21R on specific cell types was scored based on frequency of positive cells and intensity of staining.

Results: In normal skin and in non-lesional skin of psoriasis patients, staining for IL-21R was positive on occasional intra-epidermal mononuclear (MNC), scattered macrophages and fibroblast-like cells. Positive staining for IL-21R was present on high numbers of MNC in all of the lesional samples from psoriasis patients. Samples stained with a mouse isotype control antibody were negative. Minimal or no staining for IL-21R was present on epidermal keratinocytes from normal skin. In non-lesional skin biopsies from psoriasis patients, mild staining was observed in epidermal keratinocytes in 4 samples, and moderate staining was observed in the stratum spinosum in the fifth sample. There was mild to strong staining of focal areas of keratinocytes in the lesional samples from 8 of the 9 psoriasis patients.

Conclusion: In psoriatic skin lesions, the expression of IL-21R is not limited to infiltrating leukocytes but is also up-regulated on epidermal keratinocytes. The presence of increased staining for IL-21R on epidermal keratinocytes in non-lesional skin from psoriasis patients, compared with normal controls, suggests that even in non-involved skin, the keratinocytes may respond aberrantly to IL-21 stimulation. In the presence of inflammation, increased IL-21R on infiltrating MNC and in the hyperplastic epidermal layer was noted.

Treatment of psoriasis with an IL-21 blocking antibody may therefore inhibit inflammation by blocking IL-21 signals to both inflammatory cells and epidermal keratinocytes.

TABLE 16

IL-21R Immunoreactivity[1] in Normal, Non-Lesional, and Lesional Psoriatic Skin

| Skin Type (N) | Epidermis[2] | MNC[2] |
| --- | --- | --- |
| Normal (4) | 0 | 1 |
| Psoriasis Non-Lesional (5) | 1 | 1 |
| Psoriasis Lesional[3] (9) | 2 | 3 |

[1]Scale: 0 = none, 1 = mild, 2 = moderate, and 3 = strong for IL-21R expression
[2]Median score of all samples tested
[3]Five of the samples had donor-matched non-lesional skin biopsies

What is claimed is:

1. An isolated monoclonal antibody that binds to IL-21, or an antigen-binding fragment thereof, comprising:
   a heavy chain variable region comprising the amino acid sequences set forth in SEQ ID NOs: 47, 49, and 51, and a light chain variable region comprising the amino acid sequences set forth in SEQ ID NOs: 55, 57, and 59.

2. The antibody of claim 1, wherein the Fc portion of the antibody is selected from the group consisting of IgG1, IgG2, and IgG4.

3. The antibody of claim 2, wherein the Fc portion of the antibody is modified with amino acid substitutions to reduce effector functions.

4. An isolated monoclonal antibody that binds IL-21, or an antigen-binding fragment thereof, comprising amino acid residues 20 to 145 of SEQ ID NO: 45 and amino acid residues 21 to 126 of SEQ ID NO: 53.

5. The antibody or fragment of claim 4, comprising amino acid residues 1 to 145 of SEQ ID NO: 45 and amino acid residues 21 to 126 of SEQ ID NO: 53.

6. The antibody of claim 5, wherein the Fc portion of the antibody is selected from the group consisting of IgG1, IgG2, and IgG4.

7. The antibody of claim 6, wherein the Fc portion of the antibody is modified with amino acid substitutions to reduce effector functions.

8. An antibody produced by the hybridoma designated 362.597.3, wherein the hybridoma is deposited with the American Type Culture Collection having the ATCC Patent Deposit Designation PTA-8786.

9. An isolated monoclonal antibody that binds to IL-21, or an antigen-binding fragment thereof, comprising amino acid residues 20 to 145 of SEQ ID NO: 45 or amino acid residues 21 to 126 of SEQ ID NO: 53.

10. An isolated monoclonal antibody, or an antigen-binding fragment thereof, which binds to the same epitope as an antibody comprising amino acid residues 20 to 145 of SEQ ID NO:45 and amino acid residues 21 to 126 of SEQ ID NO:53.

11. A composition comprising the antibody or fragment of claim 4, 9, or 10 and a pharmaceutically acceptable carrier.

* * * * *

UNITED STATES PATENT AND TRADEMARK OFFICE
CERTIFICATE OF CORRECTION

PATENT NO.         : 8,241,629 B2
APPLICATION NO.    : 12/971495
DATED              : August 14, 2012
INVENTOR(S)        : Stephen R. Jaspers et al.

Page 1 of 1

It is certified that error appears in the above-identified patent and that said Letters Patent is hereby corrected as shown below:

On the title page, line 11 of the Other Publications section, replace "Bc1-6" with --Bcl-6--.

On the title page, line 17 of the Other Publications section, replace "duragble" with --durable--.

On the title page, line 4 of the Abstract, replace "recombinat" with --recombinant--.

On the title page, line 8 of the Abstract, replace "B cells $T_H$ cells" with --B cells, $T_H$ cells--.

Signed and Sealed this
First Day of January, 2013

David J. Kappos
*Director of the United States Patent and Trademark Office*